US012673140B2

(12) United States Patent
Albert et al.

(10) Patent No.: US 12,673,140 B2
(45) Date of Patent: Jul. 7, 2026

(54) BLADDER, URETER, KIDNEY, URETHRA, PROSTATE AND CATHETER ANTI-MICROBIAL, AND BIOFILM PREVENTION, REDUCTION AND TREATMENT

(71) Applicant: UHI, LLC, Shaker Heights, OH (US)

(72) Inventors: Kristina Albert, Shaker Heights, OH (US); Carmen Fonseca, Shaker Heights, OH (US); Afif Ghannoum, Shaker Heights, OH (US)

(73) Assignee: UHI, LLC, Shaker Heights, OH (US)

( * ) Notice: Subject to any disclaimer, the term of this patent is extended or adjusted under 35 U.S.C. 154(b) by 807 days.

(21) Appl. No.: 17/789,928

(22) PCT Filed: Dec. 22, 2020

(86) PCT No.: PCT/US2020/066653
§ 371 (c)(1),
(2) Date: Jun. 29, 2022

(87) PCT Pub. No.: WO2021/138156
PCT Pub. Date: Jul. 8, 2021

(65) Prior Publication Data
US 2023/0050626 A1     Feb. 16, 2023

Related U.S. Application Data

(60) Provisional application No. 62/954,774, filed on Dec. 30, 2019.

(51) Int. Cl.
*A61L 29/16*     (2006.01)
*A61L 29/08*     (2006.01)

(52) U.S. Cl.
CPC ............. *A61L 29/16* (2013.01); *A61L 29/085* (2013.01); *A61L 2300/208* (2013.01); *A61L 2300/406* (2013.01)

(58) Field of Classification Search
CPC .. A61L 29/16; A61L 29/085; A61L 2300/208; A61L 2300/406; A61L 29/14; A61L 2300/404; Y02A 50/30; A61K 9/0034; A61K 31/4425; A61P 13/00
See application file for complete search history.

(56) References Cited

U.S. PATENT DOCUMENTS

| | | | |
|---|---|---|---|
| 3,865,472 A | 2/1975 | Hobart et al. | |
| 3,993,777 A | 11/1976 | Caughman et al. | |
| 4,292,299 A | 9/1981 | Suzuki et al. | |
| 4,590,067 A | 5/1986 | Meisner | |
| 4,657,758 A | 4/1987 | Goldemberg et al. | |
| 5,095,106 A | 3/1992 | Gaffar et al. | |
| 5,124,359 A | 6/1992 | Wachman et al. | |
| 5,401,723 A | 3/1995 | Gaffar et al. | |
| 5,422,098 A | 6/1995 | Rolla et al. | |
| 5,733,540 A | 3/1998 | Lee | |
| 5,776,479 A | 7/1998 | Pallos et al. | |
| 6,368,576 B1 | 4/2002 | Jensen et al. | |
| 6,663,902 B1 | 12/2003 | Hei et al. | |
| 6,666,902 B1 | 12/2003 | Kimura et al. | |
| 6,682,722 B2 | 1/2004 | Majeti et al. | |
| 6,713,049 B1 | 3/2004 | White, Jr. et al. | |
| 6,749,869 B1 | 6/2004 | Richter et al. | |
| 6,977,082 B2 | 12/2005 | Seitz, Jr. et al. | |
| 8,535,646 B2 | 9/2013 | Sokol et al. | |
| 8,992,893 B2 | 3/2015 | Sokol et al. | |
| 10,398,645 B2 | 9/2019 | Sokol et al. | |
| 10,426,761 B2 | 10/2019 | Ghannoum et al. | |
| 2002/0156130 A1 | 10/2002 | Melman | |
| 2002/0168334 A1 | 11/2002 | Jacob et al. | |
| 2003/0206874 A1 | 11/2003 | Doyle et al. | |
| 2003/0232074 A1 | 12/2003 | Ipford et al. | |
| 2004/0009245 A1 | 1/2004 | Vail, III et al. | |
| 2004/0102429 A1 | 5/2004 | Modak et al. | |
| 2004/0126334 A1 | 7/2004 | White, Jr. et al. | |
| 2005/0025833 A1 | 2/2005 | Aschkenasy et al. | |
| 2005/0058673 A1 | 3/2005 | Scholz et al. | |
| 2005/0163727 A1 | 7/2005 | Doyle et al. | |

(Continued)

FOREIGN PATENT DOCUMENTS

| | | | |
|---|---|---|---|
| BR | 112013026965 B2 | 4/2012 | |
| CA | 2832854 A1 | 10/2012 | |

(Continued)

OTHER PUBLICATIONS

United Kingdom Office Action dated Jun. 21, 2023 in connection with Application Serial No. GB2210704.9.
United Kingdom Office Action dated Sep. 8, 2023 in connection with Application Serial No. GB2210704.9.
United Kingdom Office Action dated Dec. 1, 2023 in connection with Application Serial No. GB2210704.9.
Baharlou, Simin, "International Preliminary Report on Patentability for PCT Patent Application No. PCT/US2013/066863", Mailed Date: Jul. 7, 2015, 11 pages.
Baharlou, Simin, "International Preliminary Report on Patentability for PCT Patent Application No. PCT/US2014/010174", Mailed Date: Jul. 7, 2015, 6 pages.
Becamel, Philippe, "International Preliminary Report on Patentability for PCT Patent Application No. PCT/US2012/033921", Mailed Date: Oct. 22, 2013, 7 pages.
Chinese State Intellectual Property Office, "First Office Action for Chinese Patent Application No. 201280030293.7", Mailed Date: Mar. 12, 2015, 17 pages.

(Continued)

*Primary Examiner* — Snigdha Maewall
(74) *Attorney, Agent, or Firm* — Eschweiler & Potashnik, LLC

(57) ABSTRACT
A method for preventing and treating internal infections, e.g., urinary tract infections, caused by catheters is provided, in particular by reduction in catheter-associated biofilms. A coating composition is used to treat the catheter and applied through the catheter into the bladder or other body urinary tract organ to kill or neutralize microorganisms, including biofilms therein. The composition comprises a humectant and an antimicrobial with the antimicrobial including a monoquaternary ammonium compound or pharmaceutically acceptable salt thereof. The coating layer has antimicrobial cidal or static activity for at least about one hour.

20 Claims, 38 Drawing Sheets

(56) References Cited

U.S. PATENT DOCUMENTS

| | | | |
|---|---|---|---|
| 2005/0169852 A1 | 8/2005 | Roberge et al. | |
| 2005/0182021 A1 | 8/2005 | Nichols et al. | |
| 2006/0063712 A1 | 3/2006 | Chiueh et al. | |
| 2006/0166943 A1 | 7/2006 | Van Roey et al. | |
| 2006/0251684 A1 | 11/2006 | Annis et al. | |
| 2007/0037723 A1 | 2/2007 | McDonnell et al. | |
| 2007/0166244 A1 | 7/2007 | Ghosh et al. | |
| 2007/0281999 A1 | 12/2007 | Fox et al. | |
| 2008/0064711 A1 | 3/2008 | Friedman | |
| 2008/0206155 A1 | 8/2008 | Tamarkin et al. | |
| 2008/0255498 A1 | 10/2008 | Houle | |
| 2008/0287538 A1 | 11/2008 | Scholz et al. | |
| 2008/0317703 A1 | 12/2008 | Kawa et al. | |
| 2009/0081294 A1 | 3/2009 | Gin et al. | |
| 2009/0149429 A1 | 6/2009 | Arranz Plaza et al. | |
| 2009/0221989 A1* | 9/2009 | Najafi | A61K 33/06 |
| | | | 424/679 |
| 2009/0226541 A1 | 9/2009 | Scholz et al. | |
| 2009/0238777 A1 | 9/2009 | Joziak et al. | |
| 2009/0251684 A1 | 10/2009 | Arai et al. | |
| 2010/0055152 A1 | 3/2010 | Wahi | |
| 2012/0270909 A1 | 10/2012 | Sokol et al. | |
| 2013/0039959 A1 | 2/2013 | Sokol et al. | |
| 2013/0123308 A1 | 5/2013 | Ghannoum et al. | |
| 2013/0123309 A1 | 5/2013 | Ghannoum et al. | |
| 2013/0272971 A1 | 10/2013 | Pimenta et al. | |
| 2014/0005236 A1 | 1/2014 | Sokol et al. | |
| 2014/0051731 A1 | 2/2014 | Ghannoum et al. | |
| 2014/0051732 A1* | 2/2014 | Ghannoum | A61K 47/26 |
| | | | 514/358 |
| 2015/0031729 A1 | 1/2015 | Ghannoum et al. | |
| 2015/0306042 A1 | 10/2015 | Ghannoum et al. | |

FOREIGN PATENT DOCUMENTS

| | | | |
|---|---|---|---|
| CN | 101868145 A1 | 10/2010 | |
| DE | 19529862 A1 | 2/1997 | |
| EP | 351301 A2 | 1/1990 | |
| EP | 376363 A1 | 7/1990 | |
| EP | 0736250 A1 | 10/1996 | |
| EP | 1930012 A1 | 6/2008 | |
| EP | 2100590 A1 | 9/2009 | |
| EP | 2119426 A1 | 11/2009 | |
| EP | 2193777 A1 | 6/2010 | |
| EP | 2226069 A1 | 9/2010 | |
| EP | 2298418 A1 | 3/2011 | |
| EP | 2377577 A1 | 10/2011 | |
| EP | 2699246 A1 | 2/2014 | |
| EP | 2838570 A1 | 2/2015 | |
| EP | 2941248 A1 | 11/2015 | |
| EP | 2941255 A1 | 11/2015 | |
| JP | 861501390 A | 7/1986 | |
| JP | 2000516300 A | 12/2000 | |
| JP | 2001517683 A | 10/2001 | |
| JP | 2003511474 A | 3/2003 | |
| JP | 2007515204 A | 6/2007 | |
| JP | 2008507583 A | 3/2008 | |
| JP | 2008508338 A | 3/2008 | |
| JP | 2008533051 A | 8/2008 | |
| JP | 2008535918 A | 9/2008 | |
| JP | 2009523782 A | 6/2009 | |
| JP | 2014518555 A | 7/2014 | |
| JP | 2016504381 A | 2/2016 | |
| NO | 2012145307 A1 | 10/2012 | |
| RU | 2302865 C2 | 7/2007 | |
| RU | 2325899 C2 | 6/2008 | |
| RU | 2379025 C2 | 1/2010 | |
| WO | 1999059410 A1 | 11/1999 | |
| WO | 2000027191 A1 | 5/2000 | |
| WO | 2004045572 A1 | 6/2004 | |
| WO | 2007001606 A2 | 1/2007 | |
| WO | 2007016067 A2 | 2/2007 | |
| WO | 2008026310 A1 | 3/2008 | |
| WO | 2009067605 A2 | 5/2009 | |
| WO | 2009117644 A1 | 9/2009 | |
| WO | 2011038446 A1 | 4/2011 | |
| WO | 2012087325 A1 | 6/2012 | |
| WO | 2012145307 A1 | 10/2012 | |
| WO | 2013158165 A1 | 10/2013 | |
| WO | 2014074331 A1 | 5/2014 | |
| WO | 2014107221 A1 | 7/2014 | |
| WO | 2014107572 A1 | 7/2014 | |

OTHER PUBLICATIONS

Chinese State Intellectual Property Office, "Second Office Action for Chinese Patent Application No. 201280030293.7", Mailed Date: Dec. 4, 2015, 6 pages.

Commissioner of Patents, "Direction to Request Examination for Australian Patent Application No. 2012245665", Mailed Date: Sep. 15, 2015, 1 page.

Dental Hygiene, 2010, vol. 30, No. 6, p. 566-570.

Department of Health and Human Services (Food and Drug Administration) (1994) Oral Health Care Products for Over-the-Counter Human Use; Tentative Final Monograph for Oral Antiseptic Drug Products. Proposed Rules (21 CFR Part 256, RIN 0905-AA06. Federal Register 59:6084-124.

Dutikova, Y., "International Search Report for PCT Patent Application No. PCT/US2013/066863", Mailed Date: Jan. 30, 2014, 8 pages.

Dutikova, Y., "Written Opinion for PCT Patent Application No. PCT/US2013/066863", Mailed Date: Jan. 30, 2014, 10 pages.

Savchenko, K., "International Search Report for PCT/US2014/010174", Mailed Date: Apr. 29, 2014, 3 pages.

Holloman, Nannette, "Advisory Action for U.S. Appl. No. 13/448,957", Aug. 15, 2014, 3 pages.

Holloman, Nannette, "Final Office Action for U.S. Appl. No. 13/448,957", Jun. 6, 2014, 11 pages.

Holloman, Nannette, "Non-Final Office Action for U.S. Appl. No. 13/448,957", Nov. 18, 2013, 8 pages.

Holloman, Nannette, "Non-Final Office Action for U.S. Appl. No. 13/448,957", Oct. 10, 2014, 11 pages.

Japanese Patent Office, "Office Action for Japanese Patent Application No. 2014-506480", Mailed Date: Dec. 8, 2015, 6 pages.

Johannes, Laura, "Keeping Cold and Flu Germs Out" Wall Street Journal (online) (Dec. 6, 2011) (retrieved on May 4, 2012 from http://online.wsj.com/article/ SB10001424052970204903804577080410897264148.html?mod=WSJ_article_comments#articleTabs%3Darticle ).

Lambert Pharmacal CO, "So many times in a day In Danger" Life magazine, Dec. 1927, (3 pages).

Linder, Nora, "International Preliminary Report on Patentability for PCT Patent Application No. PCT/US2013/066929", Mailed Date: May 12, 2015, 11 pages.

Maremonti, Michele, "Supplementary Partial European Search Report for European Patent Application No. 13777625.8", Mailed Date: Nov. 6, 2015, 5 pages.

Maslova, E., International Search Report and Written Opinion for PCT Patent Application No. PCT/US2013/020254, Mailed Date: May 16, 2013, 18 pages.

Nakamura, Yukari, "International Preliminary Report on Patentability for PCT Patent Application No. PCT/US2013/020254", Mailed Date: Oct. 21, 2014, 11 pages.

Balakrishnan, et al., "Dental Caries is a Preventable Infectious Disease", Australian Dental Journal, vol. 45, No. 4, Dec. 2000, pp. 235-245.

O'Shea, Chloe, First Examination Report for New Zeland Patent Application No. 616044, Mailed Date: Jul. 16, 2014, 3 pages.

Piteen, Frank-Albert et al., "Efficacy of Cetylpyridinium Chloride Used as Oropharyngeal Antiseptic" Arzneim.-Forsch/Drug Res. 51 (II), 588-595 (2001).

Savchenko, K., "Written Opinion for PCT/US2014/010174", Mailed Date: Apr. 29, 2014, 5 pages.

Prokusheva, M., "International Search Report for PCT Patent Application No. PCT/US2012/033921", Mailed Date: Sep. 6, 2012, 4 pages.

(56) References Cited

OTHER PUBLICATIONS

Prokusheva, M., "Written Opinion of the International Searching Authority for PCT Patent Application No. PCT/US2012/033921", Mailed Date: Sep. 6, 2012, 6 pages.
Receiving Section, "Communication Pursuant to Rules 161(2) and 162 EPC for European Patent Application No. 13777625.8", Mailed Date: Dec. 5, 2014, 3 pages.
Receiving Section, "Communication Pursuant to Rules 161(2) and 162 EPC for European Patent Application No. 13870018.2", Mailed Date: Aug. 13, 2015, 2 pages.
Receiving Section, "Communication Pursuant to Rules 161(2) and 162 EPC for European Patent Application No. 14735099.5", Mailed Date: Aug. 14, 2015, 2 pages.
Receiving Section, "Communication Pursuant to Rules 70(2) and 70a(2) EPC for European Patent Application No. 12774888.7", Mailed Date: Sep. 25, 2014, 1 page.
Roberts, Lezah, Final Office Action for U.S. Appl. No. 13/448,926, Mailed Date: May 3, 2013, 26 pages.
Roberts, Lezah, "Final Office Action for U.S. Appl. No. 13/655,365", Mailed Date: Mar. 3, 2015, 10 pages.
Roberts, Lezah, "Final Office Action for U.S. Appl. No. 13/734,363", Mailed Date: Nov. 8, 2013, 10 pages.
Roberts, Lezah, "Final Office Action for U.S. Appl. No. 13/734,470", Jan. 6, 2014, 23 pages.
Roberts, Lezah, "Final Office Action for U.S. Appl. No. 13/734,470", Mar. 17, 2015, 11 pages.
Roberts, Lezah, "Final Office Action for U.S. Appl. No. 14/014,448", Mailed Date: Oct. 24, 2014, 20 pages.
Roberts, Lezah, "Non-Final Office Action for U.S. Appl. No. 13/448,926", Mailed Date: Nov. 27, 2012, 14 pages.
Roberts, Lezah, "Non-Final Office Action for U.S. Appl. No. 13/655,365", Mar. 21, 2014, 13 pages.
Roberts, Lezah, "Non-Final Office Action for U.S. Appl. No. 13/734,363", Mailed Date: Apr. 26, 2013, 19 pages.
Roberts, Lezah, "Non-Final Office Action for U.S. Appl. No. 13/734,470", Mailed Date: Mar. 21, 2013, 20 pages.
Roberts, Lezah, "Non-Final Office Action for U.S. Appl. No. 14/014,448", Jan. 16, 2014, 20 pages.
Roberts, Lezah, "Non-Final Office Action for U.S. Appl. No. 14/014,448", Oct. 26, 2015, 10 pages.
Roberts, Lezah, "Non-Final Office Action for U.S. Appl. No. 14/063,185", Mailed Date: Oct. 8, 2015, 12 pages.
Roberts, Lezah, "Restriction Requirement for U.S. Appl. No. 13/448,926", Mailed Date: Aug. 6, 2012, 7 pages.
Roberts, Lezah, "Restriction Requirement for U.S. Appl. No. 14/063,185", Mailed Date: Apr. 9, 2015, 9 pages.
Roberts, Lezah, "Restriction Requirement for U.S. Appl. No. 14/063,974", Mailed Date: Apr. 9, 2015, 9 pages.
Database Medline [Online] US National Library of Medicine (NLM), Bethesda, MD, US; May 2005 (May 2005), Caufield Page W et al: "Dental Caries: An Infectious and Transmissible Disease.", Database Accession No. NLM17036539; & Compendium of Continuing Education in Dentistry (Jamesburg, N. J.: 1995) May 2005, vol. 26, No. 5 Suppl 1, May 2005 (May 2005), pp. 10-16, ISSN:1548-8578.
Giro, Annalisa, "Communication pursuant to Article 94(3) EPC for European Patent Application No. 12774888.7", Mailed Date: Feb. 17, 2016, 8 pages.
Boukarim, et al., "Preservatives in Liquid Pharamaceutical Preparations", In The Journal of Applied Research, vol. 9, Issue 1, and 2, 2009, 4 pages.
Mohamed, Sotohy A.S., "Studying Effect of pH on the Antimycotic Performance of Some Disinfectants by Using Quantitative Suspension Test", In Ass. Univ. Bull. Environ. Res., vol. 7, No. 1, Mar. 2004, pp. 45-55.
Patent Translation—Jun. 6, 2012 of EP351301.
Watanabe, Akira, "Neuraminidase Inhibitors", In Journal of Clinical and Experimental Medicine, vol. 241, No. 1, pp. 83-86.
Nakamura, Yukari, "International Preliminary Report on Patentability for PCT Patent Application No. PCT/US2020/066653", Mailed Date: Jul. 5, 2022, 5 pages.

* cited by examiner

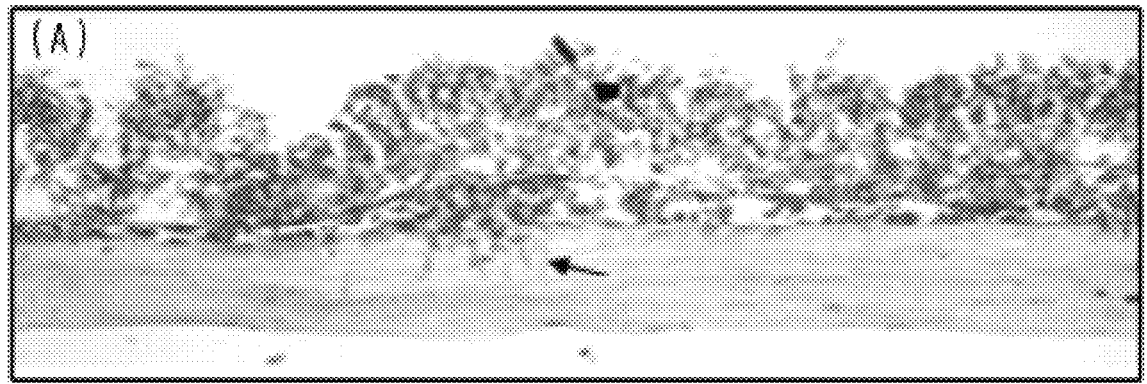
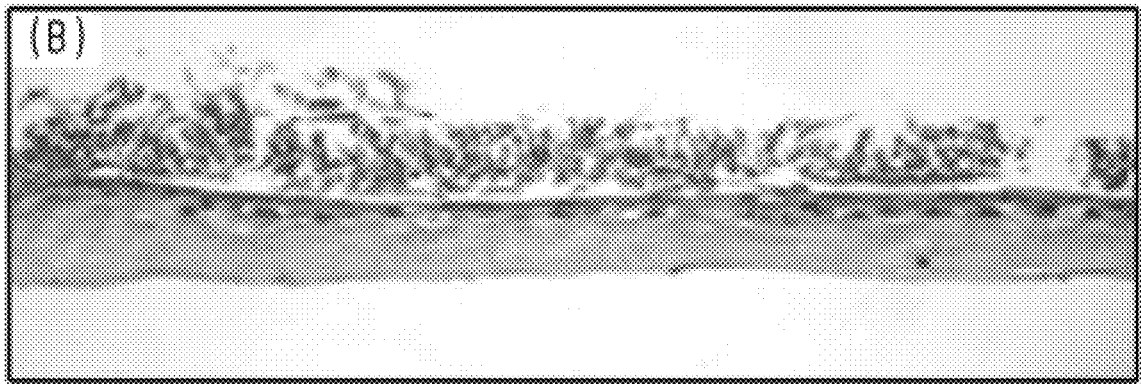
FIG. 5

FIG. 15

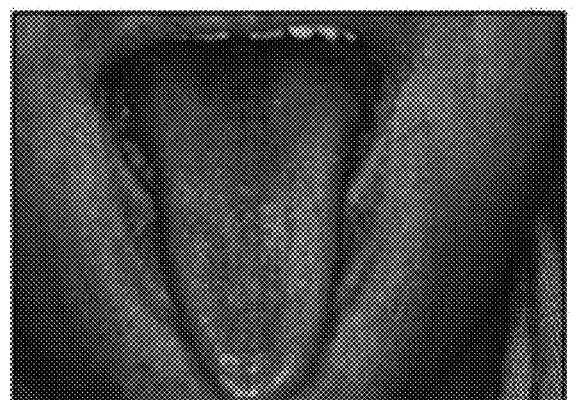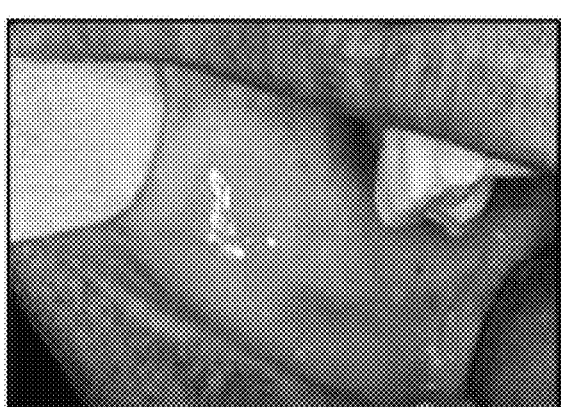
FIG. 21

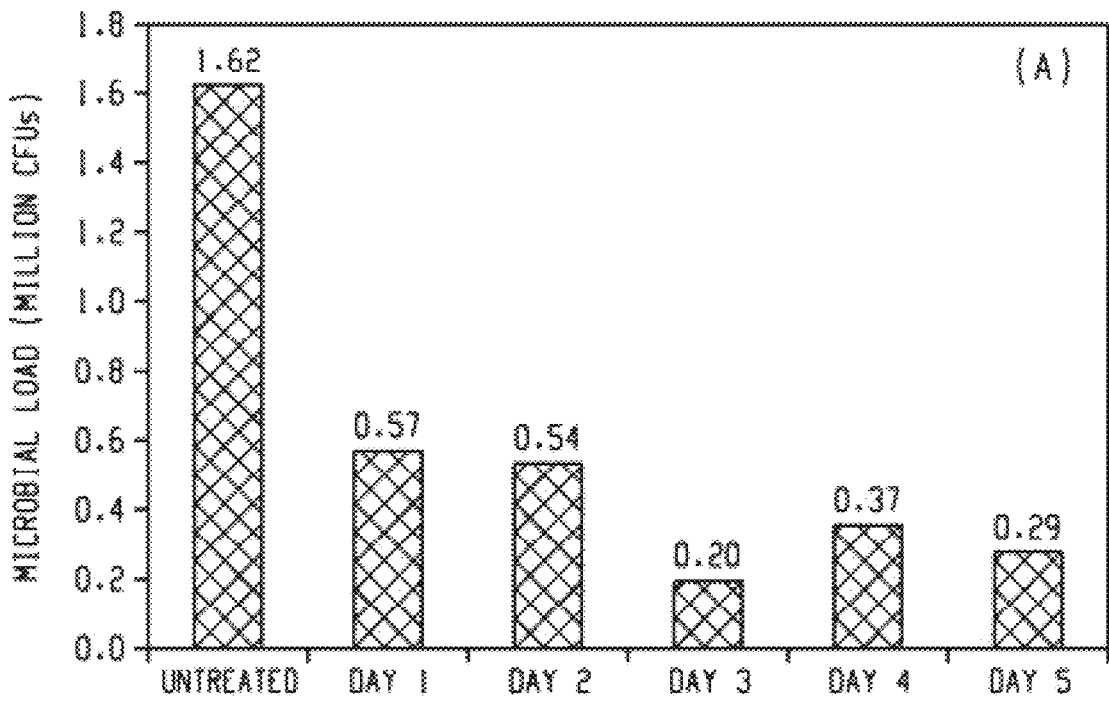
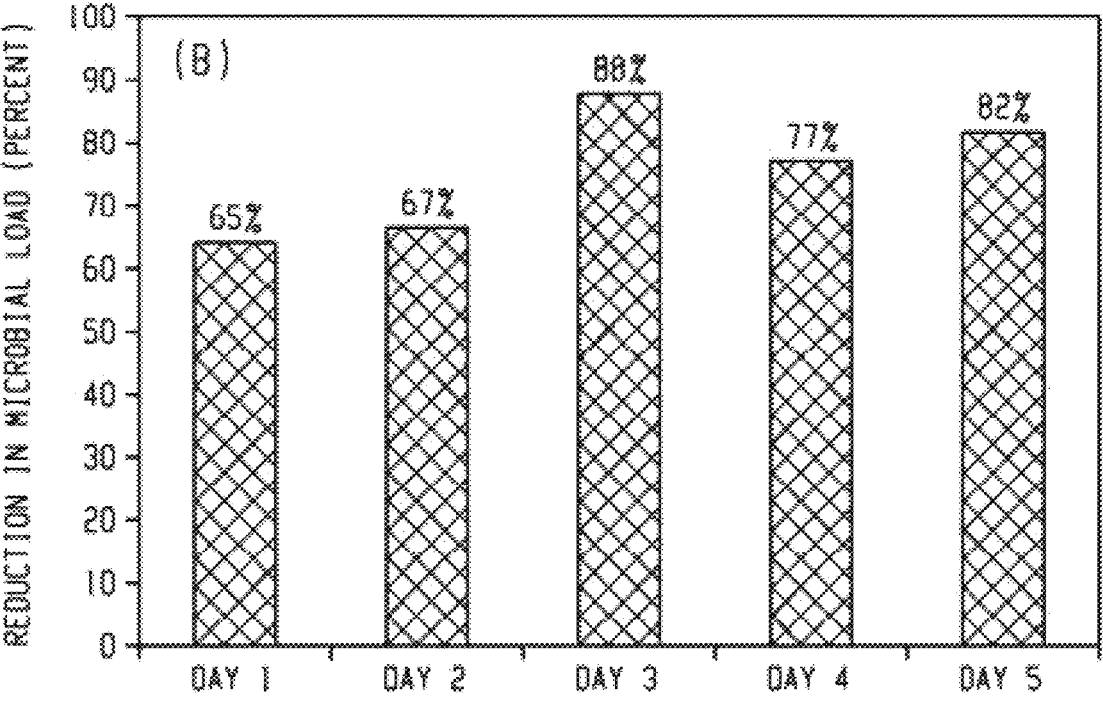
FIG. 24

(A)

(B)

(C)

(D)

(A)                    (B)

(C)                    (D)

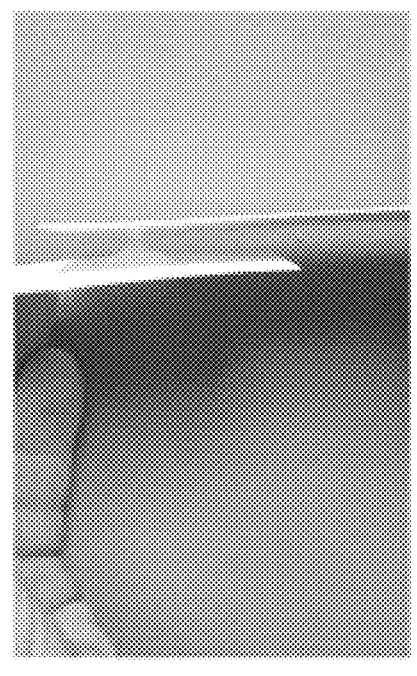
Formulation 1
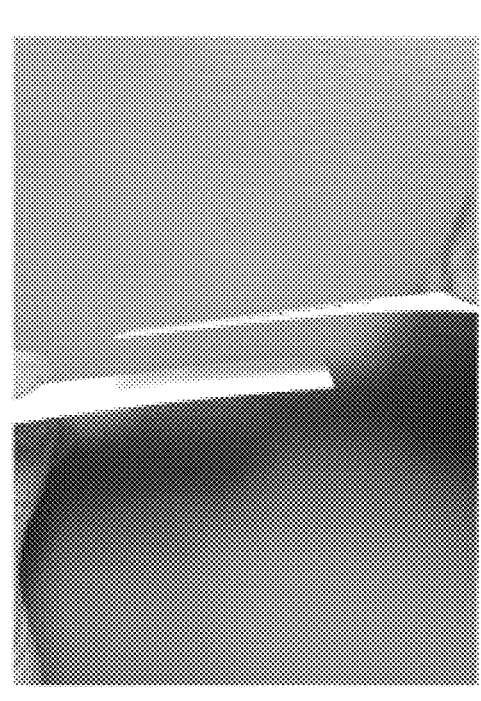
Formulation 2
FIG. 32

Formulation 1                    Formulation 2

Formulation 1                    Formulation 2
FIG. 34

359　　　351　　　358

361

360　366

369

| Sample number | Indwelling time (days) | Organism(s) detected by next-generation sequencing | Proportion of sample | Resistance genes detected |
|---|---|---|---|---|
| 1 | 30 | Enterococcus faecalis | 100% | none |
| 2 | 9 | Staphylococcus epidermidis | 92% | none |
|   |   | Pseudomonas fluorescens | 7% |  |
| 3 | 10 | Staphylococcus aureus | 96% | none |
| 4 | 41 | Staphylococcus aureus | 83% | none |
|   |   | Acinetobacter calcoaceticus | 16% |  |
| 5 | 7 | Enterococcus faecalis | 96% | none |
|   |   | Klebsiella pneumoniae | 3% |  |
| 6 | 43 | Klebsiella pneumoniae | 81% | Beta-lactam |
|   |   | Enterococcus faecalis | 17% |  |
| 7 | 40 | Escherichia coli | 79% | Beta-lactam |
|   |   | Citrobacter freundii | 10% | Macrolide |
|   |   | Enterococcus faecalis | 9% | Aminoglycoside |
|   |   |   |   | Tetracycline |
|   |   |   |   | Quinolone |
| 8 | 21 | Escherichia coli | 93% | none |
|   |   | Enterococcus faecalis | 6% |  |
| 9 | 11 | Escherichia coli | 100% | Beta-lactam |
|   |   |   |   | Quinolone |
| 10 | 13 | Escherichia coli | 100% | Beta-lactam |
|   |   |   |   | Quinolone |

*Fig. 37*

BLADDER, URETER, KIDNEY, URETHRA, PROSTATE AND CATHETER ANTI-MICROBIAL, AND BIOFILM PREVENTION, REDUCTION AND TREATMENT

This application is a National Phase entry application of International Patent Application No. PCT/US2020/066653 filed Dec. 22, 2020, which, in turn, claims priority to U.S. Provisional Patent Application 62/954,774 entitled "Bladder, Ureter, Kidney, Urethra, Prostate and Catheter Anti-Microbial Prevention and Treatment" filed Dec. 30, 2019, the entire disclosures of which are incorporated herein by reference.

FIELD

This disclosure relates to treatments and methods to prevent, reduce, eradicate or neutralize microorganisms and catheter-related biofilms in order to prevent, reduce or treat urinary tract colonizations, infections and infections of the bladder, ureters, urethra, prostate and kidneys and reconstructive substitutions of these urinary tract organs.

BACKGROUND

Urinary tract infections (UTIs) are among the most common bacterial infections worldwide, affecting approximately 150 million people annually. Societal costs attributed to UTIs in the United States are estimated to be $2.5 billion annually. Complicated UTIs may be associated with primary biofilm formations by microorganisms and in 70-80% of complicated urinary tract infections, these infections are due to an indwelling urinary catheter, accounting for 1 million cases annually in the United States. These cases are termed catheter-associated urinary tract infections (CAUTIs) and may also be associated with primary biofilms of the catheters and secondary biofilms of the urinary tract.

There are a number of ongoing efforts to prevent CAUTIs with variable supporting evidence and variable success (PMID: 22508462). Strategies aimed at reducing CAUTI include hand hygiene, sterile technique, closed drainage systems, and novel catheter coatings. For example, silver-alloy coated catheters are available, and used in various practices and hospital settings. In spite of current use, the efficacy and cost-effectiveness of such measures remain unclear PMID (22508462, 10569319, 16418985). CAUTI incidence remains alarmingly high, and there is a critical need for measures to further prevent, reduce or eliminate CAUTI risk.

CAUTIs are initiated via peri-meatal uropathogen introduction into the urethra and ascension toward the bladder. Biofilms protect bacteria from urine turbulence as well as antibiotic penetration and host immune responses, and thus biofilm formation leads to a survival advantage, and persistent and antibiotic resistant infections. Biofilms are initiated when free-floating bacteria are deposited onto surfaces submerged in fluid such as a urinary catheter or urinary system. Biofilms comprise multicellular bacterial communities with scaffolding of extracellular DNA, exopolysaccharides, and pili. Bacterial biofilm eradication is important in the prevention and treatment of CAUTI as well as curbing antibiotic resistance, and gaining an understanding of biofilm formation and progression on catheters is critical. Biofilms are also noted to develop directly on bladder, ureter and kidney tissue surfaces and/or mucosa in addition to foreign bodies such as catheters. Thus, innovations that address both biofilms of catheters and bladder, ureter and kidney tissue surfaces or reconstructive counterparts thereof are likely to be of clinical significance. The term urinary system is used to mean urethra, bladder, ureter and kidney or reconstructive counterparts thereof.

Various sorts of sanitizers and antimicrobials have been developed for use on surfaces to prevent the spread of harmful microorganisms from surface contact. Few of these have the ability to effectively remediate biofilms. While numerous solutions exist for killing microorganisms after they have contacted a person or animal or instrument surface, the effectiveness of such solutions is dependent on recognition of the germ contact and application of the germ-killing composition prior to the microorganism binding to a host cell in the body and prior to the formation of a biofilm on the surface. Hand-washing or surface sanitization typically has a very short-lived duration and many microorganisms will quickly begin regrowth or new microorganisms will become deposited on the surface. Accordingly, solutions for killing microorganisms that cause bladder, ureter and kidney infections are often ineffective for prevention of infection since they are intermittent, transitory options that do not provide sustained antimicrobial duration. Antibiotics are effective for treating many bladder and kidney infections, but these are subject to side-effects, other drug interactions, are susceptible to microorganisms developing a resistance to them, and are known to detrimentally alter the composition of the gut microbiome.

Numerous compositions have been developed for killing germs on medical instruments. However, these compositions typically contain highly volatile organic compounds, and although they almost immediately kill microorganisms, they quickly evaporate and/or are washed or wiped away and do not continue to inhibit microorganism growth for more than a few minutes. In addition, it is unlikely that a quick application of such compositions will kill all the microorganisms present on the surface. Thus, the remaining microorganisms will inevitably begin regrowing in a short time. When a biofilm has developed on the surface, conventional antimicrobials may not be effective to even remove/neutralize/reduce the microorganisms present on the surface at the time of application.

SUMMARY

As disclosed herein, it was determined biofilms are often present on urinary catheters, especially on the intraluminal surface. The bacterial species involved in such biofilm formation was isolated and identified. Also demonstrated herein is a composition that is effective in killing, reducing and/or neutralizing these biofilms and the microorganisms that form them.

The articles "a" and "the," as used herein, mean "one or more" unless the context clearly indicates to the contrary.

The terms "item" and "apparatus" are used synonymously herein.

The term "therapeutic," as used herein, is meant to also apply to preventative and reduction treatment.

The term "or," as used herein, is not an exclusive or, unless the context clearly indicates to the contrary.

The use of the term "mammal" herein, means a human or animal commonly defined as a mammal.

The use of the term "block" or "blocking" herein, includes blocking passage by trapping.

The term "catheter" as used herein includes: (1) any device to instill solutions into the urinary tract, such as syringes that can be fitted with a nozzle or tip to fit to the urethral meatus in order to retrograde fill the bladder; or (2) tubular items used as catheters, such as urinary catheters, nephroureteral catheters, ureteral catheters, and nephrostomy tubes and all forms of ureteral and urethral stents.

BRIEF DESCRIPTION OF THE DRAWINGS

FIG. 5 shows photographs of magnified cross-sections of the coating-composition-treated and untreated engineered human oral mucosa (EHOM) of Examples 31-32.

FIG. 15 presents fluorescent microscopy photographs showing the effect of an example coating composition on against H1N1 virus, as described in Examples 85-86.

FIG. 21 are photographs demonstrating the ability of an example coating composition to coat the oral mucosal surface.

FIG. 24 is a graph showing the effect of an example coating composition on levels of oral microbes over a 5-day period in three healthy adults, as described in Examples 167-169.

FIG. 32 shows photographs depicting a gum-containing embodiment in comparison to a no-gum embodiment demonstrating tackiness, viscosity, and thickness differences.

FIG. 34 shows photographs depicting a gum-containing embodiment in comparison to a no-gum embodiment demonstrating a difference in residue film.

FIG. 37 is a table disclosing an analysis of catheter biofilms.

DETAILED DESCRIPTION

Figure 1A:
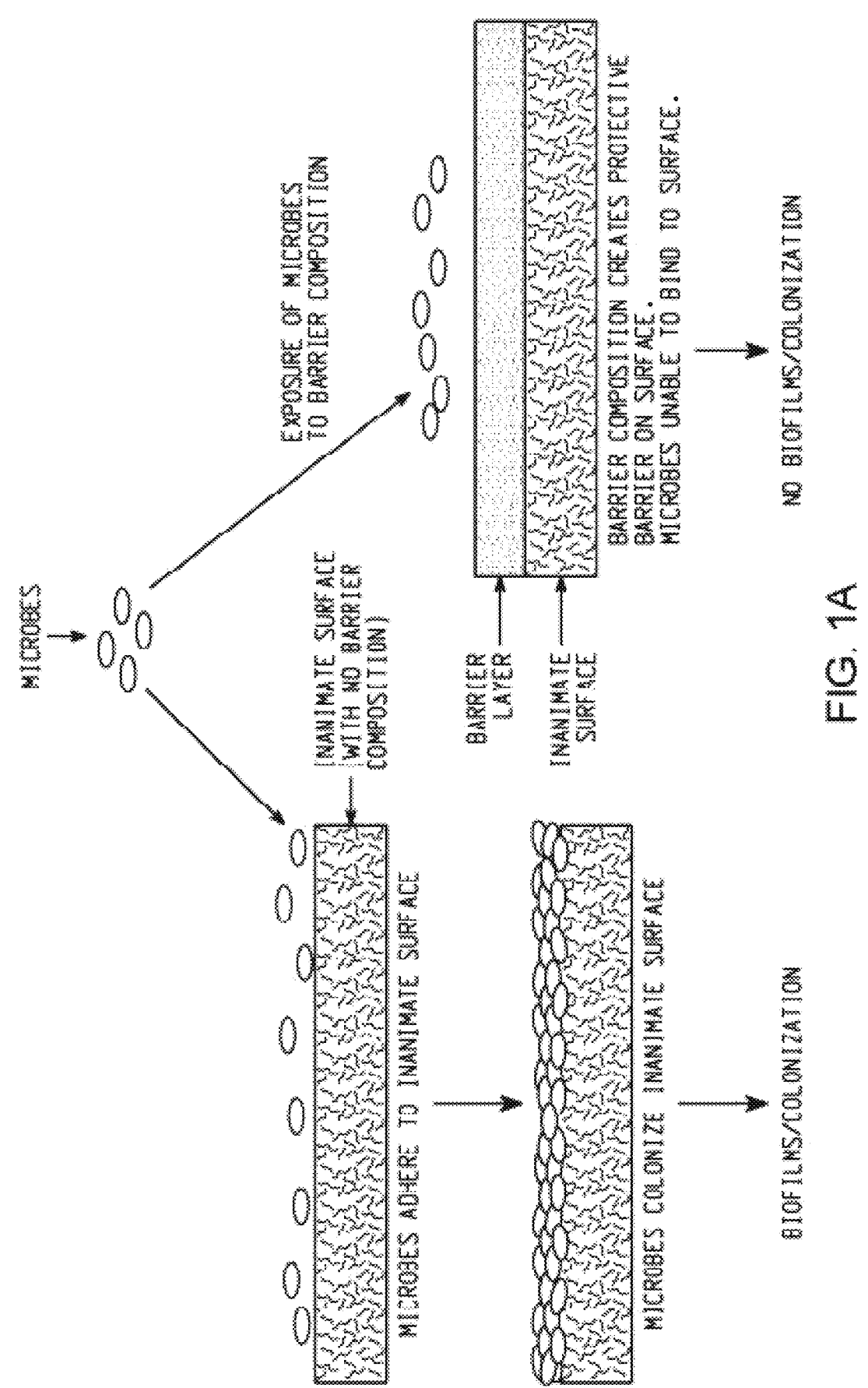
FIG. 1A is an illustrated flow chart of a treated and untreated inanimate surface and the results of an encounter with microorganisms.

This application discloses a stable coating composition for preventing or treating bladder, ureter, urethra, prostate and kidney infections or their reconstructive counterparts and for treating or cleaning catheter surfaces that provides a long-term, sustained microbial static or cidal activity that inhibits, reduces or destroys harmful biofilms. In addition, in embodiments, the composition is also non-toxic for human consumption and safe for human mucosal cells including but not limited to the oropharyngeal lining, the urinary tract or wounds that may occur from urinary tract catheter trauma.

Microorganisms that cause CAUTIs may be introduced from microorganisms encountered on or near the patient during or just before insertion or from contaminated equipment or hands of healthcare workers. Microorganisms may be introduced to the patient during catheter insertion or, in some instances, they may migrate from the exterior of the patient into the urinary tract. Intraluminal contamination can occur when microorganisms access the catheter lumen from a contaminated collection bag or catheter-drainage tube or other routes.

As disclosed herein the composition of the present application is effective against growth of biofilm-forming bacteria isolated from urinary tract catheters, in a dose-dependent manner, including 0.05% antimicrobial, 1:10 (0.005% antimicrobial) and 1:100 (0.0005% antimicrobial) dilutions. This composition is useful to reduce, prevent or treat all urinary tract catheter-associated biofilms and infections, and bladder/kidney and urinary tract biofilms and infections. The antimicrobial may be a quaternary ammonium compound, such as cetyl pyridinium chloride (CPC). CPC has been shown to physically and chemically disrupt the lipid bilayer, and thus is not heavily-influenced by microbial mutations and is effective against a broad range of microbes (Table 1, 28936484, 16162221). The positively-charged quaternary nitrogen of CPC (and other QACs) associates with the head groups of the phospholipids, and CPC's hydrophobic tail then intercalates into the hydrophobic membrane, leading to subsequent microbial cell lysis (16162221).

In an embodiment, a water-based composition containing 0.1% cetylpyridinium chloride, 35% glycerin, as well as small amounts of copovidone, methylparaben, propylparaben, PEG-60 hydrogenated castor oil, sodium benzoate, and xanthan gum, is used as the composition. The activity of this composition has been demonstrated to inhibit the growth of bacteria isolated from biofilms in the lumen of urinary catheters from patients. Thus, the present composition and other antiseptic intralumenal administration to urinary catheters in patients, is an surprisingly effective route for biofilm inhibition and reduction.

As part of this research, it was determined that biofilms causing infections are formed predominantly on the inner surface of urinary tract catheters (specifically bladder catheters), (intraluminal surface). A smaller number of biofilms are found on external surfaces of urinary tract catheters. In an embodiment, the composition is administered via syringe or other medical device to the interior of the catheter tubing. Other related items may be treated as well, including all extension tubing or connection items (catheter containment items such as containment bags) making up an open or closed system of urinary tract management.

In an embodiment, the catheter and associated tubing comprises a material selected from the group consisting of: silicone rubber, nylon, polyurethane, polyethylene terephthalate (PET), latex, thermoplastic elastomers and combinations thereof.

The method of administration includes two methods of treatment: (1) an external catheter treatment where the catheter, especially the exterior surface is coated with the composition; and (2) an intra luminal treatment where the composition is instilled into a catheter that is inserted in the urethra into the bladder, the composition is instilled into the bladder and will elute back into the urethra.

In addition, to remediate biofilm predominance on the balloon aspect or other external aspects of the urinary catheter, the composition disclosed herein can be administered as a coating of the proximal or entire part of any item (including especially the balloon terminal end of the catheter) prior to insertion into the patient, specifically, the urethra in the cases of a bladder catheter, or the kidney or ureter in cases of ureteral stents or percutaneous nephrostomy tubes. The coating may also become uniquely applied to the balloon aspect or other external aspects of the urinary catheter after insertion into the patient, specifically by excess intraluminal treatment that will come in contact with the external aspects of the indwelling urinary catheter as in cases of a bladder catheter, or the kidney or ureteral in cases of ureteral stents or percutaneous nephrostomy tubes.

An instillation treatment with the composition disclosed herein can be performed in two instances. The first is as a preventative treatment to prevent biofilms from forming in a catheter or urinary tract organ (particularly the bladder of the urinary tract) or reconstructed urinary tract organ, without having to remove the catheter for cleaning. In this embodiment, a solution of the composition is passed through the catheter and into the bladder, allowing the composition to contact the bladder surface and allowed to be drained out passively after dwelling in the bladder for a short time, for example, 5 seconds to 1 hour, such as 30 seconds to 30 minutes, or 1 minute to 5 minutes. Based on the numerous examples below (especially Examples 77-84 and 219-224 relative to biofilms), the composition is expected to have a long-lasting effect against infectious microbes and biofilms on every surface the composition touches, including the internal lining of the bladder, the extraluminal and intraluminal surfaces of the catheter, the balloon tip of the catheter and at least a portion of the urinary tract that is not blocked by the terminal end of the catheter.

In an embodiment of a preventative treatment, other types of catheters and tubes, including nephrostomy tubes and external tubing and connected apparatuses are also treated by flowing the composition through them. In an embodiment, the surface should be contacted with a flow or a static presence of the composition for 5 seconds to 60 minutes, such as 10 seconds to 15 minutes, or 20 seconds to 3 minutes. In an embodiment, a bolus of the composition can be moved through the external tube system to sanitize and coat it prior to use with a patient.

In a second instillation treatment, the composition is flowed through the catheter to treat a patient in need of treatment or reduction of an existing infection or biofilm formation. The infection may be caused by a biofilm in the urinary tract, such as the bladder. The composition is instilled into the bladder or other organ through the catheter as described above. However, in this instance, the concentration of the composition, or at least the antimicrobial, may be higher to provide additional activity against the microorganisms causing the infection. The whole composition (or just the CPC component) may be diluted for the prevention or reduction treatment compared to the treatment of infection. For example, the concentration of antimicrobial may be 0.0005% to 0.1% in final solution, such as 0.005% to 0.08% or 0.01% to 0.05%. The volume of composition may be 1 ml to 10,000 mL, such as 3 mLs to 1000 mLs, or 5 mL's to 50 mLs, and the surface should be contacted with a flow or a static presence of the composition for 5 seconds to 60 minutes, such as 10 seconds to 10 minutes, or 30 seconds to 3 minutes. To treat an existing urinary tract or bladder infection, the composition may be applied once every 24 hours to four times per day, e.g. every 6 hours a day or continuously as enabled but not limited to an infusion pump connected to a urinary catheter.

The microorganisms causing the infection may, for example, be *Escherichia coli* (*E. coli*), *Enterococcus* spp., *Klebsiella pneumoniae* (*K. pneumoniae*), *Candida* spp., coagulase-negative Staphylococci, *S. aureus, Proteus mirabilis* (*P. mirabilis*), and *Pseudomonas aeruginosa* (*P. aeruginosa*), *P. fluorescens, Citrobacter* spp. Notably, the broad spectrum antimicrobial composition can treat bacterial and fungal infections, as well as even viral infections.

Once the composition has had a sufficient dwell time in the bladder or other body organ or vessel, the composition is drained out through the catheter and can be disposed of. It is contemplated that in some embodiments the composition will mix with urine in the bladder and be disposed of with the urine.

Figure 35:
FIG. 35 depicts a side view of a catheter and syringe.

FIG. 35 shows a catheter 351 with a syringe 355 inserted into a terminal exterior end 358. In an embodiment, the composition is in the syringe 355 and inserted into the catheter 351 via the syringe 355. The composition flows into the bladder through a terminal balloon tip end 359 of the catheter and dwells in the bladder for a time period.

Figure 36:
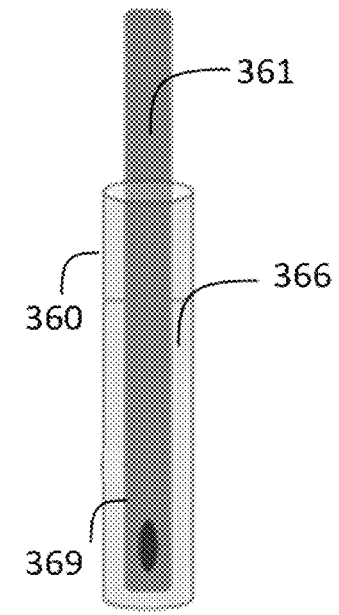
FIG. 36 is a zoomed in view of a terminal end of a catheter in a pre-treatment vial.

FIG. 36 shows a system for coating the terminal balloon tip end 369 of a catheter 361. In this example embodiment, the end of the catheter 361 is dipped into a vial 360 that holds the antimicrobial composition disclosed herein 366, held for 1 second to 1 minute, such as 5 seconds to 40 seconds, or 10 seconds to 20 seconds, removed, and inserted into the urinary tract of a patient. The composition 366 for use on the end of the catheter 361 may have a higher viscosity or not, than the composition used to flow into the bladder through the catheter. The viscosity of the composition 366 for coating the catheter 361, may be, for example, 10 to 500% more viscous, 50% to 300%, or 100% to 200% more viscous than the composition for instillation into the bladder. Additionally, the composition 366 may be in the form of a gel, to facilitate lubrication during catheter 361 insertion. In an embodiment, only a portion of the terminal end 369, e.g. 1 to 5 inches or 1.5 to 3 inches is coated, because a portion of the composition 366 will rub off and coat the exterior of the catheter 361 and urinary tract as the catheter 361 is inserted. In an embodiment, the composition in the vial is high enough to soak an entire balloon aspect of the catheter 361.

In an embodiment, the coating composition presented herein displays low tack (stickiness), has high surface area coverage, low viscosity, low layer thickness, and in a coating layer is transparent and substantially free of visible residue. As such, it may provide advantages over certain embodiments disclosed in prior U.S. application Ser. No. 13/734, 363. It was also discovered that the composition is superior in antimicrobial properties after a water rinse in comparison to a typical commercial surface cleaner.

In an embodiment of the present application, the coating composition is not required to have any carbohydrate gum and may also have a low amount of humectant. In other embodiments both gum and humectant are present in amounts disclosed herein.

Further data presented herein is representative of the treatment of a variety of surfaces to the extent it shows a long-lasting antimicrobial coating composition against a range of microorganisms.

By trapping, killing, and/or neutralizing microorganisms that cause infectious disease on a surface, this in turn inhibits or prevents microorganisms from transferring and disseminating into the body (e.g. the bladder) and causing infection.

In addition, by trapping and/or neutralizing microorganisms (such as, for example yeast) on a surface that are, or can become, detracting from the visual aesthetic appearance of the surface, this will in turn inhibit, and/or stop, detraction of the visual aesthetic appearance of the surface.

The method and composition incorporates an antimicrobial agent that can inhibit or reduce microorganisms, including bacteria, fungi, and viruses, known to cause infections. The method provides a coating layer on a surface by forming a coating layer or film over it and an antimicrobial agent is included that can kill or inhibit microorganisms (bacteria, fungi and viruses). In an embodiment, the coating composition is also effective against microorganisms that cause odor and detraction of the visual aesthetic appearance of surfaces.

Even if the mammal touches the surface and some of the coating composition transfers to their body and comes into contact with human or other mammal mucosa or, for example, surfaces in the oral cavity, nasal cavity, vaginal cavity, throat, the ears and other orifices, the composition, in an embodiment, is safe and non-toxic for such consumption. As the Examples show the product applied directly to mucosal tissue, the surface treatment composition would be expected to be safe even if, for example, a child puts their mouth directly on the treated surface and ingests a portion of the composition.

In fact, in an embodiment, the composition is non-toxic to humans, wherein at least a portion of the composition may be ingested and is safe and non-toxic for human consumption, such as, for example, about 1 ml per day to about 30 mLs per day, such as about 2 mLs per day to about 8 mLs per day, or about 2.5 mLs to about 7.5 mLs. The term "safe," in this context, includes not damaging to normal skin, urinary system surfaces, or mucosal cells or wounds, or causing a reduction in wound healing rate. In an embodiment, at least a portion of the composition may be ingested and is safe for human consumption. Furthermore, the composition is free of harmful side effects on humans.

In an embodiment the coating composition is active to reduce or inhibit microbial growth through static or cidal activity for an extended period of time. Without being bound by theory, the mechanism of action of the coating composition disclosed herein is based on a synergistic dual-action mechanism, in which microorganisms are trapped in the formed coating layer, and subsequently killed by the antimicrobial active ingredient. In an embodiment, the coating composition is not hydrophilic, which, without being bound by theory, is theorized to enhance its sustained effectiveness. For certain applications the composition may be hydrophobic.

In the low tack embodiment of the present application, the coating composition exhibits low tackiness or stickiness. For example, when tested by applying the coating composition onto a paper-stock card and applying another paper-stock card over the coating composition the coating layer may have a draw depth of 0.5 inches or less, such as 0.01 inches to 0.4 inches, or 0.1 inches to 0.03 inches, when applied in a 0.25 ml dosage on a 1 inch diameter area of a paper-stock card, before the coating composition separates entirely from a second paper-stock card set against the coating layer.

In the low tack embodiment of the present application, the coating composition produces a thin layer coating. For example, the coating have an average thickness of from about 50 nanometers to about 0.2 mm, such as about 100 nm to about 900 nm, or about 0.01 mm to about 0.1 mm, or about 0.08 to about 0.15 mm.

In the low tack embodiment of the present application, the coating composition exhibits a substantially streak free appearance or the coating layer is transparent and does not show a visible residue.

As shown in the Examples below, the properties of the coating composition and its effectiveness to prevent a wide variety of communicable diseases were assessed using at least ten different approaches based on: (1) an in vitro anti-microbial susceptibility testing; (2) an in vitro time kill assay; (3) an in vitro biofilm model; (4) an in vitro filter insert-based model, (5) an in vivo-like engineered human oral mucosa (EHOM) model; (6) electron microscopy evaluation; (7) hydrophobicity assay; (8) physico-chemical compatibility assays; (9) cell culture-based model using monolayer of human cell lines; (10) human clinical trials, and (11) a steel surface test with a water rinse.

The method and composition described herein may be particularly useful when a human, or more generally, a mammal, has a disrupted urinary tract lining, or other body surface, e.g., from trauma related to movement of a urinary tract catheter against the surface, or has a condition resulting in an immunocompromised state or is otherwise at a greater risk for urinary tract infection. A disruption may be caused by a wound, scratch, or other opening in the skin or body surface independent of urinary tract catheter trauma. The skin and the surface of the urinary tract and gastrointestinal (GI) tract serve as an important mechanical barrier that helps to prevent a local or systemic invasion of various microbes and the absorption of microbial products that are normally present in the oral cavity, the urinary tract and the lumen of the gut. "Gastrointestinal mucosal injury in experimental models of shock, trauma, and sepsis," Crit. Care Med. 1991; 19:627-41.). Derangement in the barrier function of an internal body surface plays a central role in the pathophysiology of systemic infection. In other words, disruption of the skin or internal body surfaces will lead to infections.

A coating composition that traps and kills harmful microorganisms and that does not interfere with healing of a disrupted skin or other body surfaces is a unique and unexpected solution to the susceptibility of the problems of those with disrupted skin or other body surfaces, particularly those that also have immunodeficiency.

In an embodiment, a coating composition may be applied in a method for preventing or inhibiting the transfer of microorganisms from the surrounding environment (including from surfaces and airborne particulates that later become deposited on a treated surface) to a mammal. By prevention, it is not meant that no infection from microorganisms is possible, but that the risk of infection from microorganisms encountered at the time of application and/or subsequent to application of the coating composition is reduced.

In an embodiment, the coating composition is applied in an effective amount to an inanimate surface and provides a barrier layer on the surface that traps microorganisms, such as by inhibiting microorganisms from penetrating to the other side of the barrier. An antimicrobial is provided that kills or deactivates (neutralizes) the microorganism's harmful activity. The combined barrier and antimicrobial synergistically act to trap, neutralize, and/or kill microorganisms on the inanimate surface or microorganisms that subsequently come into contact with an exposed (top) surface of the barrier, thereby providing a long-lasting antimicrobial that is significantly more powerful than just an antimicrobial alone. The coating composition is effective to trap and kill or neutralize microorganisms already present on the treated surface and/or to kill or neutralize microorganisms that may be deposited on top of the coating, i.e., the exposed surface of the coating, after the application of the coating composition is performed. In an embodiment, the coating composition is active for at least about one hour after application.

This dual action composition and method (barrier coating plus antimicrobial) is applicable to various surfaces found in a variety of places, including for example, homes, schools, churches, restaurants, daycares, workplaces, vehicles and medical buildings, such as, for example, ceramic, glass, wood, (including, for example, varnished, stained, or waxed wood), linoleum, CORIAN (a composition of acrylic polymer and aluminum trihydrate), Formica, porcelain, metal (including, for example, stainless steel, steel, iron, wrought iron, copper, brass, bronze, silver, gold, platinum, aluminum, and alloys of such metals), ceramic, painted surfaces, carbon fiber, textile materials (including, for example, wool, silk, cotton, hemp, sisal, velvet, aramid, acrylic, olefins, nylon, rayon, and spandex), concrete, stone (including, for example, granite, marble, soapstone, limestone, Jerusalem stone, quartz, travertine, and slate), plastic, tile, carpet, leather, laminate material, and rubber. Types of inanimate surfaces include, for example, countertop, table top, flooring, fixtures, furniture, toilet bowl, toilet seat, toilet flush knob, doorknob, faucet, bathtub, shower, hot tub, sauna, sink, clothing, food preparation equipment, playground equipment, toys, shoes, shoe inserts, sporting and fitness equipment, appliance housings, airplane interiors, military vehicle interiors, theater seating, surfaces in healthcare facilities, surfaces in high-traffic public spaces, surfaces in lobbies, surfaces in hotels, surfaces in cruise ships, surfaces in schools, surfaces in dormitories, surfaces in public transportation vehicles, surfaces in adult and child care facilities, surfaces in commercial kitchens, surfaces in manufacturing facilities, surfaces in restaurants, electronic input devices, dishware, and cutlery.

FIG. 1A is an illustrated flow chart of microbes encountering an untreated inanimate surface (left side) and an inanimate surface with the coating composition administered on it resulting in a formed barrier coating layer (right side) that shows a primary efficacy of the coating composition on an inanimate surface. When treating an inanimate surface, the barrier coating layer prevents microorganisms from binding to the surface, colonizing and forming a biofilm. Biofilms are known to be difficult to destroy. The coating composition thus presents a surprisingly effective solution to providing a sanitized surface in comparison to cleaners that only focus on killing microorganisms that are only already on the surface. While an antimicrobial solution that does not form a barrier coating will instantly kill some of the microorganisms in a biofilm on a surface, it is practically impossible to kill all microorganisms in a biofilm and the biofilm will soon begin to recolonize. In an embodiment, the coating composition prevents biofilms from forming in the first place and also has prolonged activity to destroy already formed biofilms. While the low tack embodiment of the coating composition may not be as robust at preventing passage of microorganisms as other embodiments with more humectant and carbohydrate gum, it was found to be effective in killing or neutralizing the microorganisms and was shown to have potent activity against MRSA.

In an embodiment, the coating composition traps and/or kills or neutralizes all harmful microorganisms contacting the coating composition. In another embodiment, the barrier coating substantially traps and/or kills or neutralizes enough harmful microorganisms that contact the coating composition to inhibit or even stop them from causing an infectious disease. In vitro testing shows that in viruses exposed to embodiments of the coating composition, growth may be inhibited for about two or more days (such as influenza), up to about nine days, (such as HIV), after which the viral count is still below the MIC for extended periods, such as about two or three additional days. Inhibitory activity against influenza virus was observed for up to 48 hours.

In the event that the treated surface is touched by a mammal, some of the coating composition may be transferred to the mammal and encounter a disrupted skin or other body surface. Traces of active microorganisms may be present on the transferred coating composition or may be picked up from elsewhere and come into contact with the transferred coating composition. In this situation, without being bound to theory, certain embodiments of the still-active coating composition are expected to have additional antimicrobial preventative activity on the disrupted skin or body surface site. In an embodiment that illustrates a proposed mechanism of the composition in such a case, shown in FIG. 1B, the composition provides anti-viral activity. When a virus (or other microorganism) comes into contact with a cell, it will bind to receptors on the host cell. Over time, 5 to 6 hours, or so, the virus is internalized by the host cell, the virus multiplies inside the host cell, and it induces cell lysis causing additional virus particles to infect other host cells. In contrast, in a disrupted skin or other body surface that has come into contact with embodiments of the coating composition, a protective coating is on the surface of the host cell. The coating, may protect the cell and any receptors on the cell, thereby preventing the virus particle from binding to the cell receptors. Thus, infection and lysis is also prevented. Similarly, the disrupted skin or mucosal surface, or a mucosal surface is also protected from bacteria or fungi.

The coating composition retains the barrier coating for a long duration, such as a duration of about 1 hour, about 2 hours, or more, a duration of about 6 hours or more, a duration of about 16 hours or more, a duration of about 16 hours to about 24 hours, or a duration of about 24 hours or more, thereby protecting host cells and preventing infection. The cidal or static antimicrobial activity is also retained for a long duration, such as about 1 hour or more, about 2 hours or more, about 6 hours or more, about 16 hours or more, about 24 hours or more, or about 48 hours or more, thereby killing microorganisms before they can be transferred to mammals and even if transferred to mammals continuing to protect host cells and preventing infection. These durations are applicable for viruses, bacteria, and fungi.

In another embodiment, the coating composition is applied on an item or apparatus surface prior to the item or apparatus surface encountering a contaminated environment and prior to the apparatus encountering an internal body surface of a mammal. The coating composition provides a barrier coating on the item or apparatus surface that traps and kills the microorganisms, thereby preventing or inhibiting active microorganisms from causing infection.

Harmful microorganisms are those known to cause infectious disease such as, for example, the treatment and prevention of infectious diseases, such as communicable diseases caused by microorganisms, such as *Candida* species (e.g. *C. albicans, C. glabrata, C. krusei, C. tropicalis*), *Staphylococcus* species (including methicillin-resistant *S. aureus*, MRSA), *Streptococcus* species (e.g. *S. sanguis, S. oralis, S. mitis, S. salivarius, S. gordonii, S. pneumoniae*), *Acinetobacter baumannii, Aggregatibacter actinomycetemcomitans, Fusobacterium nucleatum*, and other microorganisms such as microorganisms that cause upper respiratory infections, and common cold (rhinovirus) and influenza viruses and Pneumonia, *P. gingivalis, Y. enterocolitica, Acinetobacter baumanii, Acinetobacter calcoaceticus, Aggregatibacter actinomycetemcomitans*, microorganisms that cause odor, microorganisms that can detract from visual appeal of surfaces, *Clostridium difficile, Bordetella pertussis, Burkholderia, Aspergillus fumigatus, Penicillium* spp, *Cladosporium, Klebsiella pneumoniae, Salmonella choleraesuis, Escherichia coli* (O157:H7), *Trichophyton mentagrophytes*, Rhinovirus Type 39, Respiratory Syncytial Virus, Poliovirus Type 1, Rotavirus Wa, Influenza A Virus, Herpes Simplex Virus Types 1 & 2, Hepatitis A Virus, Influenza B Virus, microorganisms that cause lower respiratory infections, Avian influenza virus, polio virus type 1, feline Calicivirus (Norovirus), *Salmonella, Escherichia coli* listeria, *Enterococcus faecalis, Enterobacter aerogenes, Aspergillus niger, Penicillium chrysogenum*, and *Staphylococcus epidermidis, Acinetobacter calcoaceticus, Pseudomonas fluorescens, Citrobacter* spp.

In an embodiment, the coating composition and method of treatment and prevention described herein may be useful, for example, for prevention of sexually transmitted diseases such as, for example, infections caused by human immunodeficiency virus (HIV), Herpes simplex, or human papilloma virus (HPV).

The coating composition has shown effectiveness against microorganisms with a diameter of, for example, about 30 nm or greater, such as about 100 nm (HIV, spherical), about 100 to about 300 nm (influenza, spherical and elongated forms), about 120 nm to about 260 nm (EBV spherical/disk forms), and about 30 nm (rhinovirus, spherical). Thus, the coating composition should also be effective against other microorganisms with diameters of about 30 nm, or greater than about 30 nm.

The coating composition has even shown powerful and surprising activity inhibiting biofilms, which can be very difficult to eradicate. In an embodiment, the method comprises administering the coating composition to a formed biofilm on a surface or inhibiting microorganisms encountered by the coating from forming a biofilm.

In an embodiment, the coating composition and method of treatment and prevention described herein may be useful, for example, for prevention and/or treatment of odors emanating from microorganisms present on or growing on any of the surfaces mentioned above.

In an embodiment, the coating composition and method of treatment and prevention described herein may be useful, for example, for the prevention and/or treatment of odors from microorganisms deposited on kitchen or bathroom surfaces, or any other surfaces mentioned herein. For example, the coating composition may be used to prevent odor from bacteria deposited during food preparation, from spills of food or drink or bodily fluids on carpet or vehicle interiors, or any number of other occurrences where odor causing microorganisms are deposited or grow on surfaces.

Odor causing microorganisms include, for example, bacteria and fungi. Specific examples that may be mentioned, include, *Centipeda periodontii, Eikenella corrodens,* Enterobacteriaceae, *Fusobacterium nucleatum* subsp. *nucleatum, Fusobacterium nucleatum* subsp. *polymorphum, Fusobacterium nucleatum* subsp. *vincentii, Fusobacterium periodonticum, Porphyromonas endodontalis, Porphyromonas gingivalis, Prevotella (Bacteroides) melaninogenica, Prevotella intermedia, Bacteroides (Bacteroides) loescheii, Solobacterium moorei,* Tannerella forsythia (*Bacteroides forsythus*), *Treponema denticola,* such as those disclosed in Scully, C. and J. Greenman (2008). "Halitosis (breath odor) ." Periodontol 2000 48: 66-75, which is hereby incorporated by reference. Odor causing microorganisms may also be considered harmful microorganisms for purposes of this application.

In an embodiment, the coating composition and method of treatment and prevention described herein may be useful, for example, for treatment and prevention of detraction of the visual aesthetic appearance of surfaces. Such detraction of the visual aesthetic appearance of a surface may be caused by microorganisms that produce a visible growth on a surface and/or discoloration of a surface. In an embodiment, the coating composition and method of treatment and prevention described herein may be useful, for example, for prevention and/or treatment of staining of tile grout by mold, or prevention and/or treatment of basement floor or wall surfaces.

Microorganisms that cause detraction of the visual aesthetic appearance of surfaces include, for example, fungi. Microorganisms that cause detraction of the visual aesthetic appearance of surfaces may also be considered harmful microorganisms for purposes of this application.

The microorganisms may be air-borne microorganisms. In an embodiment, the microorganisms are those that cause communicable diseases. In an embodiment, the microorganisms do not include those that cause allergic reactions or dental problems, such as, for example, cavities (caries), gingivitis, or seasonal allergies. Similarly, in an embodiment, the method of prevention does not solely or additionally prevent dental problems or allergic reactions, such as, for example, cavities (caries), gingivitis, or seasonal allergies.

In another embodiment, however, microorganisms, such as fungi that may generally be classified as allergens, other allergens, and airborne irritants to the body, are trapped by the barrier coating and the method. It may be especially useful to treat surfaces with the coating composition if an allergic mammal is expected to be in a location known or expected to produce a high number of allergens or airborne irritants, such as an outdoor environment.

The methods and compositions disclosed herein may be especially applicable for treating surfaces that immunocompromised persons will encounter. In addition, the coating composition may be useful for prevention and/or treatment of infections by microorganisms that commonly infect wounds on the skin or other body surface.

In an embodiment, the surface of a medical device is treated with the coating composition prior to contacting the human body. The coating composition provides a coating on the medical device surface that traps and kills microorganisms. Medical devices include, for example, instruments, apparatuses, and other articles of manufacture that are intended to contact or come in close proximity with the human body, such as human tissue, bloodstream, mucosa, open wounds, and surfaces in internal cavities. Examples of medical devices include ventilators, trachea devices, catheters, central venous catheters, urinary catheters, peritoneal dialysis catheters, contact lenses, total joint replacement prostheses, endotracheal tubes, voice prostheses, penile prostheses, testicular prostheses, prostatic stents, artificial urinary sphincters, breast prostheses, vascular graft, orthopedic devices, prosthetic heart valves, scalpels, scopes, implanted replacement devices, In an embodiment, medical devices also include dental devices.

In an embodiment, the medical device is treated with the coating composition prior to encountering the human body, such as up to about 12 hours prior to encountering the human body, for example, about 5 minutes to about 8 hours, about 12 minutes to about 6 hours, or about 1 hour to about 10 hours, prior to encountering the human body.

In an embodiment, the medical device is treated with the coating composition in a spray formulation by spraying the medical device until a moist coating appears on the surface. In another embodiment, the medical device is treated by dipping the medical device in the coating composition and withdrawing it from the composition, which results in a residual coating layer on the medical device.

In an embodiment, the medical device is a catheter or similar device that is inserted into a mammal body canal, such as the throat, the anal, vaginal, or urethral lumens. The coating is applied to the medical device prior to encountering the body canal and, as it is inserted, also helps to lubricate the body canal and provide antimicrobial activity along the canal.

In an embodiment, the medical device that contacts more than one location on the body, such as a catheter, scope or a device used in surgery. Treating a medical device such as a urinary tract catheter prior to the first contact with the body may reduce the risk of transferring infectious microorganisms from one area of the body to another.

In another embodiment, the method of treating a surface with the coating composition includes identifying a contaminated surface, wherein the contaminated surface is known or expected to be contaminated with harmful viral, fungal, or bacterial microorganisms.

In an embodiment, the step of applying the coating composition occurs prior to or during a mammal that is not contaminated encountering the contaminated surface. In an embodiment, the application of the coating composition occurs in response to the identification of the surface as being contaminated or in response to an observation of a contamination event. For example, the coating composition may be applied to a surface where a contamination event has occurred, such as when a person has sneezed, coughed, or vomited, or more generally where bodily fluids or matter have been deposited.

In another embodiment, the method of treating a surface with the coating composition includes identifying a contaminated surface, wherein the contaminated surface is known or expected to be contaminated with odor causing viral, fungal, or bacterial microorganisms. The step of applying the coating composition occurs prior to or during an odor emanating from the contaminated surface.

In an embodiment, a method includes preventing or decreasing odor produced by microorganisms, by performing the steps of applying a coating composition that comprises an antimicrobial onto an inanimate surface. The coating composition then quickly forms a coating layer on the inanimate surface that is active to trap, and kill or neutralize microorganisms encountered by the coating layer for a duration of at least about one hour, thereby preventing or decreasing odor generated by microorganisms from escaping the barrier layer. The microorganisms that encounter the coating layer may be those that were already present on the surface that was treated or those that are disposed on the exposed top surface of the coating layer after it is applied. In an embodiment, the method includes identifying an area of the inanimate surface that is a source of the odor, and applying the coating composition to the area.

In another embodiment the method of treating a surface with the coating composition includes identifying a contaminated surface, wherein the contaminated surface is known or expected to be contaminated with viral, fungal, or bacterial microorganisms that cause detraction of the visual aesthetic appearance of surfaces. The step of applying the coating composition occurs prior to, during, or after a detraction of the visual aesthetic appearance of the contaminated surface occurs. For example, the coating composition may be applied to bathroom tile grout that show visual signs of mold growth or are expected to come in contact with mold, or on other surfaces mentioned herein that show visual signs of mold growth or are expected to come in contact with mold.

In an embodiment the method includes preventing or treating a detraction of a visual appearance of a surface, where the detraction is caused by microorganisms that produce a visible growth on the surface or discoloration of the surface. The treatment or prevention is facilitated by the steps of applying a coating composition that comprises an antimicrobial onto the surface; forming a coating layer on the surface that is active to trap, and kill or neutralize microorganisms encountered by the coating layer for a duration of at least about one hour, thereby preventing or decreasing the visible growth or discoloration on the surface. The microorganisms that encounter the coating layer may be those that were already present on the surface that was treated or those that are disposed on the exposed top surface of the coating layer after it is applied. In an embodiment, the method includes identifying an area of the surface that has a visible microbial growth or discoloration, and applying the coating composition to the area.

In another embodiment, the method of treating a surface with the coating composition includes treating the surface with the coating composition proactively, regardless of whether the surface is known or expected to be contaminated with viral, fungal, or bacterial microorganisms. In an embodiment, the administered coating traps and kills microorganisms that encounter the coating after the treating step. As disclosed herein, the coating is effective to kill microorganisms encountered for a long duration after the treatment step, thereby facilitating its effectiveness as a proactive treatment, which stands in contrast to prior art antimicrobial compositions that are not effective for proactive treatment, partly due to their ineffectiveness for long time-periods.

To achieve full effectiveness, the proper amount to apply to a surface is an amount that is enough to coat the targeted surface with enough of the coating composition to form a coating layer, for example, this may be determined by whether the surface appears wet or misted. For example, in certain embodiments, the effective amount may be expressed in terms of a volume per square cm, such as, for example, from about 0.5 to about 50 μl/cm², such as, about 5 to about 40 μl/cm², or about 10 to about 25 μl/cm²; or for example, about 0.625 to about 10 μl/cm², such as, about 2.5 to about 5 μl/cm². Other delivery mediums, such as a roll-on or disposable wipes, may have dosages derived from these ranges given the adjustments for concentrations and other factors known to those of skill in the art. In a low tack embodiment, the coating composition may provide more surface coverage per volume. In a low tack embodiment, the coating layer may covers an area of approximately 50,000 mm² to about 1,000 mm² per microliter of composition, such as, for example, about 30,000 mm² to about 10,000 mm², or about 5,000 mm² to about 2,000 mm².

In an embodiment, in a continued application method of prevention and/or treatment, the coating forming composition may be administered to a surface in a series of doses, such as, for example, about every 1 to 2 days, about every 2 to 4 days, or about every 1 to 2 weeks. This method of prevention and/or treatment can be continued, for example, for 6 to 12 months or for several years. This continued application method may be preferred during flu season or outbreaks of particular illnesses, or simply as part of a routine cleaning schedule.

In an embodiment, methods of applying the coating composition include, for example, dipping, instilling, rubbing, mopping, wiping, or spraying the composition onto the surface. The coating composition may be applied to the surface through many different delivery systems, including, for example: dilutable liquids, gels, lubricants, compositions sprayable by a mechanical action pump, aerosolized spray compositions, or infusion or layering of the coating composition into or onto products, such as disposable wipes for coating the surface.

In an embodiment, the coating composition is sprayed onto a surface in an amount sufficient to coat the surface with a mist or thin layer of liquid. One or more sprays may be required to coat the surface depending on the size of the surface. Areas that are considered especially contaminated with microorganisms may be treated more heavily than others. Wiping or rubbing is not required in this embodiment.

A mechanical pump spray or an aerosolized spray device may be used. In the aerosolized embodiment, the coating composition may be mixed with common propellant agents, such as CO₂, nitrogen, and hydrocarbons. A bag-on-valve embodiment may also be used; however, the composition is stable enough so as not to require a separation of the propellant agent and the composition components.

In an embodiment, the coating composition is applied by wiping the composition onto the surface from a material that includes the coating composition. For example, a cloth, a mop, a scrubbing brush, a toilet cleaning brush, or a paper towel, may be at least partially saturated with the coating composition. The composition may then be wiped or mopped or otherwise applied to the surface from the material. In an embodiment, the composition can be applied by spraying and subsequent wiping of the sprayed composition.

In a particular embodiment, a disposable wipe is pre-treated with the coating composition. In an embodiment, the wipe can simply be removed from a container and then be rubbed on the desired surface to apply the coating composition to the surface. The wipe can then be disposed of. Common materials for disposable wipes include, for example, wood pulp, viscose, polyester, cotton, and combinations of these. The wipe can be soaked in and then removed from the coating composition for the pre-treatment step. The wipe should be at least partially saturated with the coating composition. In the application step, the surface should be wetted with the wipe to provide an effective barrier coating. After wiping the surface, a coating composition is deposited that forms a thin film barrier coating on the surface and is active to inhibit microorganisms that contact the barrier coating from escaping the barrier coating.

In an example, the disposable wipe may be used to treat an item, such as a urinary tract catheter, in order to apply the coating composition to the item.

Without being bound by theory, the same anti-viral barrier mechanism described above and depicted in FIG. 1B is applicable to the anti-bacterial, and anti-fungal activity of the composition and method of prevention described herein.

In an embodiment, the coating composition comprises a carbohydrate gum (C), a humectant (H), and an antimicrobial agent (A), and the coating composition meets the following requirements:

about $0.0001\% \leq C \leq$ about 0.4%;
about $0.07\% \leq H \leq$ about 70%; and
$0.0005\% < A$
or
about $0\% \leq C \leq$ about 0.4%;
about $55\% \leq H \leq$ about 70%; and
$0.0005\% < A$ All percentages are by weight of the total composition. The ranges in this embodiment reflect the demonstrated effectiveness of the germ killing power of the coating composition at very low dilutions against many microorganisms reported in MIC experiments in Table V below. After effective application, the barrier coating layer has antimicrobial cidal or static activity.

In another embodiment the coating composition meets the following requirements:

about $0.01\% \leq C \leq$ about 0.4%;
about $4.5\% \leq H \leq$ about 65%; and
$0.0005\% < A$
or
about $0\% \leq C \leq$ about 0.4%;
about $55\% \leq H \leq$ about 65%; and
$0.0005\% < A$ All percentages are by weight of the total composition.

In a low tack embodiment, the coating composition meets the following requirements:

about $0.07\% \leq H \leq$ about 10%; and
$0.0005\% < A$
wherein H is a humectant and A is an antimicrobial.

All percentages are by weight of the total composition.

In an embodiment, the concentration of the humectant may range about 3% to about 8%, 0.35% to less than 1%, or about 0.1% to less than 0.5%. In another embodiment, the humectant of the coating composition meets the following requirements: about $0.07\% \leq H \leq 1\%$. This low-humectant embodiment reduces the stickiness or adhesiveness of the composition to provide a better tactile sensation to the inanimate surface.

In a low tack embodiment, the coating composition is essentially free of carbohydrate gum, such as for example including less than 0.00009% carbohydrate gum, no detectable carbohydrate gum, or no carbohydrate gum. The term essentially free also include completely free.

The coating composition may comprise about 50% to about 98% by weight water, such as, for example, about 75% to about 97% water, or about 85% to about 95% water.

In an embodiment, the coating composition includes glycerin or one or more similar humectant substances. Humectants similar to glycerin may be classified generally as polyols. The humectants may be, for example, glycerin, sorbitol, xylitol, propylene glycol, polyethylene glycol, and mixtures thereof.

An antimicrobial agent is present in the composition. For example, the composition may include one or more anti-viral agents, or antifungals, or antibacterials or a combination thereof. In addition, the effect of such antimicrobials includes static and/or cidal activity. In an embodiment, the antimicrobial acts by binding to cell membranes of the microorganisms and disrupting them, thereby causing cell death.

In an embodiment, the coating composition is a broad spectrum antimicrobial, such as an antimicrobial classified as an antiseptic, or possesses activity against viruses, bacteria, and fungi. The antimicrobial agent may include, but is not limited to cationic antimicrobial agents and pharmaceutically acceptable salts thereof, including, for example, quaternary ammonium compounds, such as monoquaternary ammonium compounds (QAC, cetrimide, benzalkonium chloride, cetalkonium chloride, cetylpyridinium chloride, myristalkonium chloride, Polycide), biquaternaries and bis-biguanides (Chlorhexidine, Barquat, hibitane), and biguanides, polymeric biguanides, polyhexamethylene biguanides, Vantocil, Cosmocil, diamidines, halogen-releasing agents including chlorine- and iodine-based compounds, silver and antimicrobial compounds of silver, peracetic acid (PAA), silver sulfadiazine, phenols, bisphenols, hydrogen peroxide, hexachloroprene, halophenols, including but not limited to chloroxylenol (4-chloro-3,5-dimethylphenol; p-chloro-m-xylenol).

In addition, the antimicrobial may also be or include: antibacterial agents, both cidal and static, and different classes, for example tetracycline, chloramphenicol, fusidic acid, fluoroquinolone, macrolide antibacterial agents, oxazolidinones, quinolone- and naphthyridone-carboxylic acid, citral, trimethoprim and sulfamethoxazole (singly and combined), aminoglycoside, polymyxin, penicillins and their derivatives. In addition, the antimicrobial may also include, for example: antifungal agents in the following classes: azoles, polyenes, echinocandins, and pyrimidines. Combinations of the any of the foregoing antimicrobial agents are also contemplated. Many of the foregoing are cationic species or their pharmaceutically acceptable salts, and in an embodiment, cationic antimicrobials are utilized in the composition. In an embodiment the composition is exclusive agents that release gas fumes, such as, for example, chlorine dioxide, or chlorine dioxide producing reactants.

In an embodiment, the coating composition does not induce mutations or the development of resistance by microbes. This is because of the mechanism of action against the microorganisms by the coating and the selected antimicrobial.

The antimicrobial may be present, for example, in an amount ranging from about 0.0005% to 5% by weight of the total composition, such as, for example, about 0.0025% to about 1%, about 0.005 to about 0.006%, or about 0.0006% to about 0.003%. In another embodiment, the antimicrobial may be present, for example, in an amount ranging from about 0.05% to about 0.1% by weight of the total composition, such as, for example, about 0.05% to about 0.06% or about 0.06% to about 0.1%. In an embodiment, the antimicrobial is about 5% or less, or about 3% or less, or about 1.5% or less, such as when the antimicrobial used does not cause solubility problems at higher concentrations.

In a low-tack embodiment, the coating composition used in a method of treating an inanimate surface includes 0.0005% to 5% by weight of a monoquaternary ammonium compound or a pharmaceutically acceptable salt thereof. In such an embodiment, the coating composition may consist essentially of the monoquaternary ammonium compound or a pharmaceutically acceptable salt thereof.

In an embodiment, the composition consists essentially of only the humectant and the antimicrobial, such as, additionally including only preservatives, scenting agents, or other agents, that do not affect the trapping or antimicrobial activity of the composition. "Consists essentially of" or "consisting essentially of" as used herein has the meaning that is typically applied, that is, it means, the specified materials and those that do not materially affect the basic and novel characteristic(s) of the composition.

In embodiments, the composition may further include components, such as, for example, copovidone and other lubricating agents, parabens such as methyl paraben or propylparaben, scenting agents, preservatives, such as sodium benzoate, buffering agents, such as monosodium and disodium phosphate, sweeteners, hydrogenated castor oil with ethylene oxide, and carboxymethylcellulose. These components may, for example, be included in amounts ranging from about 0.01% to about 5% by weight of the total composition, such as, for example, about 0.1% to about 2%. In another embodiment, the components are included, for example, in amounts of about 0.0001% to about 0.05%. Buffering agents (such as monosodium or disodium phosphate) may also be used.

Purified water, and/or, in less preferred embodiments, alcohol, may be used as the diluent component of the composition. In an embodiment, the coating composition is a free-flowing liquid suitable for spraying. This is in contrast to a paste or toothpaste composition, which is typically not free-flowing and not suitable for spraying. In addition, in an embodiment, the coating composition is free of abrasives that are commonly used in toothpaste compositions.

In an embodiment, substantially free-flowing and substantially free of clumps is judged by passing the composition through a 140 U.S. mesh (0.10 mm pore size), and 95 to 100% of the composition, such as 96% to 99.9% passes through, after 30 seconds.

Some antimicrobials, including cetylpyridinium chloride, are known to be negatively affected in their antimicrobial properties by additional active components. Thus, in an embodiment, the composition consists essentially of only the gum, the humectant, and the antimicrobial, such as, for example including only additional preservatives, scenting agents, or other agents that do not materially affect the antimicrobial activity. In an embodiment, the composition is exclusive of agents for acting against the teeth and/or gums, including, for example, abrasives (such as those used in toothpastes) teeth whitening or desensitizing agents. In an embodiment, the composition is exclusive of cellooligosaccharides. In an embodiment, the antimicrobial agent is exclusive of lipids such as fatty acid ethers or esters of polyhydric alcohols or alkoxylated derivatives thereof. In an embodiment, the composition is exclusive of one or more of time-release agents, allergy-relief compounds, azelastine, silicon based oils, essential oils, polyvinyl pyrrolidone, polyvinyl alcohol, and potassium nitrate. In an embodiment, the composition is free of volatile organic compounds, including for example, volatile alcohols. In an embodiment, the composition is free of surfactant or foaming agent. For the avoidance of doubt, none of the above should be construed to mean that all embodiments are exclusive of these compounds.

In an embodiment the coating composition is non-flammable.

In an embodiment, a method for making a coating composition includes mixing and heating the antimicrobial agent with other components, such as the humectant and carbohydrate gum. In an embodiment, heating is replaced with extended mixing times. Other components may also be mixed in a single or multiple mixing steps. All components of the coating composition may be mixed at one time to produce a composition with a stable shelf life, such as, for example, being stable for over about 6 months, such as stable for about 1 year to about 3 years, or about 1.3 to about 2 years. This is in contrast to compositions that have active components that must be added separately a short time prior to use, or those that will separate out of solution. Thus, in an embodiment, the coating composition is a stable one-part composition that does not require mixing with a second composition to activate it for use. In an embodiment, the coating composition is in a single phase and is not an emulsion.

In an embodiment, the composition is a free-flowing liquid and is non-foaming.

In general, the dual-action mechanism of providing a barrier coating from microorganisms and an antimicrobial agent provides a long-lasting effect, characterized by both in vitro, simulated in vivo, and in vivo examples below. In in vivo examples the coating composition was shown to have antimicrobial effect (cidal or static) for at least 6 hours. In addition, in vitro tests indicate the antimicrobial effect had a significantly extended duration past about 2 hours, past about 6 hours, and depending on the microorganism tested, such as greater than about 8 hours, about 6 to about 16 hours, and about 24 hours, or more.

Post antimicrobial effect (PAE) is defined as suppression of microbial growth that persists after limited exposure to an antimicrobial agent. Having a longer PAE is considered advantageous for antimicrobial agents as it allows for persistent inhibition of microbial growth, and may affect dosing regimens as agents with long PAEs may need less frequent administration than those with short PAEs.

In embodiments of the method and composition disclosed herein the PAE of the composition when applied to a mucosa has a PAE that persists for about 6 hours or more, such as about 6 hours to about 16 hours, or about 16 hours to about 24 hours.

As mentioned above, in an embodiment, the composition is suitable for spraying, and thus also has a viscosity that is suitable for spraying. In an embodiment, the composition has a viscosity of less than 500 cps such as, for example, about 490 cps to about 10 cps, or about 400 cps to about 15 cps. In another embodiment, the composition has a viscosity of about 16 to about 20 cps, such as, for example, about 17 to about 19 cps.

Without being bound by theory, the coating composition is not hydrophilic which allows the composition to have a greater affinity to adhere to and cover certain surfaces. Furthermore, in an embodiment, the antimicrobial being embedded in the non-hydrophilic composition will allow for sustained antimicrobial activity on treated surfaces. In an embodiment the coating composition is amphiphilic or has amphiphilic components.

One measure of hydrophilicity is the Rf (relative front) value, determined by chromatography in water. In an embodiment, the composition has an Rf value in water of 0 to about 0.25, such as about 0.0001 to about 0.15, or about 0.03 to about 0.1.

In an embodiment, the composition has a pH of about 4 to about 8, such as about 5 to about 7, or about 6 to about 7.5. In another embodiment the composition has a pH of greater than 5.5 to about 8, wherein antimicrobials such as cetylpyridinium chloride are most effective.

Several experiments were performed to assess the safety of the composition on mammals and the ability of the spray formulation to form a protective barrier coating on an Engineered Human Oral Mucosa (EHOM) model. The experimental evidence showed that the composition formed a barrier coating over tissues, which prevents microorganisms from penetrating into the tissues

EXAMPLES

Example 1

Human Gingival Epithelial Cell and Fibroblast Cultures

Examples 3-9

Examples of the coating compositions were created by adding the ingredients listed below in a 50-ml centrifuge tube, and vortexing to bring to "free-flow" consistency. The constituents of the compositions and their approximate amounts are given in Table I (the values in Table I are percentages by weight of the total composition):

TABLE 1

| | Example 3 | Example 4 | Example 5 (control) | Example 6 (control) | Example 7 | Example 8 | Example 9 |
|---|---|---|---|---|---|---|---|
| Glycerin | 7 | 35 | 35 | 35 | 35 | 7 | 7 |
| Xanthan Gum | 0.01 | 0.4 | 0.4 | 0.4 | 0.4 | 0.01 | 0.01 |
| Cetyl Pyridinium Chloride | 0.05 | 0.05 | | | 0.1 | 0.06 | 0.05 |
| Preservatives | No | No | No | Yes | Yes | Yes | Yes |

*Purified water comprised the remaining portion of the composition.
**Preservatives included methylparaben (0.1%), propylparaben (0.1%), sodium benzoate (0.5%)

Normal human gingival cells (epithelial cells and fibroblasts) were obtained from ScienCell Research Laboratories (Carlsbad, CA, USA). The fibroblasts were cultured in Dulbecco's modified Eagle's medium (DME, Invitrogen Life Technologies, Burlington, ON, Canada) supplemented with fetal bovine serum (FBS, Gibco, Burlington, ON, Canada) to a final concentration of 10%. The epithelial cells were cultured in Dulbecco's modified Eagle's (DME)-Ham's F12 (3:1) (DMEH) with 5 µg/ml of human transferrin, 2 nM 3,3',5' of tri-iodo-L-thyronine.

0.4 µg/ml of hydrocortisone, 10 ng/ml of epidermal growth factor, penicillin and streptomycin, and 10% FBS (final concentration). The medium was changed once a day for epithelial cells and three times a week for fibroblasts. When the cultures reached 90% confluency, the cells were detached from the flasks using a 0.05% trypsin-0.1% ethylenediaminetetra acetic acid (EDTA) solution, washed twice, and resuspended in DMEM (for the fibroblasts) or DMEH-supplemented medium (for the epithelial cells).

Example 2

Engineered Human Oral Mucosa (EHOM) Tissue

The EHOM model was produced by using the gingival fibroblasts and epithelial cells of Example 1 that were used to form a complex three-dimensional spatial cellular organization similar to that found in normal human oral mucosa. The lamina propria was produced by mixing Type I collagen (Gibco-Invitrogen, Burlington, ON, Canada) with gingival fibroblasts, followed by culture in 10% FBS-supplemented medium for four days. The lamina propria was then seeded with gingival epithelial cells to obtain the EHOM. The tissue specimens were grown under submerged conditions until the total surface of the lamina propria was covered with epithelial cells. To produce stratified epithelium, the EHOM was raised to an air-liquid interface for four more days to facilitate the organization of the epithelium into its different strata.

Figure 2:
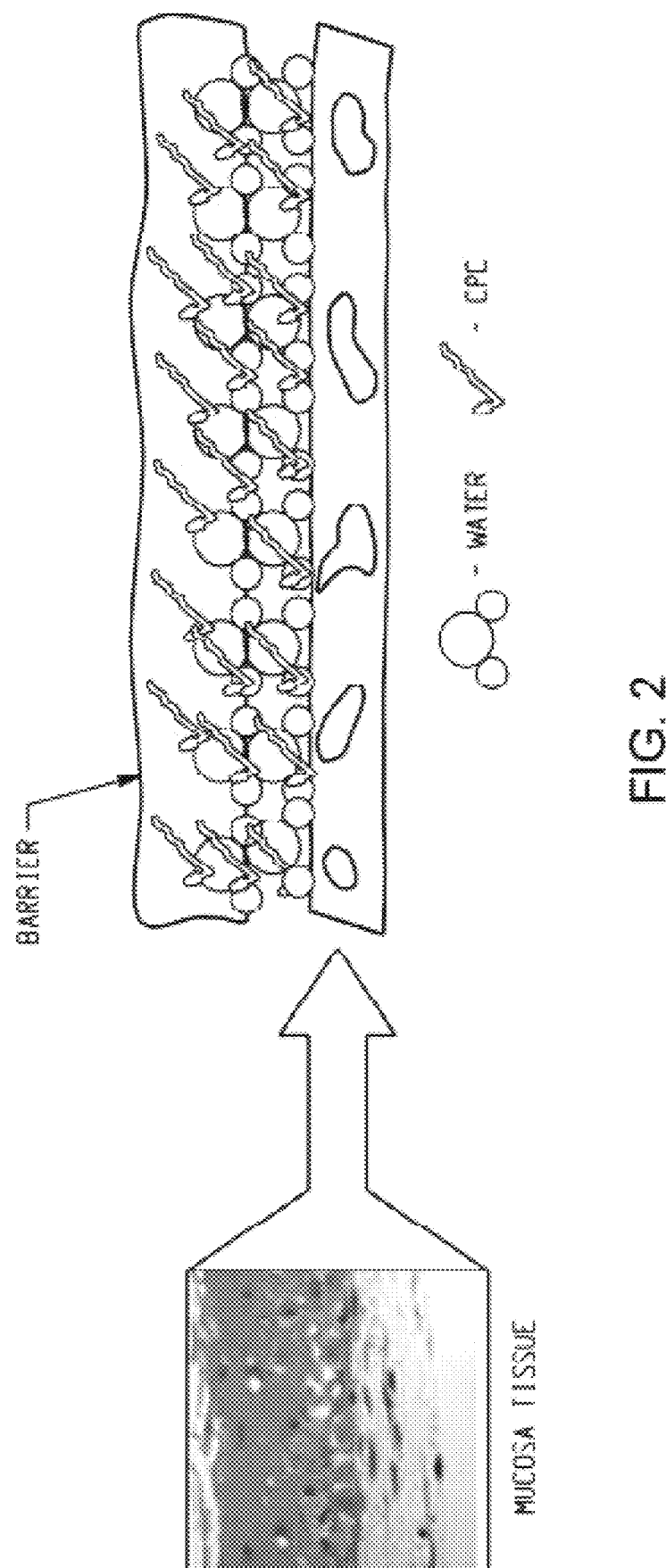
FIG. 2 is a schematic showing the formation of a barrier on a mucosal surface, as described in Example 2.

The lamina propria is a thin layer of loose connective tissue that lies beneath the epithelium and together with the epithelium constitutes the mucosa. FIG. 2 shows an illustration of the EHOM mucosal tissue, with an arrow pointing to its location in a schema depicting mucosa covered with the coating composition.

Based on the results below, the preservatives were found to be superfluous to the barrier coating formation and antimicrobial activity.

Examples 10-26

Examples 10-26 were performed to demonstrate safety of the composition on mucosal surfaces. Prior patent publication U.S. 2012/0270909, incorporated herein by reference includes this information.

Examples 27 and 28

Determination Whether the Coating Composition Affects Mechanical Barrier Function of EHOM Against Microbial Passage Through Mucosal Tissue.

In Examples 27 and 28, two approaches were used to determine whether the control Examples formed a barrier coating that blocked the microbial passage through the mucosal tissues and also had an inherent anti-microbial effect. Growth in pass-through chamber and growth on EHOM surface was assessed by evaluating growth in agar media.

In Example 27, EHOMs of Example 2 were put in contact with 1 and 5% dilutions (diluted in serum free culture medium) of Example 4 for 2 minutes. Tissues were then washed twice with serum free culture medium then over layered with $1 \times 10^6$ Candida microbial cells in a volume of 300 µl. Tissues were then put on air-liquid culture plates and incubated for 24 hours in 5% $CO_2$ humid atmosphere at 37° C. Next, the culture medium underneath the EHOM (ventral chamber) was collected and seeded on Sabouraud agar plate to verify whether or not the microorganisms penetrated through the tissue and reached the culture medium below. A culture was also obtained from the EHOM surface and seeded on Sabouraud agar plate. The process is graphically depicted in FIG. 3.

In Example 28, EHOMs of Example 2 that were treated with 1 and 5% dilutions of the Example 4 composition for 2 minutes were over layered with Candida microbial cells for 24 hours were flipped onto Sabouraud dextrose agar plates and left in place for 5 minutes. The EHOMs were then removed and the plates were incubated for 24 hours at 30° C., after which microbial growth was ascertained macroscopically and photographed. Each experiment was repeated 5 independent times with similar results.

Figure 4:
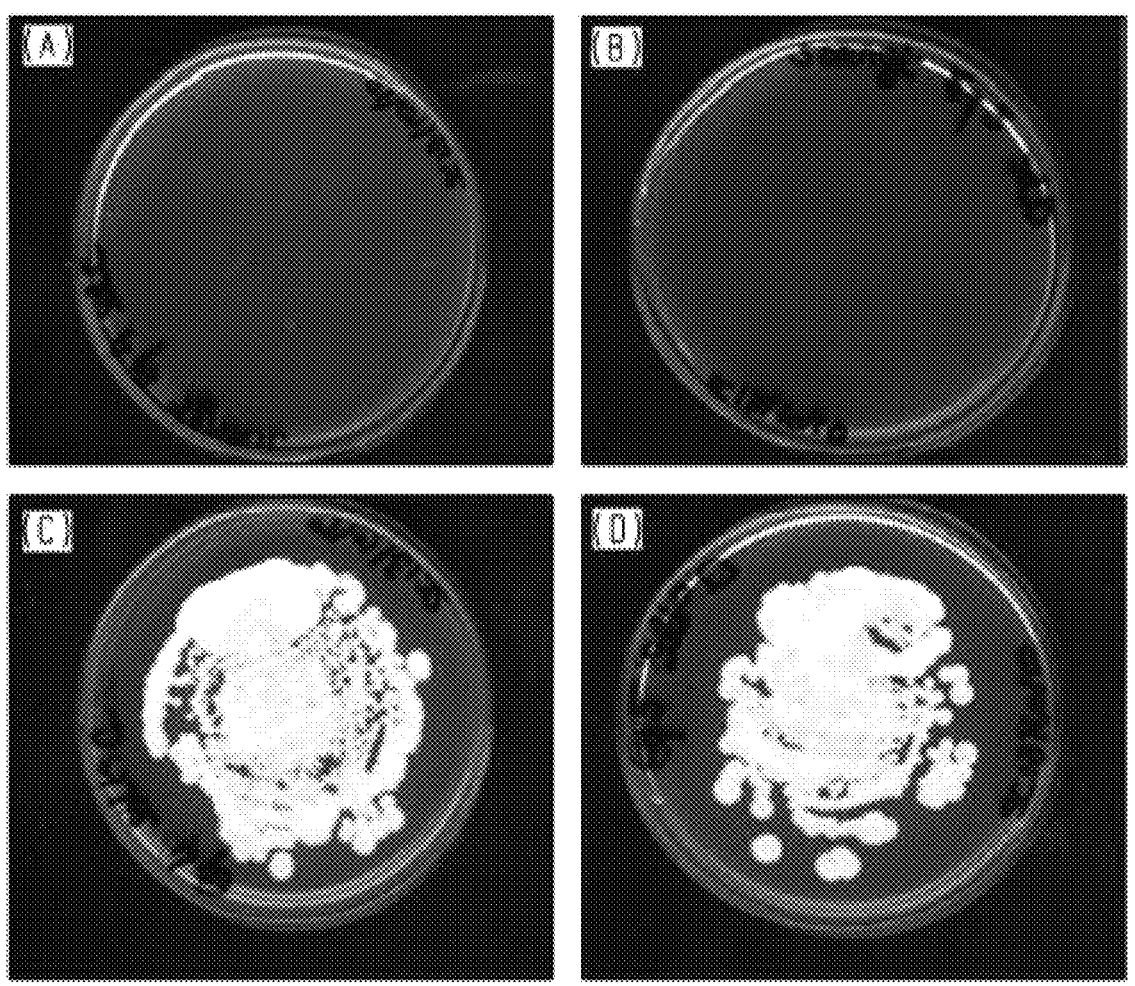
FIG. 4 show photographs of agar media plates showing microbial growth in the upper and lower chambers of an EHOM assay, as described in Examples 27-28.

FIG. 4 shows the results of the cultures of the EHOM surface (panels C and D) and the culture of the pass-through liquid from the bottom (ventral) chamber (panels A and B). The A and C panels were EHOMs treated with a 1% dilution of Example 4, and the B and D panels were EHOMS treated with a 5% dilution of Example 4. This data indicates that Example 4 composition forms a barrier coating that prevents passage of microbes through the EHOM tissues but does not have an inherent anti-microbial effect.

Examples 29 and 30

In Examples 29 and 30, Examples 27 and 28 were repeated, except the EHOM were infected with *S. mutans*. Similar results were obtained that indicated that the coating compositions formed a barrier coating preventing the *S. mutans* microbes from passing through the barrier coating, but did not have an antimicrobial effect.

Examples 31 and 32

Determination Whether the Coating Composition Affects Mechanical Barrier Function of EHOM Against Microbial Invasion.

In Example 32, a set of EHOM tissues from Example 2 was treated with the coating composition of Example 4 and then overlaid with *C. albicans*. In control Example 31 a control set was not treated with the coating composition prior to overlayering with *C. albicans*. Immediately after each contact period, biopsies were taken from each EHOM, fixed with paraformaldehyde solution, and embedded in paraffin. Thin sections (4 μm) were stained with eosin-hematoxylin. Sections were observed using an optical microscope to analyze the invasion/penetration of microbial cells into the tissue. Following microscopic observations, representative photos were taken from each condition and presented. The experiment was repeated three times with similar results. Similar results were also obtained with treatment with Example 3 (data not shown).

FIG. 5 shows the effect of the coating composition on microbial invasion of EHOM tissues. Panel (A) is a representative photograph of the untreated control Example 31, and panel (B) is a photograph of the treated Example 32. The arrow indicates invading fungal hyphae in the untreated control Example 31.

Examples 33-40

The EHOM model described above was also used to evaluate the ability of Examples 5-7 to form a barrier coating that: (a) prevents oral bacteria (*S. mutans*) and fungi (*Candida albicans*) from penetrating/invading human oral mucosa, and (b) does not cause damage to host cells (cytotoxicity assay).

Examples 33-40 were formulated according to Table II below.

TABLE II

| | Coating composition Pre-Treatment | Microbe Overlay | FIG. reference |
|---|---|---|---|
| Example 33 | None | *C. albicans* | FIG. 6(A) |
| Example 34 | Example 5 | *C. albicans* | FIG. 6(B) |
| Example 35 | Example 6 | *C. albicans* | FIG. 6(C) |

TABLE II-continued

| | Coating composition Pre-Treatment | Microbe Overlay | FIG. reference |
|---|---|---|---|
| Example 36 | Example 7 | *C. albicans* | FIG. 6(D) |
| Example 37 | None | *S. mutans* | FIG. 7(A) |
| Example 38 | Example 5 | *S. mutans* | FIG. 7(B) |
| Example 39 | Example 6 | *S. mutans* | FIG. 7(C) |
| Example 40 | Example 7 | *S. mutans* | FIG. 7(D) |

In Examples 33-40, after pre-treatment and incubation according to the procedures of Examples 27 and 28: (1) the flow-through medium was collected from the lower chamber; and (2) tissues were flipped and placed onto the surface of Sabouraud dextrose agar Petri dishes, and incubated for 24 hours. Collected flow-through media were spread onto agar media plates, and incubated for 24 hours also as described in Examples 27 and 28. Table II also indicates the figure in which a photo of each Example was taken showing the microbial growth on each flipped Example culture.

Figure 6:
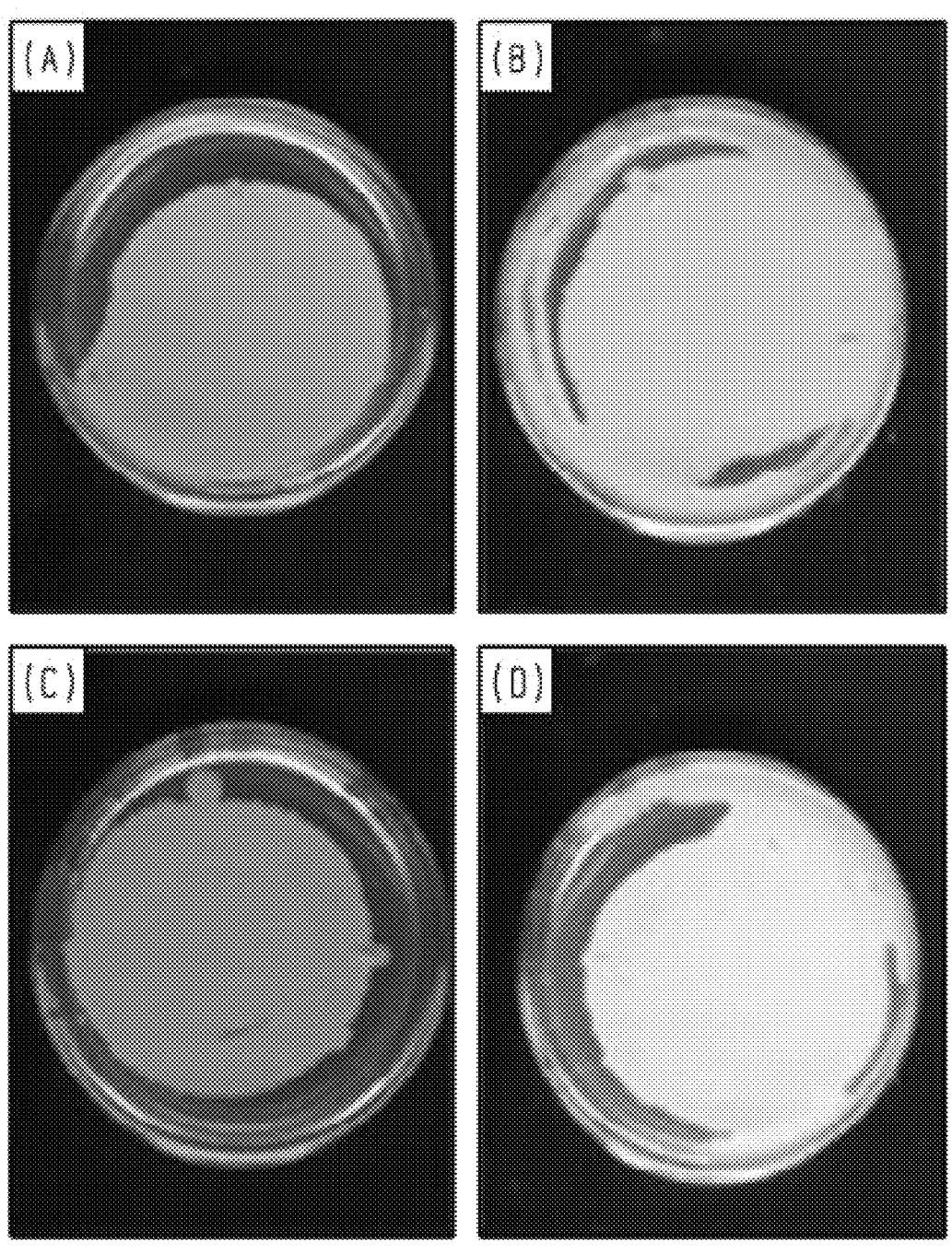
FIG. 6 shows photographs of microbial growth on untreated EHOM or EHOM treated with an example coating composition, followed by infection with *C. albicans*, as described in Examples 33-40.
Figure 7:
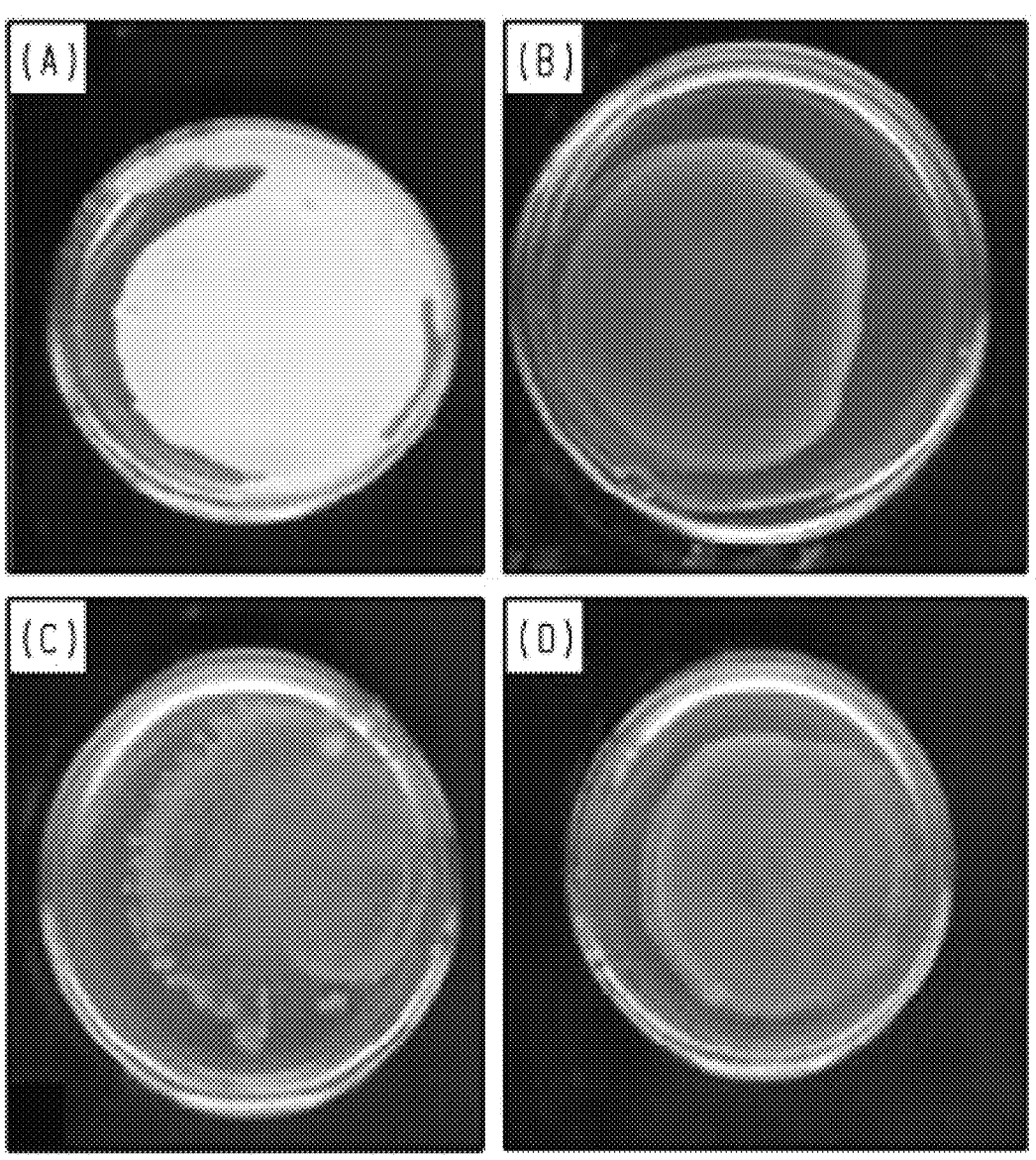
FIG. 7 shows photographs of microbial growth on untreated EHOM or EHOM treated with formulations followed by infection with *S. mutans*, as described in Examples 33-40.
Figure 8:
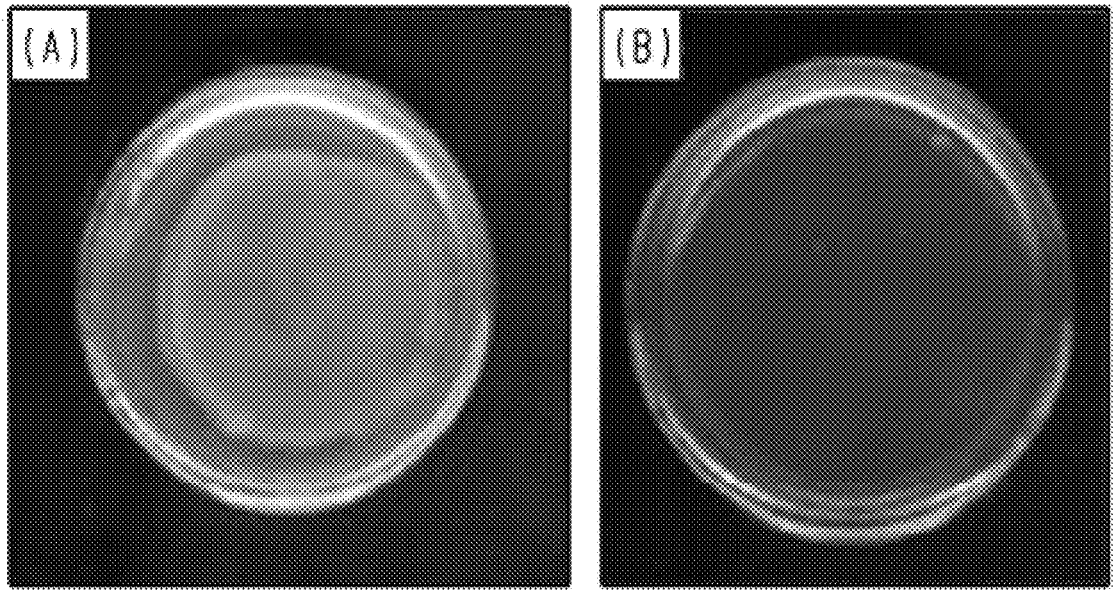
FIG. 8 shows photographs of microbial growth from "flow-through" media (collected from the lower chamber) of EHOM treated with an example coating composition, as described in Example 33-40.

FIGS. 6 and 7 show that both *Candida* and *Streptococcus* were able to grow on the surface of EHOM treated with the compositions of Examples 5-6. In contrast, as shown in FIG. 8, no microbial growth was observed when the "flow-through" medium collected from the lower chambers of EHOMs of Examples 36 or 40, i.e. those treated with the Example 7 composition. This indicates that treatment of the EHOMs with the Example 7 composition did not cause damage to the surface of the mucosal tissues and organisms were unable to penetrate the treated EHOM. Similar results were obtained with EHOM treated with the compositions of Examples 5 and 6 (data not shown). These data indicate that the combination of glycerine and xanthan gum is capable of forming a protective barrier coating on mucosal tissues.

Examples 41-47

Tested Formulations are not Toxic and do not Cause Damage to the Cells/Tissues

In Examples 41-47, the EHOM model was used to assess the toxicity of the composition. Examples 41-47 were formulated as stated in Table III.

TABLE III

| | Coating composition Pre-Treatment | Microbe Overlay | FIG. Reference |
|---|---|---|---|
| Example 41 | None | *C. albicans* | FIG. 9(A) |
| Example 42 | Example 5 | *C. albicans* | FIG. 9(A) |
| Example 43 | Example 6 | *C. albicans* | FIG. 9(A) |
| Example 44 | Example 7 | *C. albicans* | FIG. 9(A) |
| Example 41A | None | *S. mutans* | FIG. 9(B) |
| Example 45 | Example 5 | *S. mutans* | FIG. 9(B) |
| Example 46 | Example 6 | *S. mutans* | FIG. 9(B) |
| Example 47 | Example 7 | *S. mutans* | FIG. 9(B) |

After pre-treatment and incubation according to the procedures of Examples 27 and 28, culture supernatant was collected from the Example 41-48 EHOM tissues and used to measure LDH activity.

Figure 9:
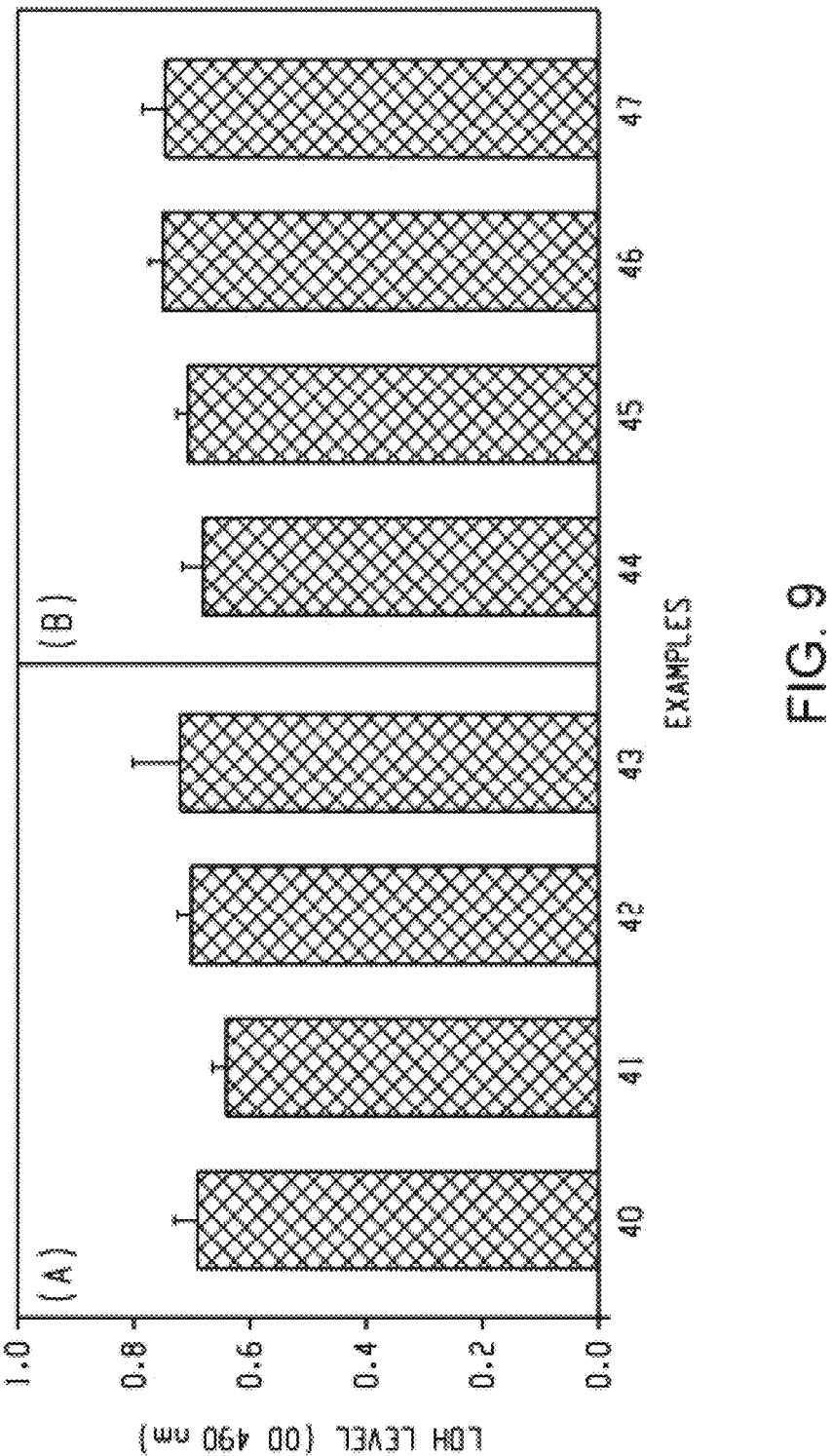
FIG. 9 presents graphs showing LDH release by EHOM treated with saline (control) or example coating compositions, followed by infection with (A) *C. albicans* or (B) *S. mutans*, as described in Examples 40-47.

As shown in FIG. 9, no significant increase in LDH levels was observed in Examples 41-48 irrespective of whether the formulations contained cetylpyridinium chloride with or without preservatives and infected with either *Candida albicans* or *S. mutans*, respectively. These data confirmed the non-toxic effect of the Example coating compositions and that these formulations maintained the integrity of the host mucosal tissues.

Data are mean±SD. No significant difference between untreated and treated tissues was noted.

Taken together, the data indicates that the example compositions represent an effective and a safe barrier that can prevent microorganisms from penetrating and invading human mucosal tissues.

Examples 48-61

Preclinical evaluation of the coating composition showed that the composition was effective against many bacteria and yeasts. The antimicrobial activities of the Example 7 coating composition were evaluated against a number of clinical isolates obtained from patients, including *S. salivarius, P. gingivalis, S. pyogenes, S. pneumonia, Fusobacterium nucleatum, S. mutans, S. aureus, Y. enterocolitica, S. oralis, S. mitis, C. albicans, C. krusei, C. tropicalis*, and *C. glabrata*. Activity of the Example 7 coating composition was evaluated by determining its minimum inhibitory concentration (MIC) using reference methods described in the Clinical and Laboratory Standards Institute (CLSI) documents M07-A8, M11-A7, and M27-A3.

A standardized inoculum of several types of aerobic or anaerobic bacteria ($1\times10^4$ cells/ml) was incubated with serially diluted solutions of Example 7 (containing 0.1% CPC, or 1 µg/ml) or 2% chlorhexidine gluconate (CHX, 20 µg/mL) as a comparative example. Cells were allowed to grow in the presence or absence (growth control) of the test agents for 24 hours. The MIC for each agent was defined as the concentration that induced a 100% growth inhibition (compared to no-drug control).

A similar microdilution-based CLSJ method (M27-A2) was used to evaluate the activity of Example 7 against *albicans* and non-*albicans Candida* species.

TABLE IV

| | Organism | Example 7 MIC (µg/ml CPC) | Chlorhexidine MIC (µg/ml chlorhexidine) |
|---|---|---|---|
| Example 48 | S. salivarius | 0.98 | 19.6 |
| Example 49 | P. gingivalis | 0.98 | 19.6 |
| Example 50 | S. pyogenes | 0.98 | 19.6 |
| Example 51 | S. pneumonia | 0.98 | 19.6 |
| Example 52 | F. nucleatum | 1.95 | 19.6 |
| Example 53 | S. mutans | 1.95 | 19.6 |
| Example 54 | S. aureus | 3.91 | 19.6 |
| Example 55 | Y. enterocolitica | 3.91 | 19.6 |
| Example 56 | S. oralis | 500 | 19.6 |
| Example 57 | S. mitis | 500 | 19.6 |
| Example 58 | C. albicans | 0.25 | 19.6 |
| Example 59 | C. krusei | 0.06 | 19.6 |
| Example 60 | C. tropicalis | 0.06 | 19.6 |
| Example 61 | C. glabrata | 0.125 | 19.6 |

The coating composition was also found to have potent antimicrobial activity against: MRSA, *Acinetobacter baumannii, Streptococcus sanguis, S. gordonii*, and *Aggregatibacter actinomycetemcomitans*.

As can be seen in Table IV, the Example 7 composition exhibited potent activity against many aerobic and anaerobic bacteria, as well as the fungi.

The MIC of the Example 7 coating composition against *S. oralis* and *S. mitis* was noticeably elevated (500 µg/mL) compared to other organisms. It is interesting to note that *S. oralis* and *S. mitis* are normal commensals of the oral cavity. Activity of the commonly used antimicrobial chlorhexidine (2% solution) was also determined by the same method. Table IV shows the MIC of the Example 7 coating composition and chlorhexidine (2% solution) as a comparative example against various microorganisms.

Taken together, these results demonstrate that Example 7 possesses potent activity against pathogenic bacteria and fungi commonly isolated from the oral cavity. This activity was more potent than that observed for chlorhexidine.

A similar activity profile was observed for the coating compositions of Examples 10 and 11.

Example 62

As a further comparison, published data shows that the tested coating composition has a better or at least equivalent MIC compared to CPC alone (i.e. not in a composition according to the barrier coating formulation disclosed herein). See Frank-Albert Pitten and Axel Kramer, "Efficacy of Cetylpyridinium Chloride Used as Oropharyngeal Antiseptic," Arzneim.-Forsch./Drug Res. 51 (II), pp 588-595 (2001), which is incorporated herein by reference. The data varies based on the microorganism tested, but, for example, CPC (alone) against *S. mutans* has an MIC of 5.0-6.25 µg/mL, which is much less effective than the 1.95 µg/ml reported in Example 53. This was an unexpected result since CPC has the risk of losing its activity when mixed with other excipient chemicals in a formulation. See Department of Health and Human Services (Food and Drug Administration) (1994) Oral Health Care Drug Products for Over-the-Counter Human Use; Tentative Final Monograph for Oral Antiseptic Drug Products. Proposed Rules (21 CFR Part 356, Docket No. 81N-033A, RIN 0905-AA06). Federal Register 59:6084-124.

Examples 63-69

Duration of Antimicrobial Activity of Coating Compositions In Vitro: Determination of Post-Antimicrobial Effect (PAE)

The PAE of Example 8 against several microorganisms was evaluated in Examples 63-68. Control Example 69 was also provided. Several microorganisms were exposed to Example 8 (at a concentration equal to the MIC) for 1 min followed by three washes to remove residual formulation. The treated cells were then spread on agar medium plates, which were incubated at 37° C., and the time taken for the cells to regrow was determined. PAE was expressed as the time (in hours) for which growth inhibition (%) was maintained by the Examples 63-68, compared to the untreated control Example 69.

Figure 10:
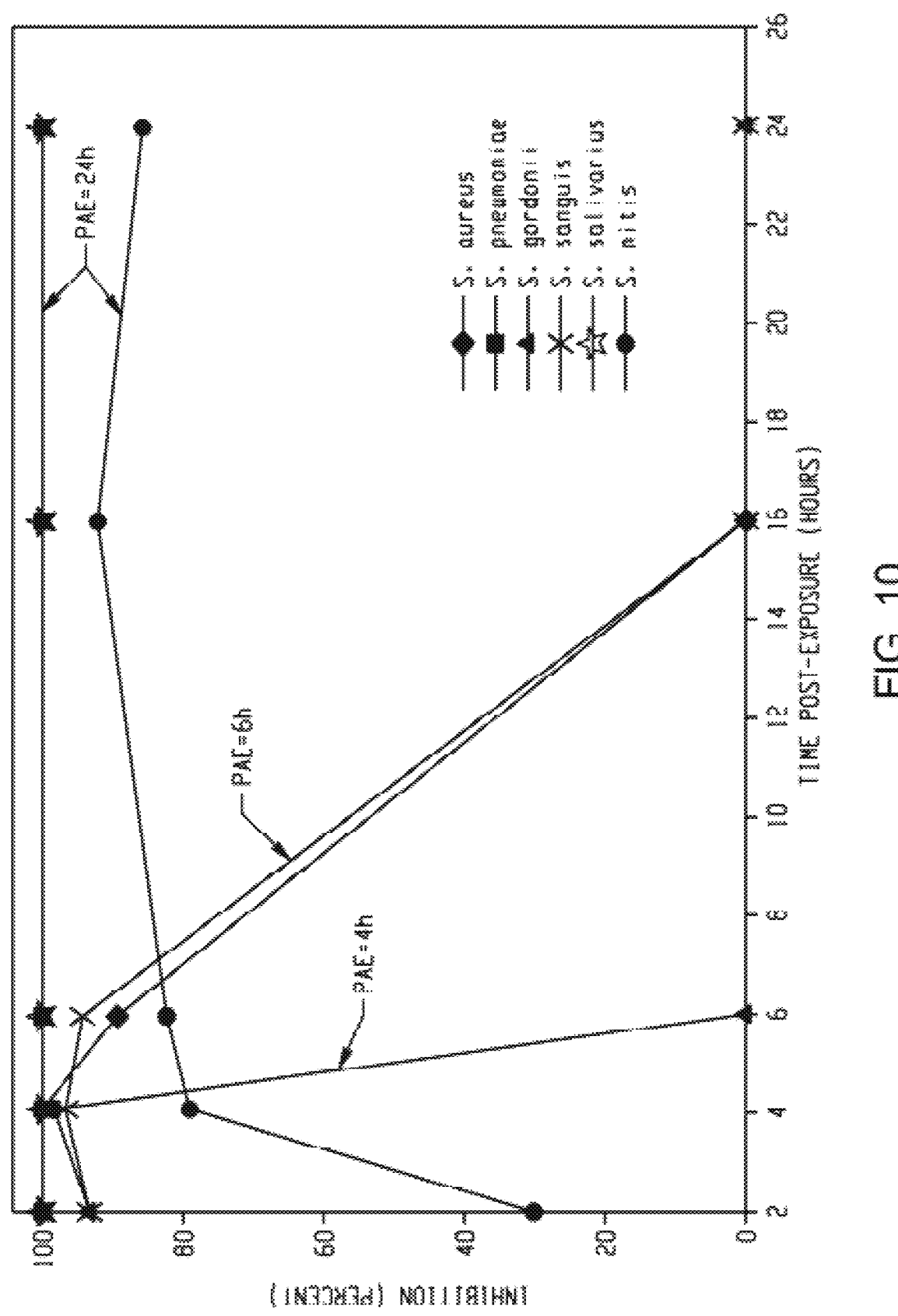
FIG. 10 is a graph showing post-antimicrobial effect of coating compositions against bacteria and fungi, as described in Examples 63-69.

As shown in FIG. 10, Example 8 exhibited a PAE ranging between 4 hours to 24 hours, depending on the organism tested (*S. aureus, S. pneumonia, S. gordonii, S. sanguis, S. salivarius*, and *S. mitis*). Similar activity of Example 8 was observed against *Candida* (data not shown). Other Example coating compositions exhibited similar PAE against microorganisms.

Example 70

Testing of PAE for the Example 7 coating composition against *S. mutans* compared to a similar comparative Example with lower CPC content of 0.7% showed that the PAE of Example 7 was 24 hours, while that of Comparative Example 70 was 6 hours. Thus demonstrating that Example 7 exhibits greater prolonged antimicrobial activity than comparative Example 70, and that additional amounts of CPC have more than a simple additive effect on antimicrobial activity.

Examples 71-76

Scanning electron microscopy was also used to show that treatment of *S. sanguis*, (Example 71), *S. oralis*, (Example 72), and *C. albicans* (Example 73) with the composition of Example 3 resulted in destruction of cellular integrity.

In Examples 71-73, cells were grown in the presence of Example 3 for 24 hours. Next, the cells were washed to remove residual formulation, dehydrated by passing through a series of alcohol solutions (10% to 100%, v/v) and processed for SEM analysis. Control Examples 74-76 differed from Examples 71-73 in that they were not grown in the presence of Example 3.

Figure 11:
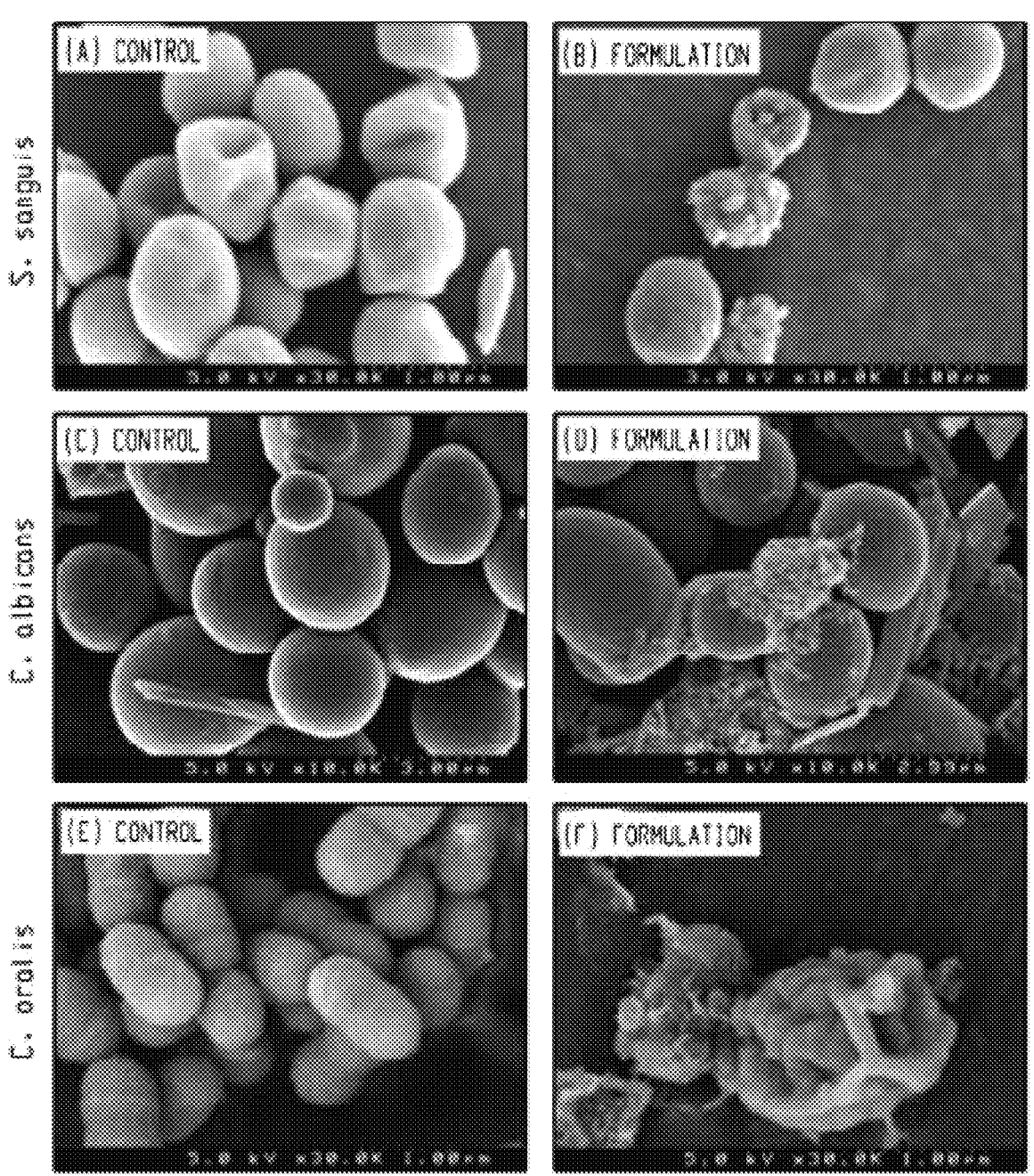
FIG. 11 shows scanning electron micrographs of *S. sanguis*, *C. albicans*, and *S. mutans*, untreated or treated with coating composition, as described in Examples 71-76.

The SEM photos showed that unlike untreated control Examples 74-76, which demonstrated healthy intact cells (FIG. 11 A, C, E), microbes exposed to the Example 3 coating composition were deformed, collapsed, and exhibited total destruction of cellular integrity with clear evidence of leakage of cytoplasmic material. (FIG. 11, B, D, F).

Examples 77-79

Since biofilms are precursors to certain infectious diseases, in Examples 77-79, experiments were performed to determine whether the coating compositions can prevent formation of biofilms by bacteria and yeasts. Biofilms were formed using an in vitro model. See Chandra et al. "In vitro Growth and Analysis of *Candida* Biofilms" Nature Protocols 3(12): 1909-1924 (2008).

In Examples 77-79 a standard biofilm model was employed to determine whether the Example 3 coating composition exhibits activity against bacterial and fungal biofilms. In Examples 77-79, three different microorganisms (*C. albicans, S. oralis*, and *S. salivarius*) were adhered on substrate for 90 minutes to allow biofilms to form to adhesion phase. Next, discs containing the adherent bacteria were incubated for 15, 30 or 60 minutes with 50% concentration of Example 3 (1:1 dilution with appropriate medium). Following incubation, biofilms were scraped, spread on culture media, incubated and colony forming units (CFUs) were determined. Media diluted with phosphate buffered saline (PBS, 1:1) were used as a control. Table V reports data at 0 (Control), 15, 30, and 60 minutes.

TABLE V

| Effect of Coating Composition on Early Phase Biofilms (log CFU) | | | |
| --- | --- | --- | --- |
| Exposure time | Example 77 *C. albicans* | Example 78 *S. oralis* | Example 79 *S. salivarius* |
| Control | 5.44 | 3.25 | 3.16 |
| 15 min | 0 | 0 | 0 |
| 30 min | 0 | 0 | 0 |
| 60 min | 0 | 0 | 0 |

Figure 12:
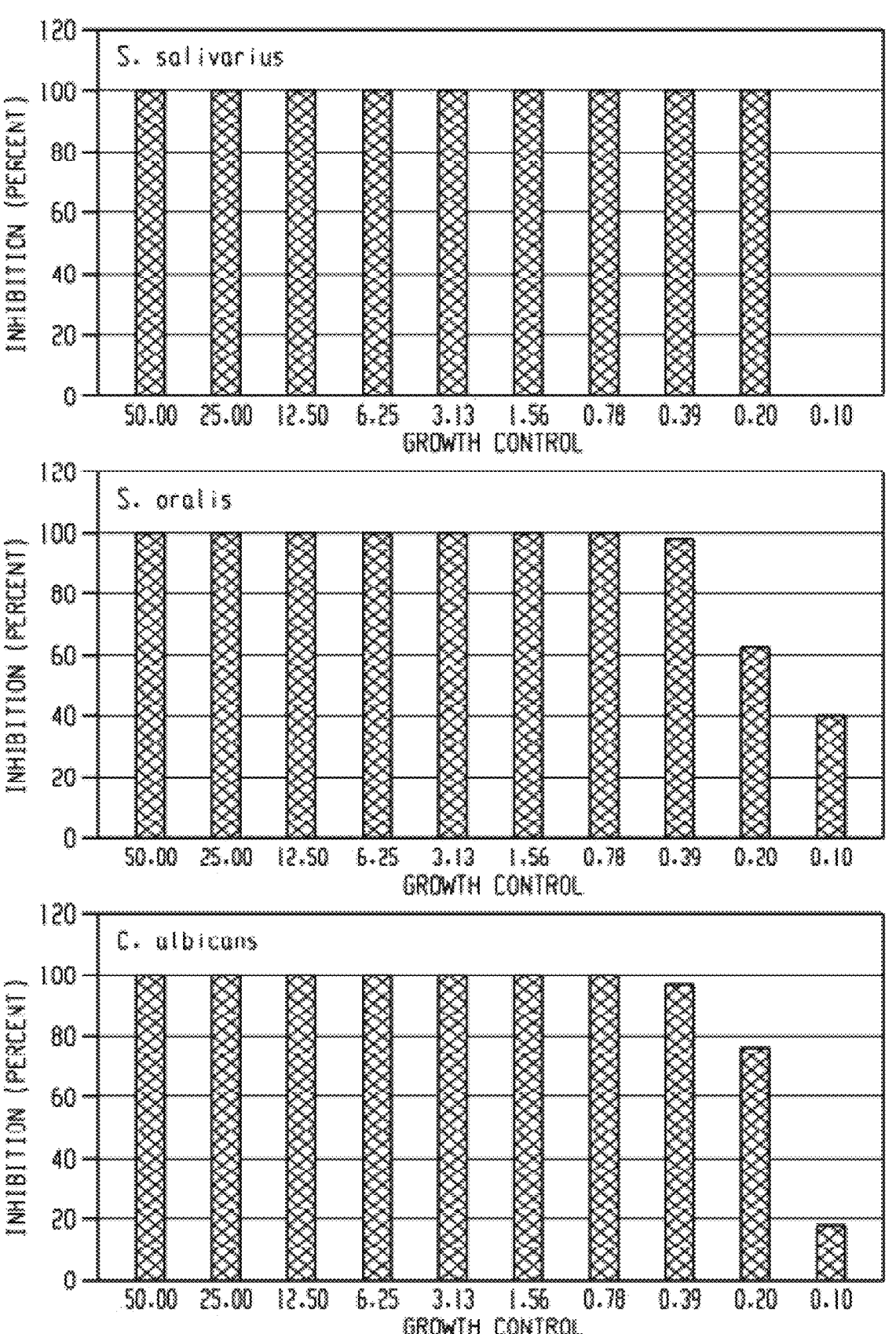
FIG. 12 presents graphs depicting activity of an example coating composition against biofilms formed by bacteria and fungi, as described in Examples 77-79.

FIG. 12 also reports data on Examples 77-79 as a graph of % inhibition versus growth control. These results showed that Example 3 coating composition inhibited bacterial and fungal microbes with an MIC of 0.2% against biofilms formed by *S. salivarius, S. oralis,* or *C. albicans*.

Examples 80 and 81

Figure 13:
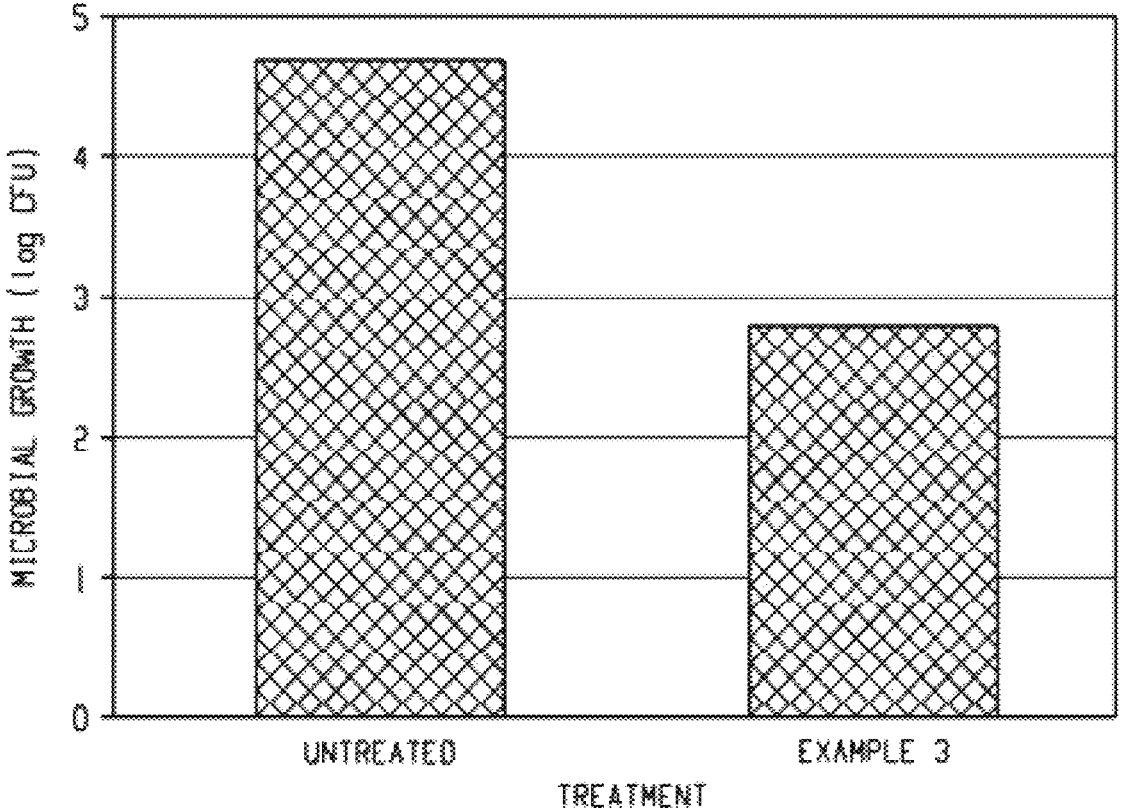
FIG. 13 is a graph showing activity of an example coating composition on microbial biofilms after a 1-min exposure, as described in Examples 80-81.

In Example 80 we evaluated the effect of 1 minute exposure of *C. albicans* early phase biofilms to Example 3, and found that even with an exposure for as short a time as 1 minute, it was able to inhibit biofilm formation (FIG. 13). Example 81 was an untreated control sample.

Examples 82-84

Ability of Coating Composition to Treat Mature Biofilms

To determine whether the coating composition can treat biofilms, we evaluated its activity against fully formed mature biofilms. Biofilms were grown to mature phase, and then exposed to Example 7 for 2 or 4 hours, and the resulting CFUs were determined. A composition that causes at least 2-log reduction in microbial CFUs compared to untreated cells is considered to be effective against microbial biofilms.

As shown in Table VI, exposure to Example 7 resulted in complete eradication of biofilms formed by *C. albicans* and *S. oralis*, and a 3.4-log reduction in CFUs for biofilms formed by *S. salivarius* compared to the untreated control (log CFU=3.95 vs. 7.36, respectively).

TABLE VI

| Effect of Example 7 on mature biofilms (log CFU) | | | |
| --- | --- | --- | --- |
| Exposure time | Example 82 *C. albicans* | Example 83 *S. oralis* | Example 84 *S. salivarius* |
| Control | 5.60 | 7.40 | 7.36 |
| 2 h | 0 | 0 | 4.00 |
| 4 h | 0 | 0 | 3.95 |

In summary, the results indicate that Example 7 possesses potent activity against biofilms formed by bacteria and fungi.

Examples 85-86

The Coating Composition is also Active Against Viruses

The activity of coating composition against viruses, including respiratory viruses (influenza virus H1N1, strain 2009/H1N1/infA) and the human immunodeficiency virus (HIV) was determined.

The Coating Composition Inhibits the Infectivity of Influenza A

To evaluate the effect of the coating composition on the infectivity of influenza virus, Madin Darby canine kidney (MDCK) cells were grown to ≥90% confluence at 37° C. prior to infection. MDCK cells are used routinely for assays involving influenza viruses.

In Example 85 cell monolayers were exposed to the Example 7 coating composition. In control Example 86 the cell layers were exposed to optiMEM (+P/S,+Lglu) tissue culture media for different times: (1) T1: 30 min exposure, (2) T2: 1 h exposure, (3) T3: 2 h exposure. Next, the formulation was removed and the cell monolayers were infected with influenza virus (multiplicity of infection (MOI)=0.1). Cells that were untreated or infected immediately after exposure (T0) were used as baseline controls. Infected cells were then centrifuged, resuspended in 500 μL of growth medium, and incubated at 32.5° C. for 48 hours. Immunofluorescence microscopy (using FITC labeled anti-influenza antibody) was also used to evaluate the effect of the Example 7 coating composition on the ability of influenza virus to infect mammalian cells.

Figure 14:
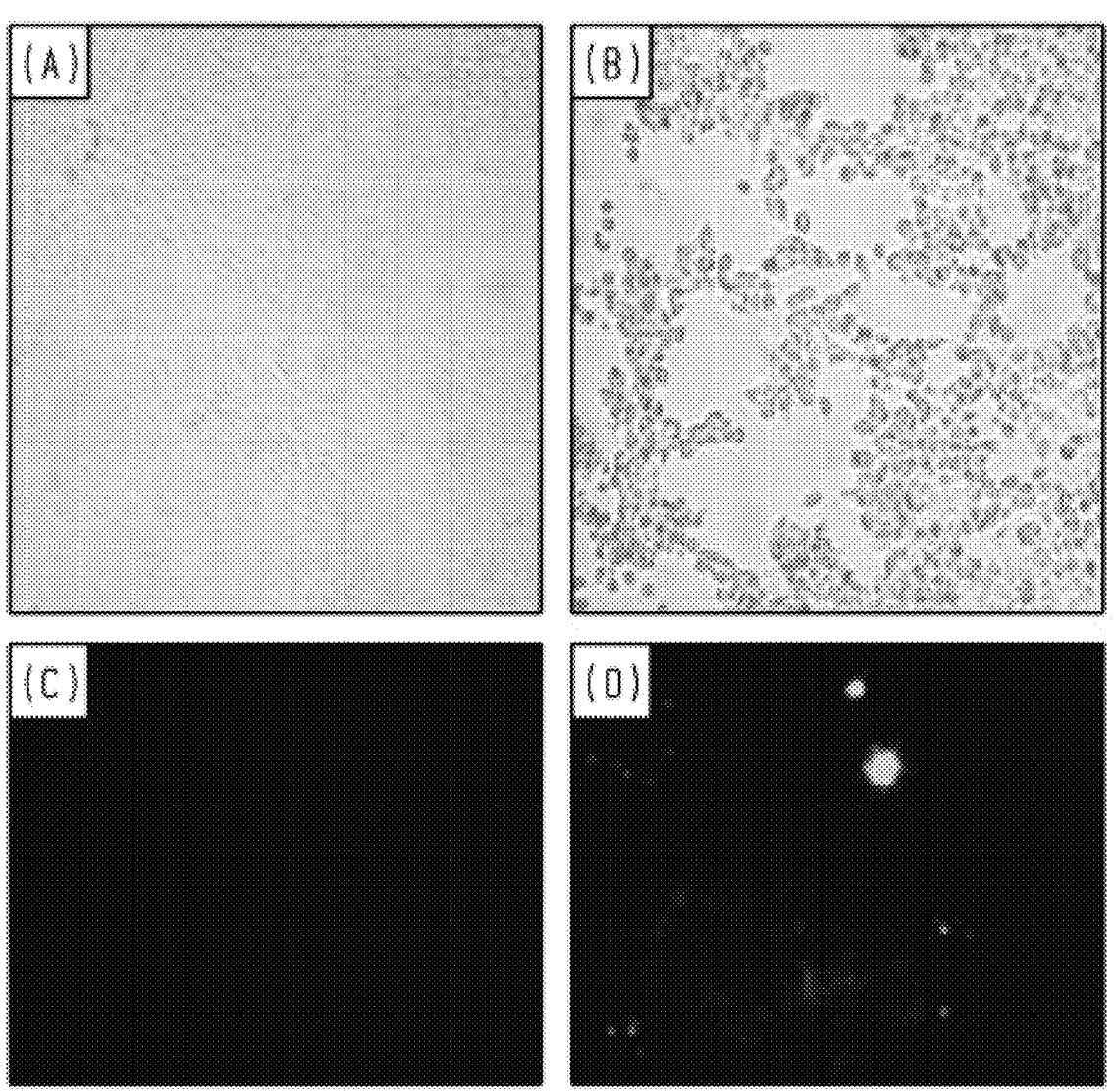
FIG. 14 presents fluorescent microscopy photographs showing the effect of an example coating composition on cytopathic effects (CPE) of influenza (H1N1)-infected MDCK cells, as described in Examples 85-86.

FIG. 14 shows the effect of Example 7 on cytopathic effects of influenza-infected MDCK cells (Example 85) (panels A and C), and control Example 86 (panels B and D). Images were obtained from: phase contrast (A-B), and immunofluorescence microscopy (C-D). No identifying cytopathic effect (CPE) was observed in formulation-treated cells. Untreated cells displayed typical CPE including focal rounding and degenerative changes.

The data showed that exposure of cell monolayers to Example 7 for 30 minutes, 1 hour, or 2 hours remained confluent and healthy (Example 85). In contrast, in the untreated cells and cells treated immediately prior to infection (T0) (control Example 86) demonstrated substantial cytopathic effect. As seen in FIG. 14 panel C, no fluorescence was observed in the coating composition treated cells of Example 85, while the untreated cells of Example 86 exhibited fluorescence (FIG. 14 panel D).

Figure 15:
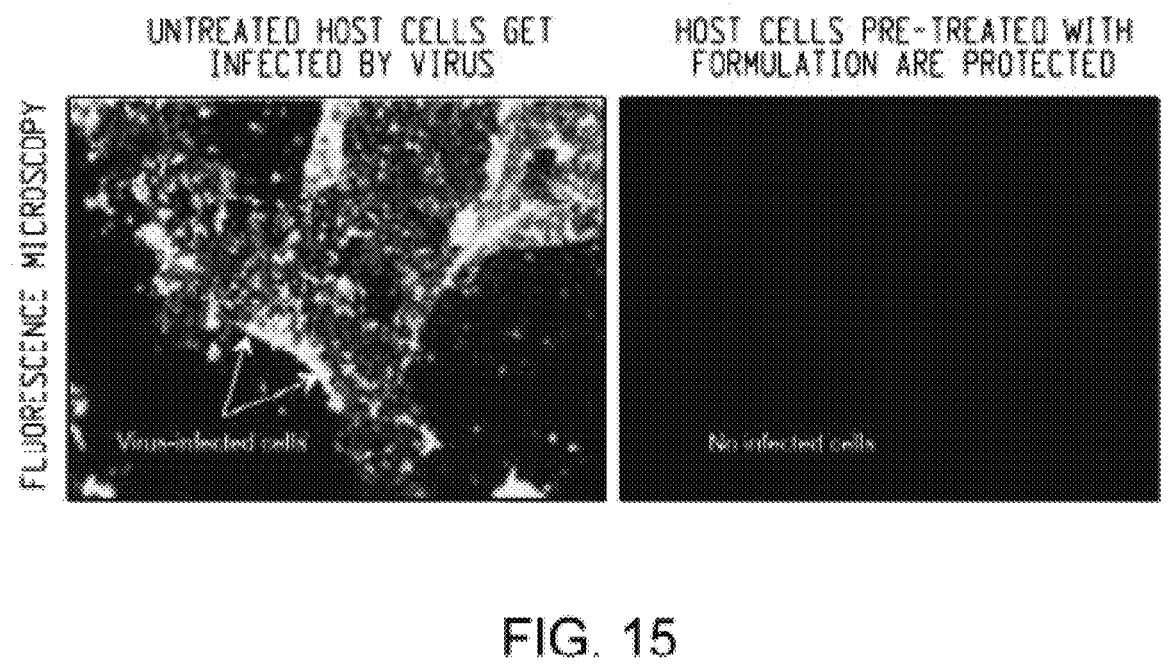

Further fluorescence microscopy images corresponding to Examples 85 and 86 are presented in FIG. 15.

Examples 87 and 88

Activity of Coating Composition on Viral Load Using Quantitative PCR.

Figure 16:
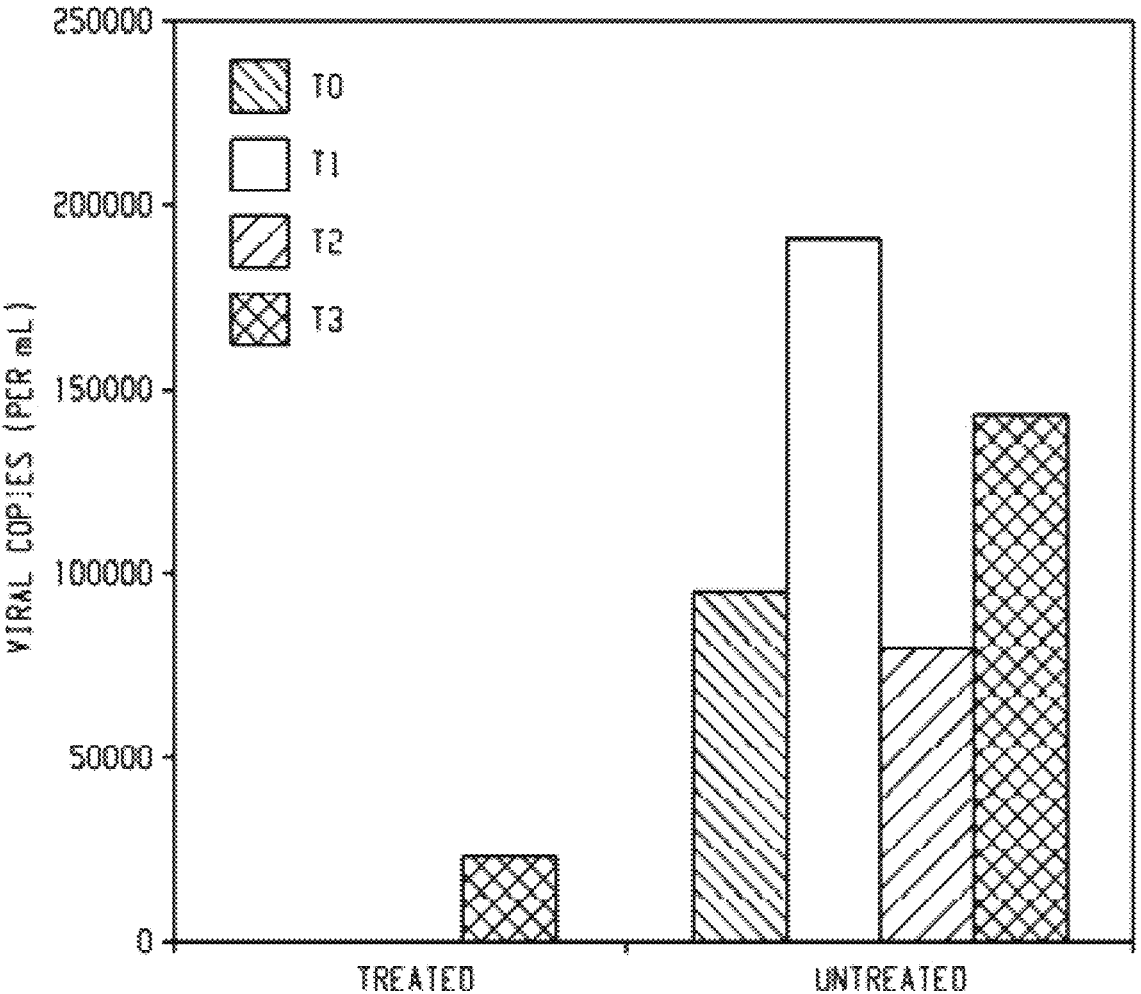
FIG. 16 is a graph showing levels of influenza virus in infected coating composition treated and -untreated cells, as determined by quantitative PCR, as described in Examples 87-88.

FIG. 16 shows levels of influenza virus in infected treated cells (Example 87) and untreated cells (Example 88), as determined by quantitative PCR. In Example 87, cells were treated with Example 7 and in control Example 88 the cells were left untreated. Later the supernatants were collected and analyzed for the presence of virus.

Cell culture supernatants from the same assay as in Examples 87 and 88 were collected and nucleic acid extracted using QIAamp Viral RNA Kit (QIAGEN, Valencia, CA). Random hexamer primers (Invitrogen Carlsbad, CA) were used to create a cDNA library for each specimen. Reverse transcription reactions were performed with M-MLV RT (Invitrogen, Carlsbad, CA) according to the manufacturer's specifications. Quantitative analysis was performed on a StepOne Plus Taqman Real Time PCR (Applied Biosystems, Branchburg, NJ) using TaqMan Universal PCR Master Mix (Applied Biosystems, Branchburg, NJ), 2 μl of cDNA sample, and primers/probes targeting the influenza matrix gene. A reference standard was prepared using a cDNA fragment of the H1N1 matrix gene and human RNAse P amplified by conventional RT-PCR, gel purified (QIAquick, Qiagen, Valencia, CA), and quantified using a spectrophotometer (Beckman Coulter, Brea, CA).

As shown in FIG. 16 and Table VII, the Example 87 cells treated Example 7 for 30 min or 60 min did not have detectable influenza at 48 hours post infection. Moreover, treatment with Example 7 for 2 hours resulted in a 6-fold decrease in viral load, compared to the untreated control or those treated immediately prior to infection (Example 88).

TABLE VII

| | Example 87 | Example 88 (control) |
|---|---|---|
| 30 min | 0 | 192000 |
| 60 min | 0 | 79800 |
| 120 min | 23400 | 143000 |

Examples 89-91

Coating Composition has Direct Antiviral Effect Against Influenza Virus

To determine whether the coating composition has direct antiviral activity against influenza virus, we infected African Green Monkey Kidney (CV-1) cells (grown in 24-well plates to 90% confluence) with influenza virus that was pre-treated with Example 7. CV-1 cells are routinely used a highly susceptible substrate for diagnosis and study of viruses.

In Examples 89-91, a standardized amount of influenza (0.1 MOI) was pretreated for 5 minutes at room temperature with: (1) Example 7 (to form Example 89), (2) control Example 6, a compound without CPC but with preservatives (to form Example 90), and (3) control Example 5 placebo alone (a compound without CPC and preservatives) (to form Example 91). After the 5 minute incubation virus/drug mix was diluted by an additional equal volume with optiMEM (+P/S,+Lglu) to dilute out the treatment compositions.

In Examples 89-91, CV-1 cells were prepared as described in above. The Example 89-91 treated and untreated viruses were then inoculated onto the cells as described above.

Figure 17:
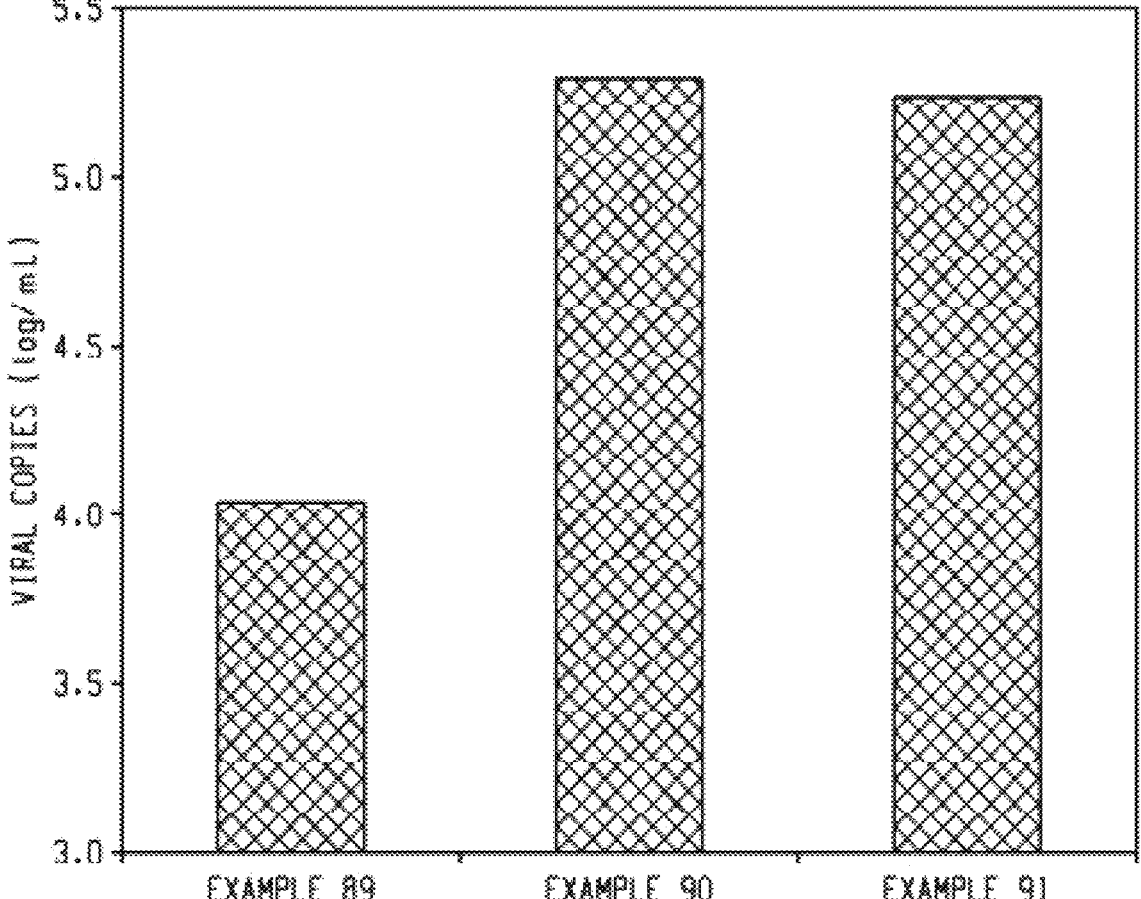
FIG. 17 is a graph showing direct antiviral activity of example coating compositions prepared with or without preservatives and antimicrobial agent (CPC) against influenza virus, determined using quantitative PCR, as described in Examples 89-91.

Influenza viral load was determined by real time PCR as described above. The data as shown in FIG. 17 showed significant decrease in viral load for influenza virus pretreated with the Example 7 coating composition containing the antimicrobial agent CPC (Example 89), compared to those containing only the coating composition and/or preservative but no CPC (Examples 90 and 91). Pre-treatment of virus with Example 7 exhibited significant decrease in viral copies, compared to formulations with no CPC.

These results demonstrate that the Example 7 coating composition possesses direct antiviral activity against influenza virus that is not inherent in Examples 5 and 6.

Examples 92 and 93

In Examples 92 and 93, the coating composition's ability to inhibit the infectivity of influenza A (2009/H1N1/infA) was tested. African Green Monkey Kidney (CV-1) cells were grown in 24-well plates to 90% confluence. Next, the coating composition, Example 7, was applied to the cells (20% Example 7, 80% OptiMeM, working CPC concentration of 0.02%) in Example 92. Each time point matched with control Example 93 (No coating composition applied, 100% OptiMeM). The coating composition was allowed to dwell on the surface for 30 minutes, and then removed from the ceil monolayer. Cells were thoroughly washed twice with sterile optiMEM (+PfS,+Lglu). Influenza was inoculated at MOi=0.1 at 30 minute intervals from T0 through T+6 hours. Following infection, cells were then centrifuged @2200 rpm×30 minutes and 500 μl of optiMEM (+P/S, +Lglu, 2 μg/ml trypsin (sigma-Aldrich, St Louis, MO)) was applied. Infected cells were grown at 32.5° C. for 96 hours at 5% $CO_2$. The influenza viral load was determined by real time PCR.

Figure 18:
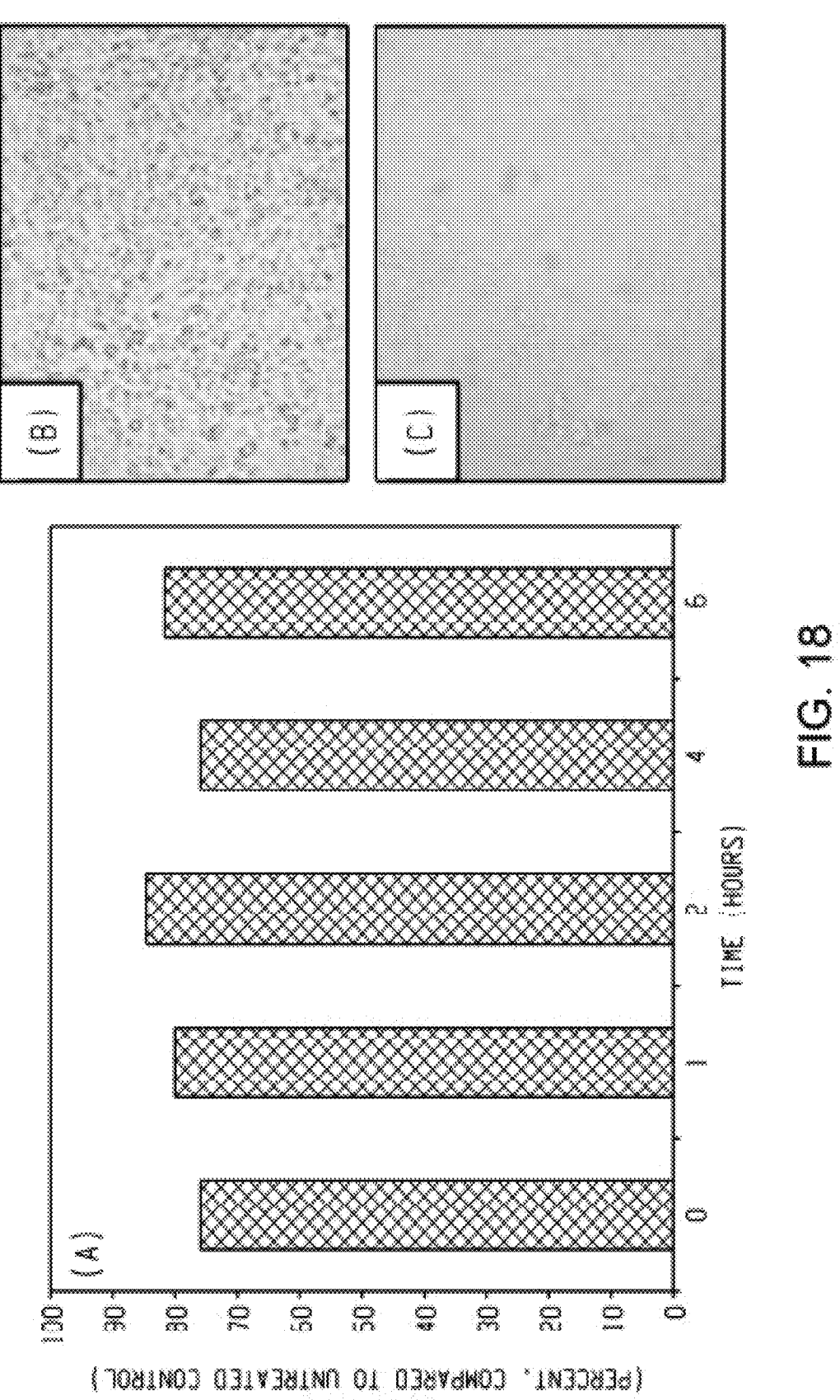
FIG. 18 shows the activity of an example coating composition against H1N1 virus over a 6 hour time period. Panel (A) is a graph showing a percent inhibition in viral growth compared to an untreated control. Panels (B) and (C) are micrographs of (B) untreated and (C) coating composition treated cells.

As shown in FIG. 18, pre-treatment of host monolayers with glycerine-xanthan gum formulation results in inhibition of viral infection by up to 84.93% compare to untreated controls. The fact that inhibition of viral infection was observed in host cells despite removal of the coating composition demonstrates that the coating composition formed a protective barrier coating on host cells, which prevented viral invasion for at least 6 hours.

Figure 1B:
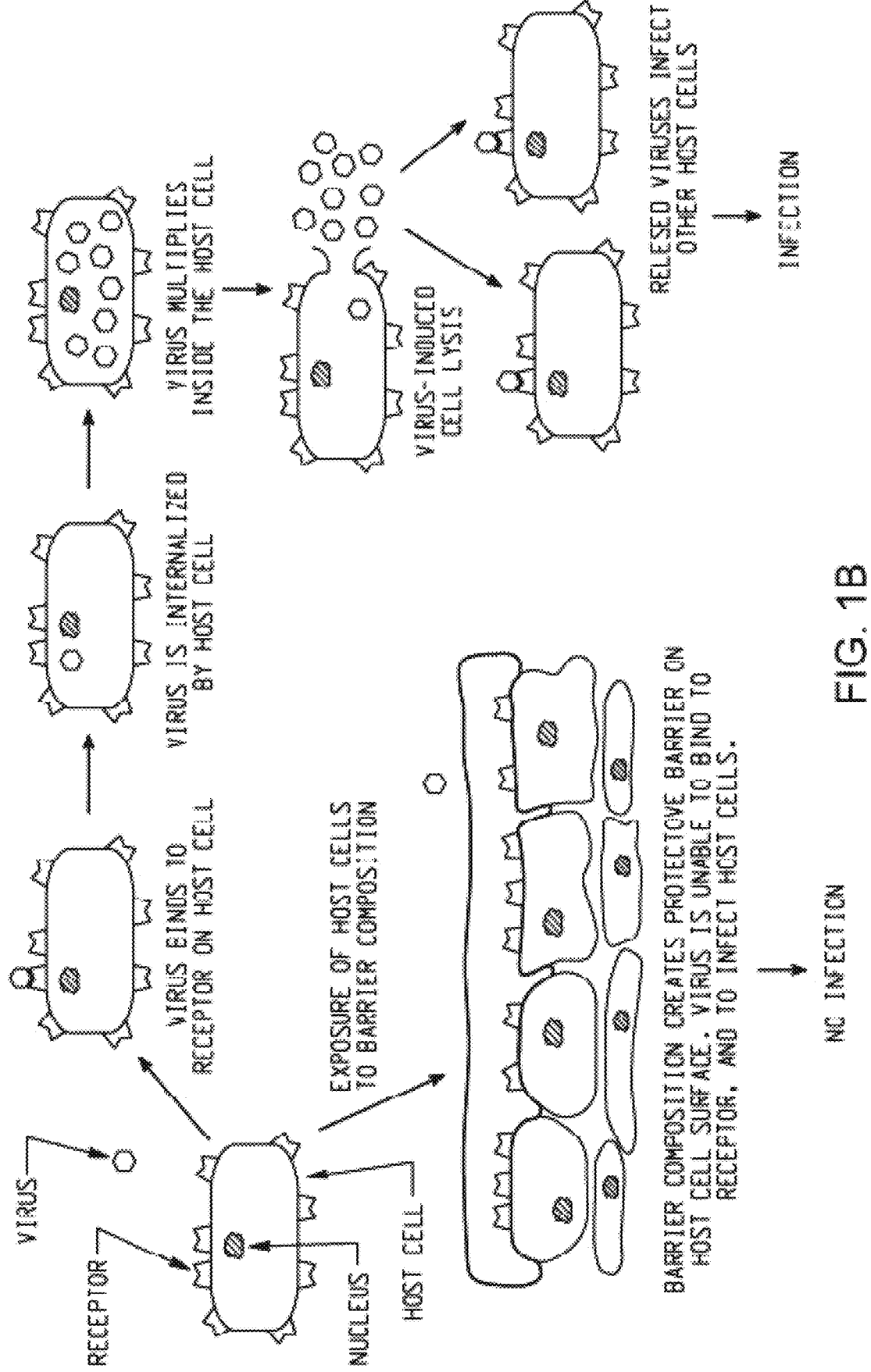
FIG. 1B is a depiction of a proposed mechanism of antimicrobial activity in an embodiment of the coating composition.

FIG. 1B may be referred to as a possible mechanism accounting for the inhibition of infection.

Examples 94-96

Coating Composition Exhibits Activity Against HIV

Figure 19:
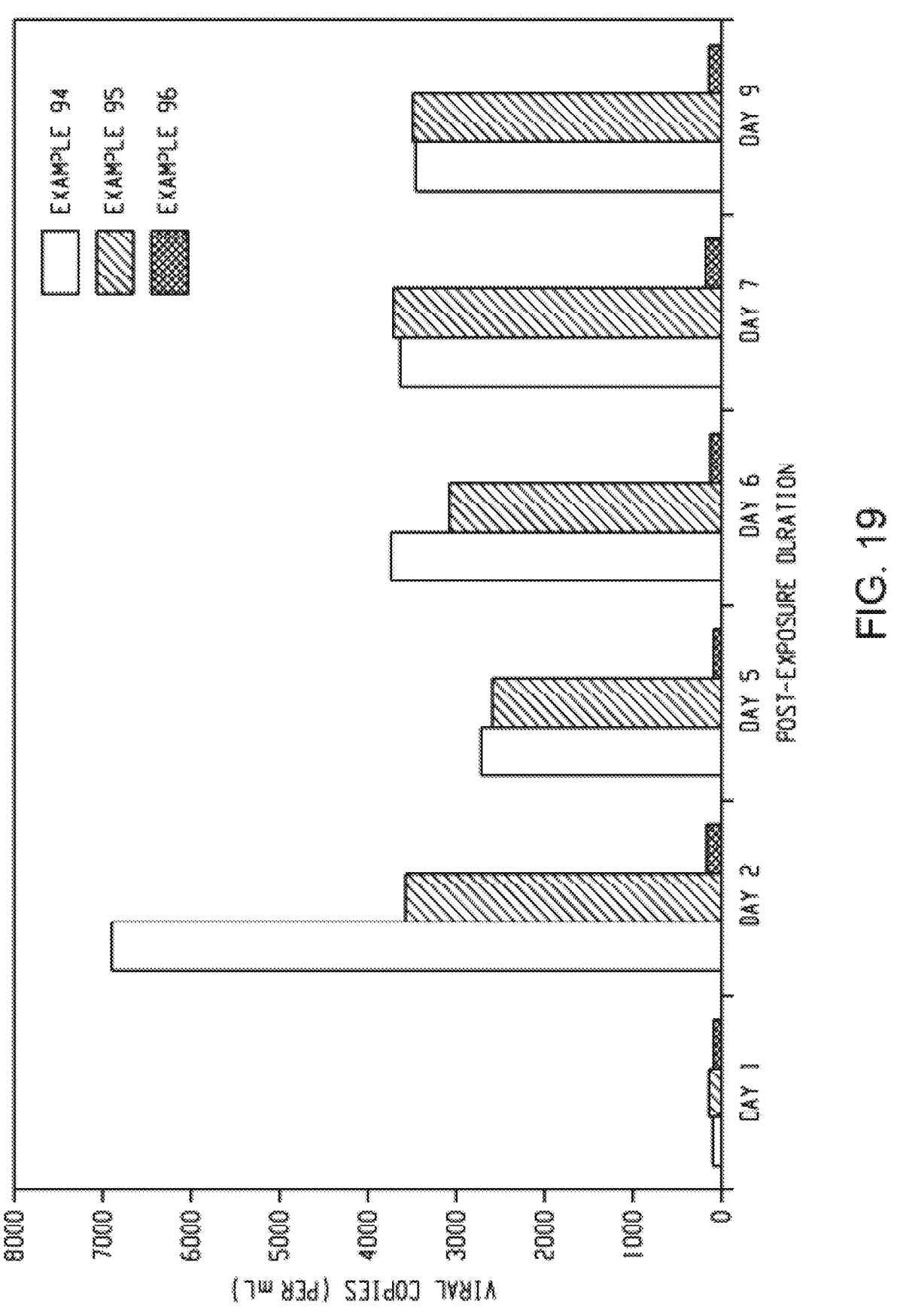
FIG. 19 is a graph showing the activity of formulations against HIV, as described in Examples 94-96.

Examples 94-96 determined whether the coating composition possessed activity against HIV. Host MT mammalian cells were plated into 96-well round bottom plates at a density of 15,000 cells/well in RPMI/10% FBS/PS. The next day (Day 2), virus was pretreated with control Example 5 (to form Example 94), control Example 6 (to form Example 95), or Example 7 (to form Example 96) for 5 minutes and added to cells. After 24 hours of exposure to formulation, the MT (macaque) mammalian cells were washed 3 times with phosphate buffered saline (PBS) and fresh media was replaced. Supernatant (10 μL) was collected post-treatment on Days 1, 2, 5, 6, 7, and 9, and the viral load was determined by reverse transcriptase (RT) activity. FIG. 19 shows a graph of the viral copies per ml for each of Examples 72-74 over a 9 day span.

The results showed that Example 7 in Example 96 exhibited anti-HIV activity at all time points monitored post-treatment.

The control Example 5 or control Example 6 without CPC and/or preservative in Examples 94 and 95 exhibited only minimal anti-HIV activity.

In summary, our findings demonstrate that the coating composition Example 7 containing CPC exhibits long-lasting antiviral activity against HIV.

Example 97

Representative organisms viral lesions are important infections in different mucosal tissues. In Example 97 an experiment was performed to determine whether the coating composition exhibits activity against the common oral Epstein-Barr virus (EBV). Western blotting was used to evaluate the ability of the Example 8 coating composition to degrade lytic viral protein EAD (indicating inhibition of viral replication).

Figure 20:
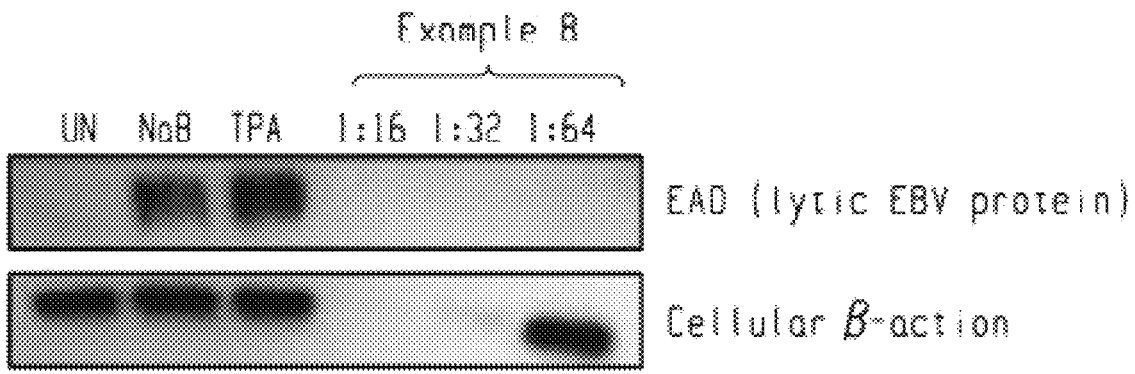
FIG. 20 is a Western blot showing activity of Example 8 against Epstein-Barr Virus (EBV), as described in Example 97.

In Examples 97, EBV-infected gastric epithelial cells were exposed to different dilutions (1:16, 1:32 and 1:64) of Example 8, and the presence of EAD protein was detected using specific antibodies. Presence of cellular R-actin was used as an indicator of epithelial cell integrity. As shown in FIG. 20, 1:64 dilution of Example 8 degraded EAD without affecting cellular actin. These results demonstrate that Example 8 specifically inhibits viral replication, and as such, is an effective anti-viral and useful for prevention of viral infection.

Examples 98-100

Duration of Anti-Microbial Barrier Versus Commercial Mouthwash Product

Figure 3:
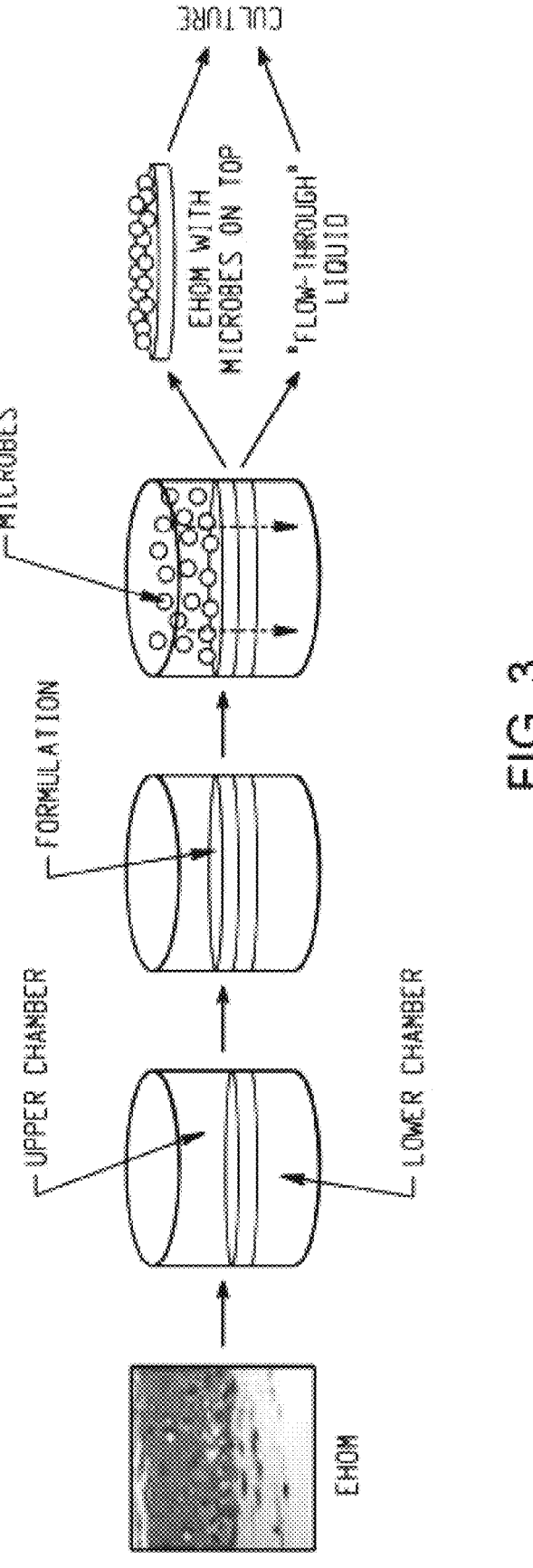
FIG. 3 is a schema showing the method of evaluation of microbial growth in the upper and lower chambers of an EHOM assay, as described in Examples 27-28.

To determine the duration for which the coating composition can maintain the antimicrobial activity, bacteria and fungi were exposed to an EHOM of Example 2 that was treated with the coating composition of Example 7 in a well and an EHOM of Example 2 that was treated with a comparative commercial product in a well for 2 minutes. The bacterial and fungal microbes were overlaid on top of the control untreated EHOM (Example 98) and the treated EHOMs (Example 99 and Comparative Example 100). Next the residual (flow-through) solution was removed from the bottom well (lower chamber of the EHOM model) and spread onto agar medium plates. FIG. 3 depicts this test method for further clarity. These plates were then incubated at 37° C., and the number of microbial cells (colony forming units, CFUs) growing after 24 hours were counted.

In control Example 98 an untreated EHOM was tested. In Example 99 *S. mitis* bacteria was overlaid on the coating composition as described above. Example 100 is a comparative example showing the activity of commercially available LISTERINE (containing ethanol (26.9%), menthol, thymol, methyl salicylate, and eucalyptol) against *S. mitis* bacteria. Table VIII shows the results.

TABLE VIII

| | CFUs of *S. mitis* bacteria in flow through liquid from EHOM | | |
|---|---|---|---|
| Time post-exposure | Example 98 (control) | Example 99 | Example 100 (comparative) |
| 2 hours | 1150000 | 5820 | 780000 |
| 4 hours | 1400000 | 5500 | 800000 |
| 6 hours | 1600000 | 6000 | 840000 |

Examples 101-103

In Examples 101-103, the same procedure of Examples 98-100 was performed except *Candida albicans* fungus was tested on the coating composition as described above. Table IX shows the results. Example 103 is comparative, showing the activity of commercially available LISTERINE.

TABLE IX

| | CFUs of *Candida albicans* in flow through liquid from EHOM | | |
|---|---|---|---|
| Time post-exposure | Example 101 (control) | Example 102 | Example 103 (comparative) |
| 2 hours | 1150000 | 12000 | 124000 |
| 4 hours | 2900000 | 12000 | 252000 |
| 6 hours | 3900000 | 13000 | 350000 |

The data further showed that Example 7 coating composition maintained activity for up to and including 24 hours. Taken together, these results showed that unlike LISTERINE, the Example 7 coating composition continued to maintain an intact barrier on EHOM tissues for up to and including 24 hours.

Examples 104-153

Examples 104-153 were performed to identify further examples of concentrations of glycerin and xanthan gum that can form a barrier effective in preventing the passage of microorganisms. Since this application does not require a barrier that prevents passage of microorganisms, this data is omitted. However, patent publication U.S. 2012/0270909, incorporated herein by references includes this information.

It should be noted that an effective barrier coating for a surface treatment may be formed at lower concentrations of glycerine and/or xanthan gum when an effective antimicrobial is added. This is because the antimicrobial and barrier coating act in tandem to stop and/or kill the harmful microbes. In the case of a composition for applying to an inanimate surface, it is not so important to block passage of a microorganism to the other side of the barrier coating, since an inanimate surface cannot be infected.

Examples 154-160

Examples 154-160 were performed to demonstrate safety of the composition on mucosal surfaces. Patent publication U.S. 2012/0270909 incorporated herein by reference includes this information.

Example 161

Glycerine-Xanthan Gum Formulations Form a Coating on the Human Oral Mucosa

To determine whether glycerine-xanthan gum formulation can form a coating on the human oral mucosa, we spiked the Example 7 formulation with Gentian Violet (GV) as a marker dye. The spiked product (750 µL) was sprayed onto the oral cavity of human volunteers. Post-application, the oral cavity was inspected for staining, and the images were captured using a digital camera. As shown in FIG. 21, the formulation stained both cheeks and the dorsal/ventral surface of the tongue.

Examples 162 and 163

Exposure of Microbes to Coating Composition Inhibits Cell Growth: Time-Lapse Microscopy To determine the inhibitory activity and duration for which coating compositions exhibit activity against microbes, time-lapse analysis was performed on cells exposed to the coating composition, compared to untreated bacteria and fungi.

In Example 162, *S. mutans* microbial cells were exposed to Example 7 for one minute, washed to remove any residual agent, and allowed to grow in a petri-dish containing fresh growth medium. Growth of organisms at 37° C. was monitored for a 6 hour period, and photomicrographs were taken every 20 minutes over the 6 hour incubation period using a camera connected to the microscope.

In control Example 163 the same procedure was followed with untreated cells.

Figure 22:
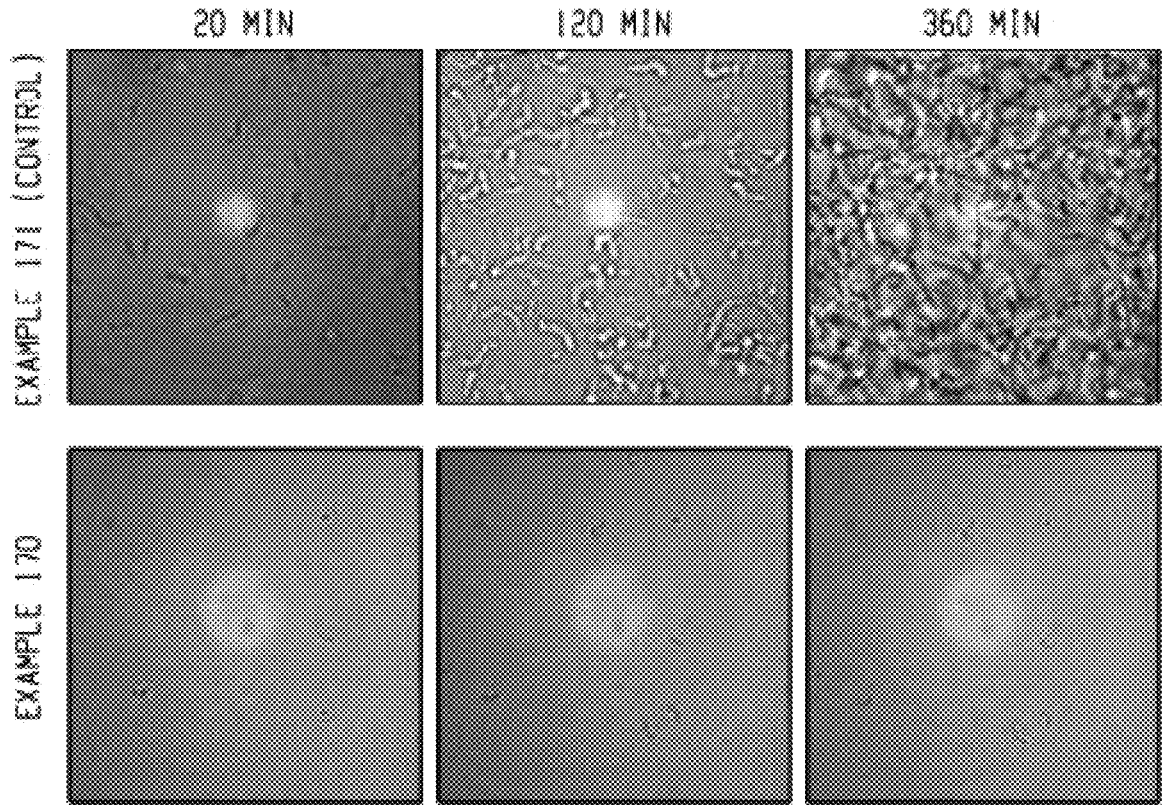
FIG. 22 are photographs showing time-lapse microscopy of bacterial growth after a 1 minute exposure to an example coating composition, as described in Examples 162-163. Images represent bacterial growth after 20 min, 120 min, or 360 min post-exposure.

As shown in FIG. 22, in contrast to the untreated bacteria, where cells reached confluence by 6 hours, microbes treated with the Example 7 coating composition failed to regrow during the same time period post-exposure. Similarly, exposure of *Candida* cells to the Example 7 coating composition completely inhibited growth during the incubation period (data not shown).

These results further confirmed that the coating composition possesses prolonged antimicrobial activity.

Examples 164-166

In vivo Study: Coating Composition (Example 7) Lowers the Oral Microbial Load in Humans: Short- and Long-Term Activity
Short-Term Activity The duration of activity of Example 7 was determined in healthy individuals by evaluating the effect of a single application on microbial burden of the oral cavity. In Examples 164-166, three healthy individuals (over 18 years of age, healthy mouth) were enrolled with informed consent, and asked to apply a single application of the composition of Example 7 on their cheeks. A single application was defined as three sprays of 0.25 ml each in volume. Next, swabs were collected from these individuals at baseline (pre-treatment), 1 hour, 2 hours, and 6 hours post-treatment. Swabs were cultured on agar media plates specific for aerobic or anaerobic organisms, incubated for 24-28 hours at 37° C., and the number of CFUs were counted. Effect of Example 7 on microbial burden was determined (CFUs), and percentage inhibition was calculated for each post-exposure time point relative to the baseline (0 minutes) CFUs.

Figure 23:
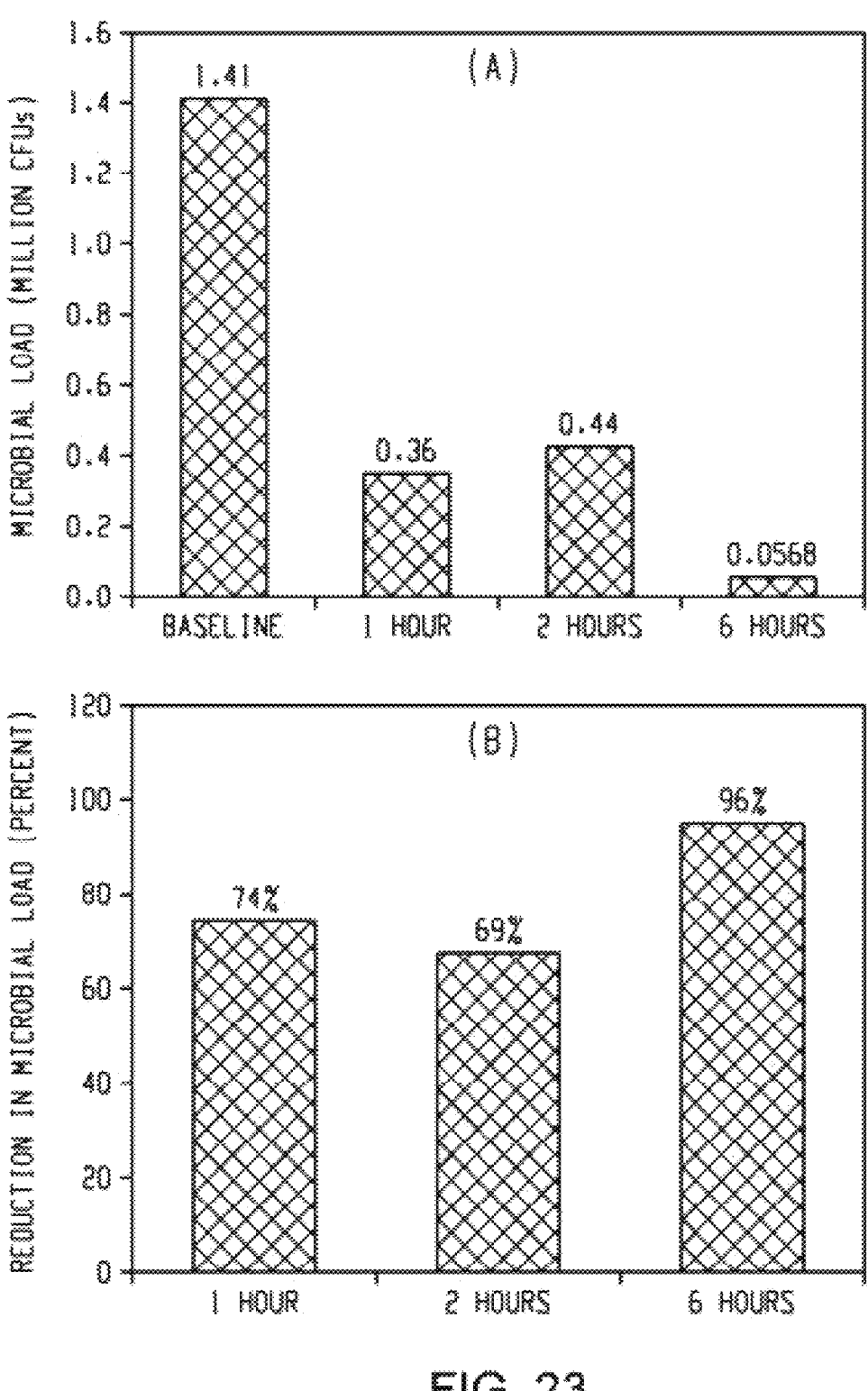
FIG. 23 is a graph showing the effect of a single dose of an example coating composition on oral microbial burden of a healthy individual, as described in Example 164-166. (A)—Microbial load in CFUs, (B) reduction in microbial load (%) compared to baseline.

The results showed that application of Example 7 led to consistent reduction in microbial load for up to 6 hours (See FIG. 23A, which shows CFUs of a representative tested individual. Treatment with the coating composition resulted in 69% to 96% reduction of the microbial burden in the oral cavity (See FIG. 23B, which shows a representative individual's reduction in microbial load.)

Examples 167-169

Long-Term Activity

The activity of the coating composition over a 5-day period against oral microbes was evaluated. In Examples 167-169, three healthy individuals were enrolled, and asked to apply a single dosage (three sprays 0.75 mLs total) of Example 7 three times daily (approximately 9 AM, noon, and 3 PM) for a 5-day period (representing a typical 5-day work-week). Swabs were collected from these individuals at baseline (before application on day 1) and at the end of the day on each day during the 5-day period. Collected swabs were cultured on agar media plates, incubated for 24-28 hours at 37° C. and at 5% $CO_2$ humidity, and the number of CFUs were counted.

The effect of the Example 7 coating composition on microbial burden was determined (as median CFUs for the three subjects), and percentage inhibition was calculated for each post-exposure time point relative to the baseline (0 min) CFUs. FIG. 24 shows these results in a graph of CFUs versus time (FIG. 24A) and reduction in microbial load versus time (FIG. 24B). Examples 167-169 demonstrate that application of Example 7 over 5 days led to consistent reduction in microbial load over the 5-day test period (FIG. 24A). Treatment with the Example 7 coating composition resulted in 65%-88% reduction of the median microbial burden in the oral cavity of the study participants (FIG. 24B).

Examples 170-198

Figure 25:
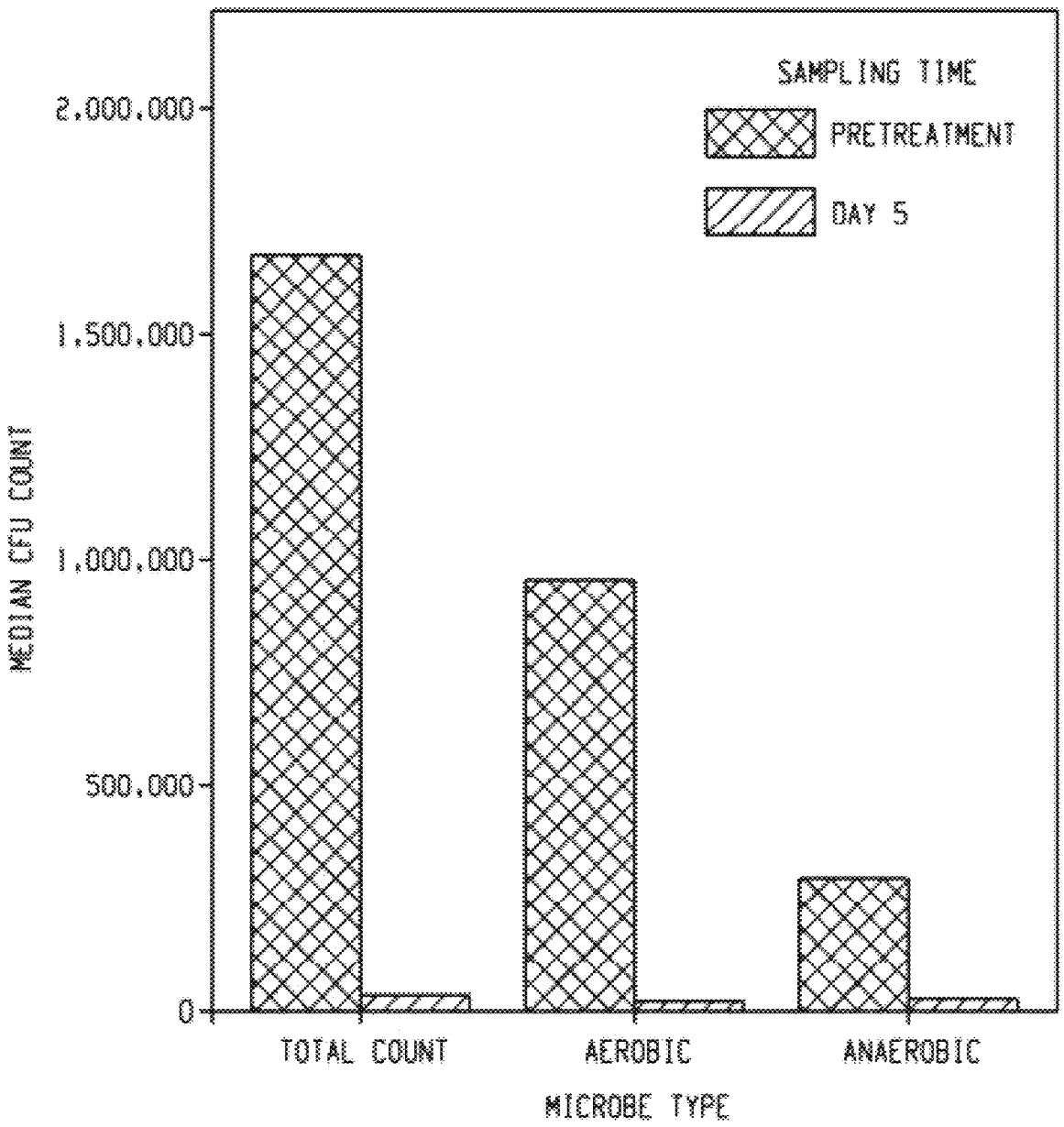
FIG. 25 is a graph showing the effect of an example coating composition on microbial burden of the oral cavity after 5-day usage in 31 healthy subjects, as described in Examples 170-198.
Figure 26:
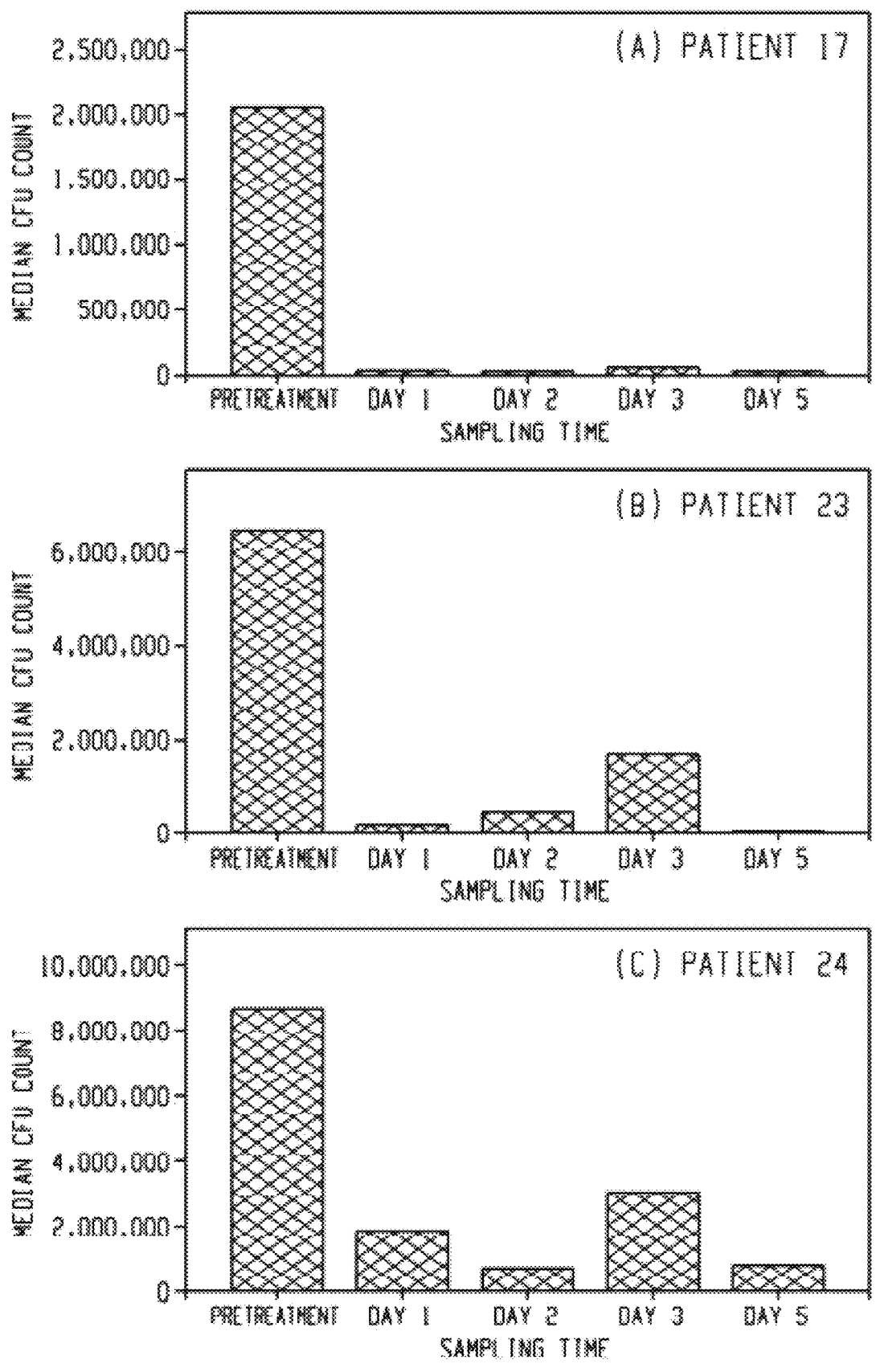
FIG. 26 is a graph showing the microbial load in oral samples obtained from three representative study participants, as described in Examples 170-198.

In a clinical study, twenty-nine healthy individuals were enrolled after informed consent. Baseline information was recorded (age in years, gender, ethnicity, and date of enrolment). Oral examination of the mouth was undertaken, and the inside of the mouth (cheek) was swabbed with a sterile culture swab. Baseline oral swab samples were cultured to determine bacterial load prior to study. In Examples 170-198, each of the twenty-nine participants were given a spray bottle containing the coating composition of Example 7 and instructed to spray the inside of their mouth for a total volume of 0.75 ml, then swish for 30 seconds and swallow. Two groups of approximately equal number of participants were tested. One group used the example coating composition every two hours, three times a day, for five days (a typical work week). The other group used the example coating composition every two hours, four times a day, for five days (a typical work week). No substantial difference was noted in the two groups. Swabs were collected on days 1, 2, 3, and 5 at the end of the day (8 hours after the first administration of the coating composition) and cultured on media specific for aerobic and anaerobic bacteria. Data were presented as number of microbes: total, aerobic and anaerobic. FIG. 25 shows a graph of total microbial load and breaks down the total into aerobic and anaerobic counts from just prior to treatment and on day 5 of treatment. FIG. 26 shows graphs of microbial load over the 5 day period in oral samples obtained from three representative study participants.

Overall, the in vivo testing showed that the coating composition exhibits antimicrobial activity against oral microbes, as measured by reduction in the levels of these organisms, over both short- and long-term duration.

The data showed that treatment with the coating composition over a 5-day period resulted in reduction in the oral microbial load, for total microbes, aerobic and anaerobic organisms.

Example 199-205

Figure 27:
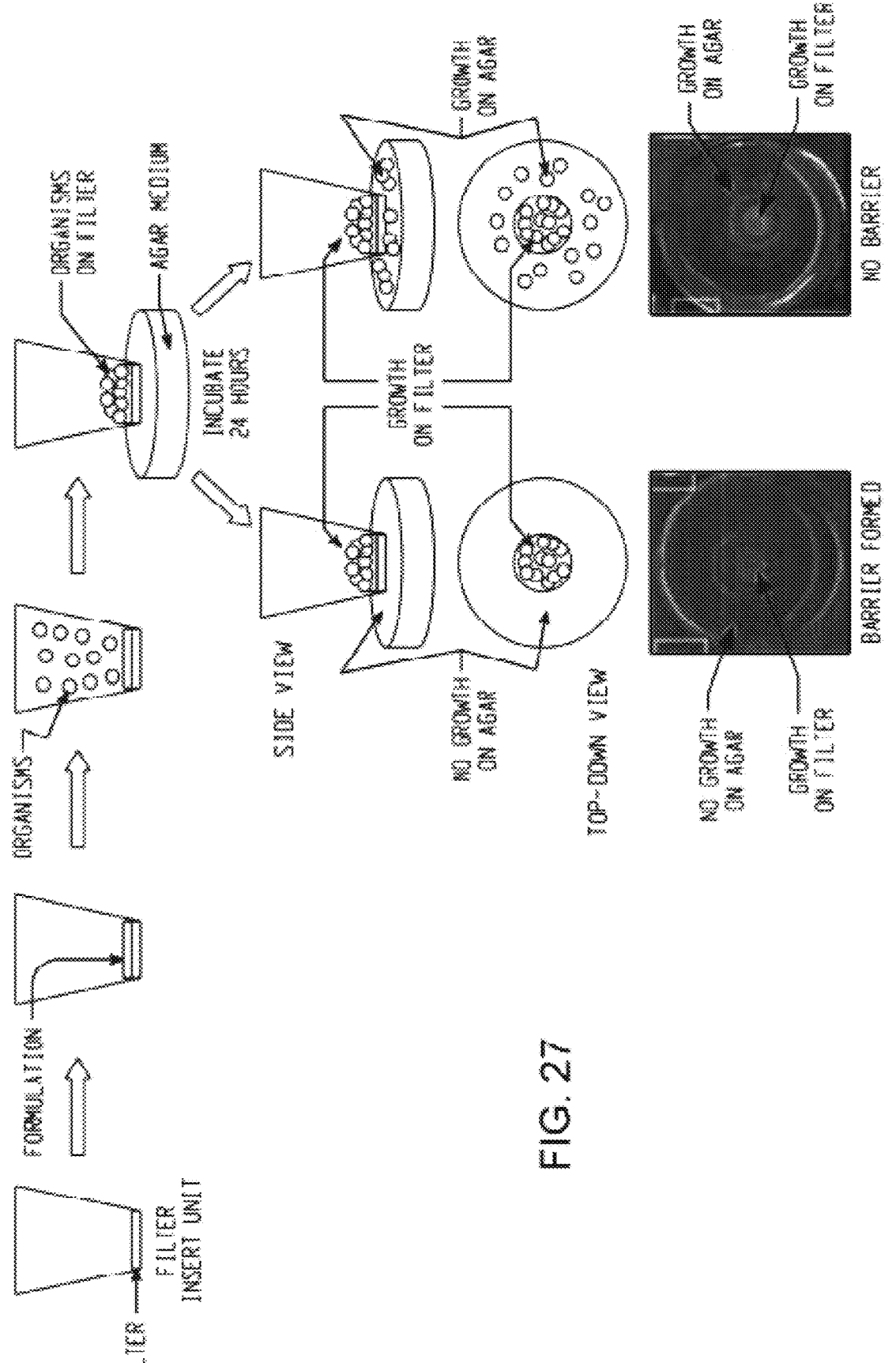
FIG. 27 shows is a schema describing the in vitro filter insert-based model to evaluate penetration of microbes across the barrier formed by example coating compositions, as described in Examples 199-205.

Identification of Additional Humectants for Forming a Barrier to Prevent Microbial Penetration In Example 199 an in vitro filter insert-based model (see FIG. 27) was used to test different humectants at different concentrations.

Six compositions were prepared according to Table X based on the mixing procedures used for Examples 3-8.

TABLE X

|  | Ex. 199 | Ex. 200 | Ex. 201 | Ex. 202 | Ex. 203 | Ex. 204 | Ex. 205 |
|---|---|---|---|---|---|---|---|
| Xanthan Gum | 0.4 | 0.4 | 0.4 | 0.4 | 0.4 | 0.4 |  |
| Glycerin | 4.5 | 4.5 | 4.5 |  |  |  | 4.5 |
| Sorbitol |  | 4.5 | 4.5 | 4.5 |  | 4.5 |  |
| Xylitol |  |  | 4.5 | 4.5 | 4.5 |  | 4.5 |

Next, 100 μL of Examples 199-205 were placed into filter inserts (pore size 0.8 μm diameter, that allows both bacteria and fungi to pass through) and allowed to form a layer. Next, organisms were overlaid on the layer formed by the test solutions. The filter inserts containing the layer of test solutions and microorganisms were then placed on the surface of agar media plates and incubated for 24 hours at 37° C. After the incubation period, the agar media plates were evaluated for growth on filter insert and in the agar media. Growth on filter insert but no growth in agar media indicated that the test solution formed a barrier, which prevented the microbes from passing through. In contrast, microbial growth in the filter insert as well as the agar media indicated that no such barrier was formed.

The results showed that each of the xanthan gum-based solutions containing the tested humectants (singly or in combination) formed intact barriers on the filter insert that prevented the passage of microorganisms into underlying agar medium.

Example 206-213

Determination of the Solubility Limits of Xanthan Gum

To determine the solubility of xanthan gum, it was mixed at different concentrations in water and the solubility observed by monitoring the presence or absence of clumps and free flow of the mixture. Table XI reports the results and concentrations.

TABLE XI

| Example | Xanthan Gum Concentration | Solubility |
|---|---|---|
| 206 | 0.40% | free flowing viscous solution |
| 207 | 0.45% | some clumps, viscous solution |
| 208 | 0.5% | more clumps, viscous solution |
| 209 | 0.6% | clumps, more viscous than above |
| 210 | 0.7% | clumps, more viscous than above |
| 211 | 0.8% | Extensive clumps, highly viscous solution, no free flow |

TABLE XI-continued

| Example | Xanthan Gum Concentration | Solubility |
|---|---|---|
| 212 | 0.9% | Extensive clumps, highly viscous solution, no free flow |
| 213 | 1.00% | Extensive clumps, highly viscous jelly, no free flow |

We found that when mixed at 0.4%, xanthan gum formed a free-flowing viscous solution (Table XI). In contrast, mixtures containing 0.45% or 0.5% xanthan gum formed a viscous fluid but contained small clumps. The extent of clumps increased with increasing concentration of xanthan gum (0.6% and 0.7%). At concentrations ≥0.8%, xanthan gum mixture contained extensive clumps, with a jelly-like consistency and no free flow.

Example 214

Comparison of Cationic CPC in Coating Composition with Neutral Antimicrobial Agent in Coating Composition In Example 214, the formulation of Example 7 was made, except the neutral agent Citral was used instead of CPC. The antimicrobial activity of formulations containing CPC (0.1%) or Citral (0.5%) against *Streptococcus* was ascertained. The assay described above in Examples 48-61 was used to perform these studies.

The results showed that the formulation containing citral exhibited antimicrobial activity (MIC=12.5%). However, activity of formulation containing citral was significantly less potent than that containing CPC (MIC=0.098%).

Example 215

Physico-Chemical Testing of Hydrophobicity and Comparison

In Example 215 thin layer chromatography analysis was used to compare the hydrophobicity of Example 7 with a hydrophobic composition. The hydrophobic composition was comprised of the components in Table XII.

TABLE XII

|  | Wt % |
|---|---|
| Glycerin | 7 |
| Sorbitol | 5 |
| Poloxamer 338 | 1 |
| PEG 60 Hydrogenated castor oil | 1 |
| VP/VA copolymer | 0.75 |
| Sodium benzoate | 0.5 |
| Cellulose Gum | 0.2 |
| CPC | 0.05 |
| Methyl Paraben | 0.05 |
| Propyl paraben | 0.05 |
| Sodium Saccharin | 0.05 |
| Xanthan Gum | 0.01 |
| Disodium Phosphate | 0.006 |
| Flavoring and coloring agents | 0.121 |

*the remainder of the composition was purified water

10 μL of Example 7 and the hydrophobic composition were deposited on pre-made TLC plates (at a distance of 2 cm from the bottom edge). The spots were air-dried for 5 minutes, and the plates were placed in a TLC chromatography jar containing water as a solvent. The TLC system was allowed to run until the solvent front reached the top edge of the plate. Plates were removed and the solvent and sample fronts were marked. The Relative Front (Rf) values were calculated for the two samples using the formula I:

$$Rf = \text{Distance travelled by spot/Distance travelled by solvent front} \qquad \text{I.}$$

The results showed that the Rf value for the hydrophobic composition and Example 7 were 0.33 and 0, respectively, indicating that the hydrophobic composition was highly miscible in water. In contrast, Example 7 did not exhibit any mobility in the aqueous solvent, demonstrating that this formulation is hydrophobic or not hydrophilic.

Example 216

A coating composition was made by mixing the components according to Table XIII below in water to form a solution. A eucalyptol component was also included in an amount of 5× per the Homeopathic Pharmacopeia, but also did not affect the test results, other than demonstrating that the composition still works with this component added into it. All percentages are by weight.

TABLE XIII

| | Antimicrobial (CPC) | Humectant (Glycerin) | Gum (Xanthan Gum) |
|---|---|---|---|
| Example 216 | 0.01% | 35% | 0.4% |

Examples 217-219

The coating composition was also shown to have effectiveness in killing allergy causing molds. MIC tests were performed on a polystyrene plastic surface.

In Example 217 the coating composition of Example 216 was tested to determine its MIC against Stachybotrys MRL 9740. The Example 7 composition had an MIC of 0.06 micrograms/ml.

In Example 218 the coating composition of Example 216 was tested to determine its MIC against *Aspergillus fumigatus* 18748. The Example 7 composition had an MIC of 0.49 micrograms/ml.

In Example 219 the coating composition of Example 216 was tested to determine its MIC against *Cladosporium*. The Example 7 composition had an MIC of 0.39 micrograms/ml.

Because Stachybotrys and *Aspergillus fumigatus* are mold-causing organisms, these examples further support the embodiment wherein the coating composition is applied to surfaces to prevent or treat mold growth or discoloration.

Examples 219-224

In Examples 219-224 the effect of coating composition on MRSA biofilm formation on a silicone elastomer disc surface was evaluated.

In Examples 219-221, three silicone elastomer discs with a 1 cm diameter were pre-sprayed with 0.25 ml with the Example 7 coating composition for 60 min and incubated at 37° C. In Examples 222-224 a control example was performed by treating a silicone elastomer disc with an equivalent amount of a phosphate-buffered saline (PBS) for 60 minutes and incubated at 37° C.

The Example 219-224 pretreated discs were each submerged in 4 ml MRSA suspension ($1\times10^7$ cells/mL), and incubated at 37° C. for 90 min ("Adhesion Phase"). Next, the discs with adherent cells were removed and transferred to wells containing 4 ml of Brain Heart Infusion (BHI). The wells were incubated at 37° C. on a rocker for 24 hours. Biofilm formation on the discs was evaluated by quantitative culturing on BHI agar plates. Scanned images of the wells were recorded using a scanner.

Figure 28:
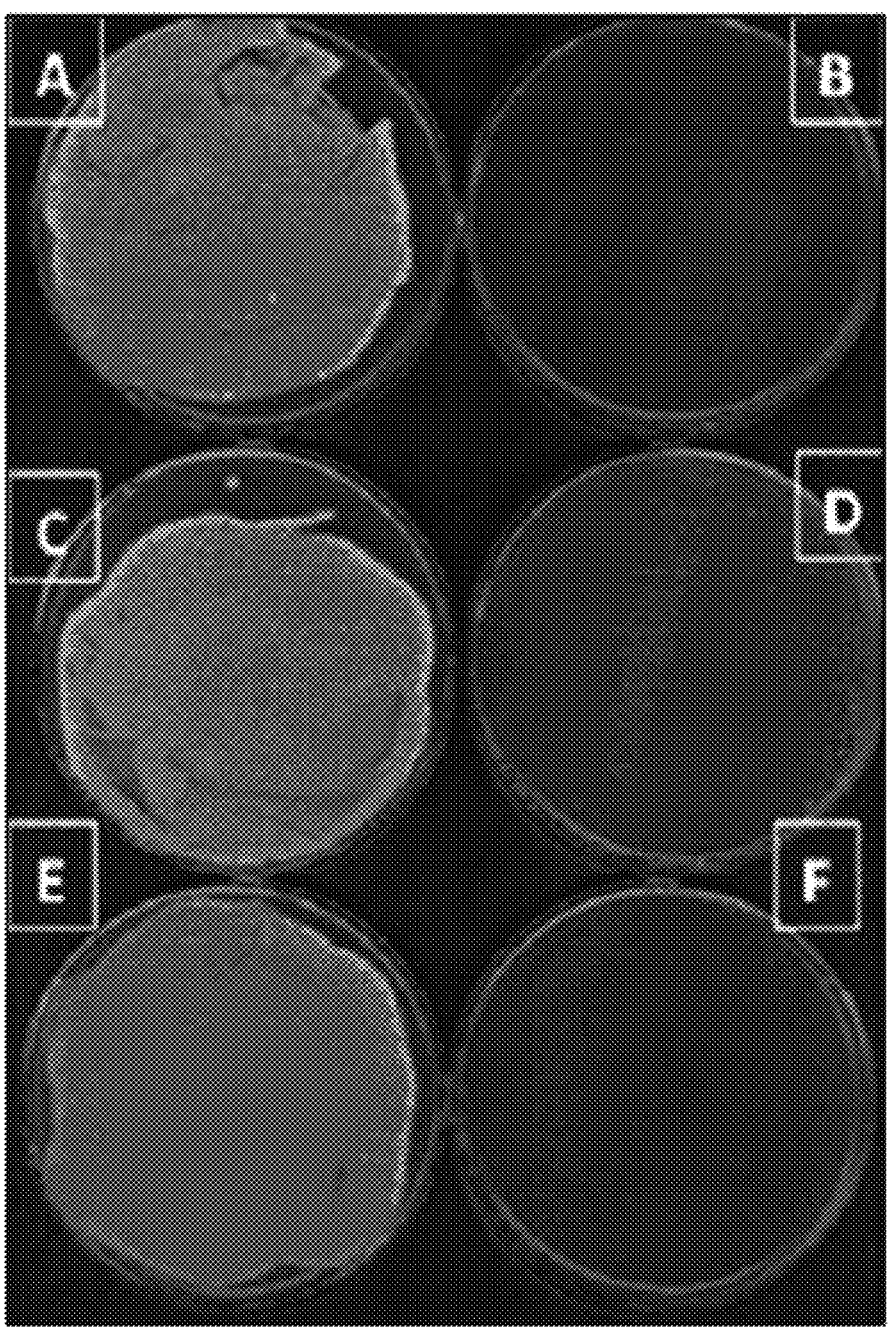
FIG. 28 is a set of photographs showing growth of MRSA biofilms on the surface of silicone elastomer discs treated with PBS (control, A, C, E) and Example 7 coating composition (B, D, F), as described in Examples 219-224.

As shown in Table XIV, pre-treatment with Example 7 coating composition prevented formation of biofilms on the disc surface. FIG. 28 shows images of colony burden in biofilms formed by MRSA on the PBS treated (A, C, E) and Example 7 treated (B, D, F) discs.

TABLE XIV

| Treatment | Example | MRSA CFUs/mL |
|---|---|---|
| Example 7 | 219 | 0 |
| coating | 220 | 0 |
| composition | 221 | 0 |
| PBS | 222 | $1.58 \times 10^8$ |
| | 223 | $1.72 \times 10^8$ |
| | 224 | $1.53 \times 10^8$ |

Examples 225-246

The Example 7 coating composition was tested to determine its efficacy against several strains of *Bordetella pertussis*. In test Examples 225-235, agar-based assays were constructed in which Example 7 coating composition was incorporated in Regan-Lowe Charcoal agar BBL #297883 plates as a 64 microgram/ml dilution in water. Control Examples 236-246 were agar plates containing no Example 7 coating composition. In each of Examples 225-246 $5\times10^4$ cells (50 uL) of *Bordetella pertussis* were spotted on the test surface and plates were incubated at 37 degrees C. for 24 hours. As shown in Table XV, confluent growth was observed in control Examples 236 to 246, while no growth was observed in test Examples 236-246. The designation 4+ means luxurious growth.

TABLE XV

| Example | Bordetella pertussis Strain # | Microbial Growth |
|---|---|---|
| 225 | J11E | None |
| 226 | J11F | None |
| 227 | J14B | None |
| 228 | J14C | None |
| 229 | J14D | None |
| 230 | J14G | None |
| 231 | J32B | None |
| 232 | J32C | None |
| 233 | J32D | None |
| 234 | J36E | None |
| 235 | J36F | None |
| 236 | J11E | 4+ |
| 237 | J11F | 4+ |
| 238 | J14B | 4+ |
| 239 | J14C | 4+ |
| 240 | J14D | 4+ |
| 241 | J14G | 4+ |
| 242 | J32B | 4+ |
| 243 | J32C | 4+ |
| 244 | J32D | 4+ |
| 245 | J36E | 4+ |
| 246 | J36F | 4+ |

Examples 247-252

The antiviral activity of the coating composition, Example 7 (in various diluted concentrations) was evaluated against the ATCC VR-1200 strain of rhinovirus.

Human Hepatoma (HUH-7) Cells were prepared in 24-well plates with Dulbecco's Modified Eagle Medium (DMEM) with 10% heat inactivated fetal calf serum and supplemented with L-glutamine (Lglu) and penicillin/streptomycin (P/S) (unless specified, all reagents produced by Gibco, N.Y., USA). All culture cells were grown to 90-100% confluence at 370 at 5% CO₂ and then washed with OptiMEM+P/S+Lglu once prior to infection.

In Examples 247-251, the Example 7 composition was applied to cell monolayers at varying concentrations (5%, 10%, 15%, 20%, 50% diluted in 400 microliter optiMEM (+P/S, +Lglu)) for a working CPC concentration of 0.005%, 0.01%, 0.015%, 0.02% and 0.05% respectively, and was allowed to dwell for 1 hour prior to inoculation. In control Example 252 400 microliter optiMEM (+P/S,+Lglu) was applied to the cells and allowed to dwell for 1 hour prior to inoculation.

The cell monolayers were then removed from the Example 7 dilutions or control optiMEM and rhinovirus was applied at a multiplicity of infection (MOI) of 0.1. Cells were incubated with virus at 32.5° C. for 1 hour. After which the inoculum was removed and 500 ul OptiMEM+P/S+Lglu was placed on the cells. Cells were then grown at 32.5° C. at 5% CO2. After 5 days incubation, cell culture supernatants were collected for rhinovirus viral load quantification.

Rhinovirus viral titer of the Example 247-251 cell culture supernatants were measured by real time PCR. In comparison to Control Example 252 significantly decreased rhinovirus viral load was demonstrated in Example 251, which was a 50% concentration of Example 7. See Table XVI below.

TABLE XVI

| Example | Wt. % Example 7 | Amount | Viral load/mL |
|---|---|---|---|
| 247 | 5% | 303354.64 | 12141854.69 |
| 248 | 10% | 5628.209 | 2251283.75 |
| 249 | 15% | 92717.83 | 37087131.25 |
| 250 | 20% | 8776.60 | 3510638.67 |
| 251 | 50% | 0 | 0 |
| 252 | 0 (control) | 95307.36 | 38122943.75 |

Examples 253 and 254

A test Example 253 was formulated with a 50% Example 7 diluted suspension (0.05 CPC concentration) in 500 microliter optiMEM (+P/S,+Lglu). A control Example 254 was formulated as a control solution with no Example 7 (500 microliter optiMEM (+P/S,+Lglu)). Examples 253 and 254 were applied the cells disclosed in Examples 246-252, but at defined intervals: T–1 hour, T–30 min, and T–0 (Immediate) prior to infection.

The cell monolayers were then removed from the Example 253 suspension and the Example 254 control solution. The rhinovirus viral particles were applied to the treated cell monolayers at a multiplicity of infection (MOI) of 0.1. Cells were incubated with virus at 32.5° C. for 1 hour. After which the inoculum was removed and 500 ul OptiMEM+P/S+Lglu was placed on the cells. Cells were then grown at 32.5° C. at 5% CO₂ for 5 days. The cells treated with Example 253 and 254 were viewed daily for the presence of cytopathic effect. After 5 days incubation, cell culture supernatant was gathered for immunofluorescence and rhinovirus viral load quantification.

Figure 29:
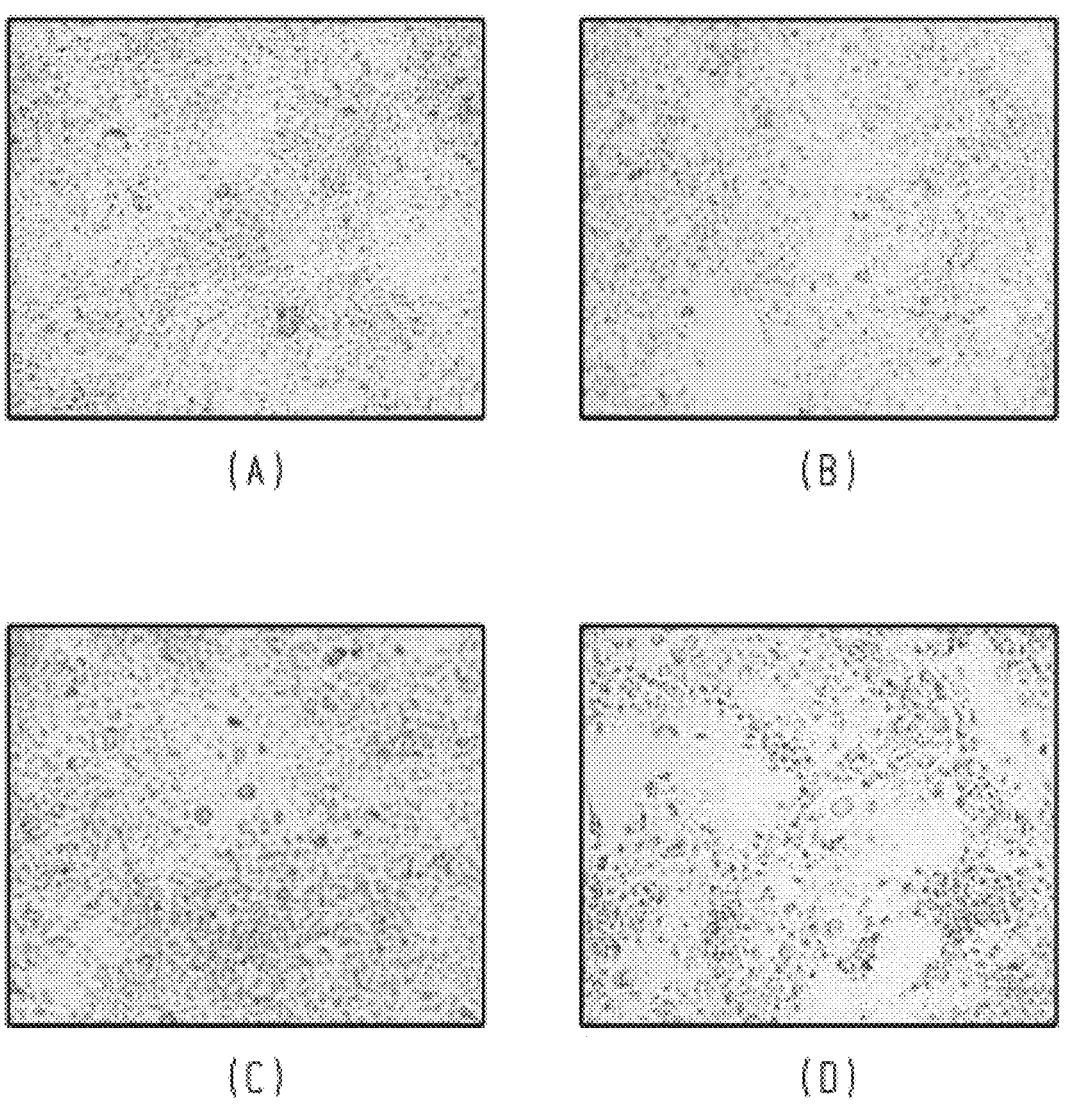
FIG. 29 is a set of photographs showing cell monolayers treated with an embodiment of the coating composition, Example 252, for varying time periods (a), (b), and (c), and a control Example 253 (d).

FIG. 29 discloses photos of cells treated with test Example 253 at FIG. 29(a) T–1 hr, FIG. 29(c) T–30 min and FIG. 29(b) T 0 (immediate). None of these photos demonstrated any cytopathic effect and healthy cells overgrew the plate. However, as shown in FIG. 29(d) the Example 254 untreated control cells demonstrated focal rounding, detachment and cell death. Cytopathic effect determination included the development of focal rounding, cell size enlargement or reduction, syncytial formation, development of multinucleated giant cells, and detachment.

Immunofluorescence was determined as follows: Virus infected cell monolayers and uninfected control were washed with sterile PBS. The cells were trypsinized, spotted upon wells on slides and fixed with acetone. The slides were tested by DFA employing FITC labeled monoclonal antibodies. An indirect immunofluorescence assay was performed using Light Diagnostics Pan-Enterovirus Detection Kit (Millipore). This detection kit is well described for having cross reactivity with rhinovirus infected cells. All antibody dwell steps occurred for 1 hour at 37° C. Following a final wash, cells were evaluated at a wavelength of 488 nm for the presence of fluorescence.

Figure 30:
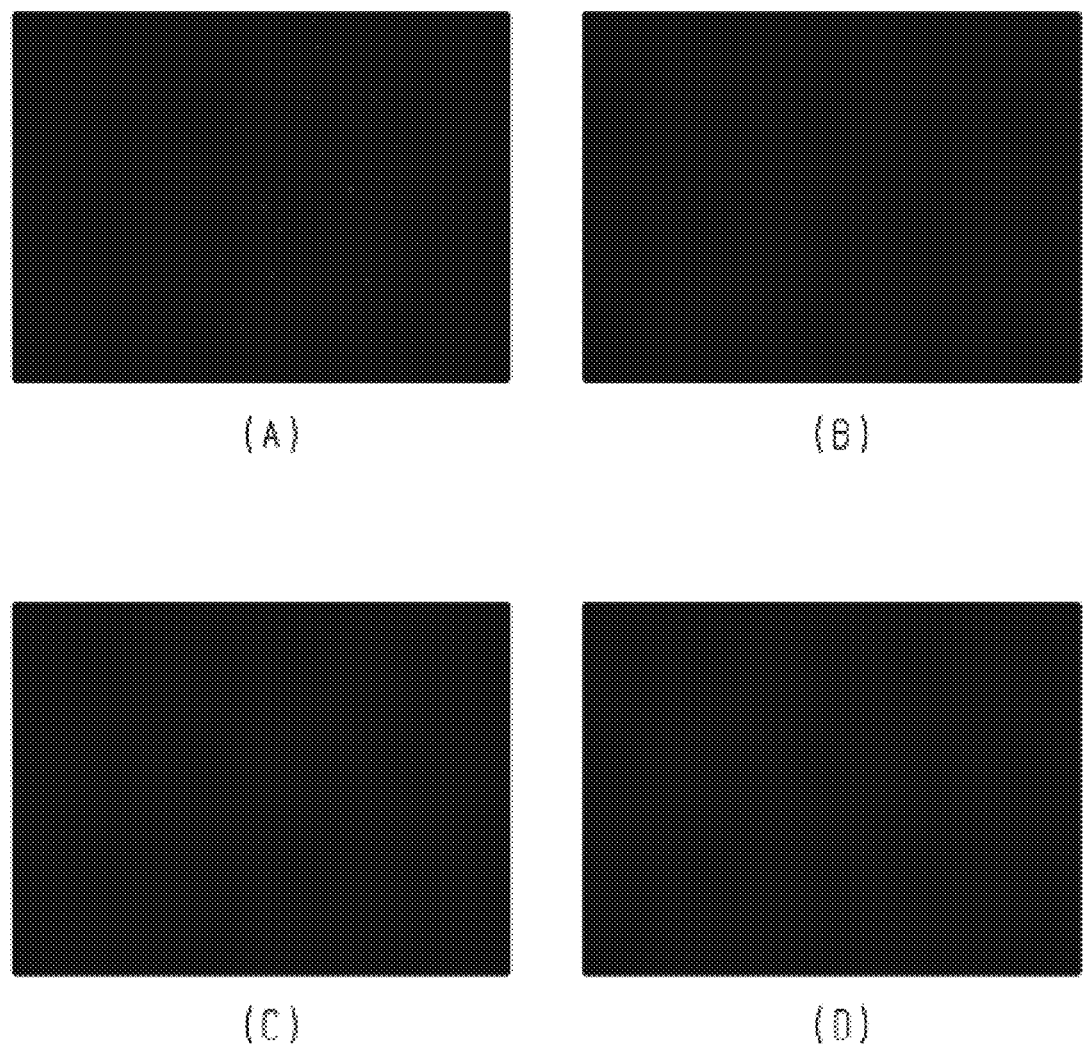
FIG. 30 is a set of immunofluorescence photographs showing cell monolayers treated with an embodiment of the coating composition, Example 252, for varying time periods (a), (b), and (c), and a control Example 253 (d).

FIG. 30 discloses immunofluorescence photos of cells pretreated treated with test Example 253 at FIG. 30(d) T–1 hr, FIG. 30(b) T–30 min and FIG. 30(c) T–0 (immediate). The cells treated with Example 253 for 1 hour and 30 minutes displayed no immunofluorescence. The cells treated with Example 253 for T–0 (immediate) demonstrated scant fluorescence. However, the untreated control Example 254 showed substantial immunofluorescence suggesting profound viral infection (FIG. 30(a)).

Viral load for the samples was quantified as follows: Cell culture supernatants were collected and stored at –80° C. Nucleic acid was extracted using QIAamp Viral RNA Kit (QIAGEN, Valencia, CA). Random hexamer primers (Invitrogen Carlsbad, CA) were used to create a cDNA library for each specimen. Reverse transcription reactions were performed with M-MLV RT (Invitrogen, Carlsbad, CA) according to the manufacturer's specifications. Quantitative analysis was performed on a StepOne Plus Taqman Real Time PCR (Applied Biosystems, Branchburg, NJ) using TaqMan Universal PCR Master Mix (Applied Biosystems, Branchburg, NJ), 2 microliter of cDNA sample, and primers/probes targeting the rhinovirus polyprotein gene. A reference standard was prepared using an amplicon amplified by conventional RT-PCR, gel purified (QIAquick, Qiagen, Valencia, CA), and quantified using a spectrophotometer (Beckman Coulter, Brea, CA). The results are shown in Table XVII.

TABLE XVII

| | Amount | Viral load/mL |
|---|---|---|
| Example 253: 1 hour pretreatment | 0 | 0 |
| Example 253: 30 minute pretreatment | 0 | 0 |
| Example 253: Immediate pretreatment | 0 | 0 |
| Example 254 (control) | 331025.2 | $1.32 \times 10^8$ |

No rhinovirus amplification was apparent at T–1 hour, T–30 min, or T–0 (immediate) timepoints at 5 day post infection. Untreated (control) cells demonstrated substantial amplification (>$10^8$ copies/ml) suggesting viral infection.

Example 255

Cetylpyridinium Chloride Composition Exhibits Antimicrobial Activity on Inanimate Surfaces In Example 255 a cetylpyridinium chloride-based spray disinfectant was evaluated for its activity against methicillin-resistant *Staphylococcus aureus* (MRSA). The antibacterial effect of pre-coating surfaces with the composition was analyzed, and the effect of a water rinse on maintaining its activity was also analyzed.

In an embodiment, the coating composition containing cetylpyridinium chloride retains a substantial amount of its cidal or static activity even on stainless steel surfaces after washing with water, such as at least about 35%, about 35% tor (Bkc-EtOH) and were identically tested. Cells with no disinfectant and phosphate-buffered saline treatment were used as controls.

Figure 31:
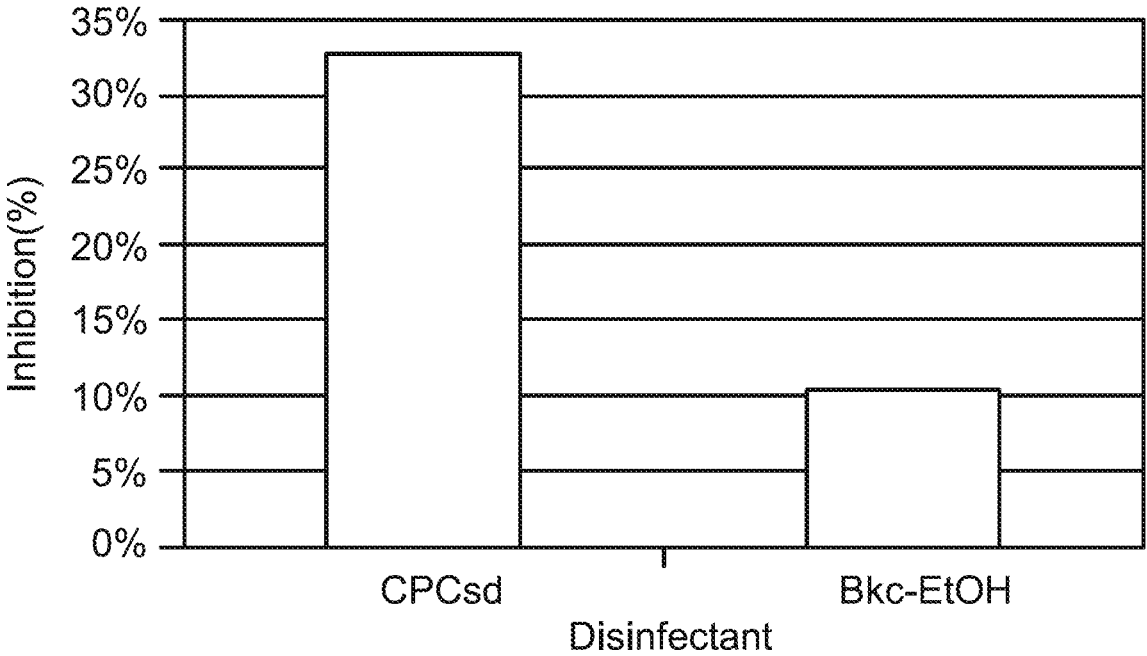
FIG. 31 is a graph showing a test composition and a comparison after a water-wash that corresponds to Example 255.

After the water rinse, and after 16-24 hours carriers treated with $CPC_{sd}$ still exhibited 33% reduction in bacterial counts, compared to a 10% reduction in carriers treated with the comparator (FIG. 31). Therefore, the test composition, $CPC_{sd}$, was able to maintain 3-fold higher activity than the comparator after a water rinse.

Examples 256

A comparison is presented of the composition tested in Example 255 and common alcohol-based household cleaners.

TABLE XXVIII

|  | Flammable | Toxic | Irritation Hazard | Generally safe for Children | Anti-microbial activity prior to rinse | Anti-microbial activity after rinse |
|---|---|---|---|---|---|---|
| Example 255 composition | No | No | No | Yes | ~1x | .33x |
| Comparative Commerical Alcohol-Based Cleaner (58% ethanol) | Yes | Yes | Yes | No | ~1x | .10x | to about 50%, or about 15% to about 40% of cidal or static activity after washing with water.

The test CPC composition had the following formula: 93% to 97% water, 0.5 to 1% CPC antimicrobial, 0.5 to 1% glycerin, with the remainder of the composition comprising preservatives, such as cremophor RH 60, copovidone, parabens, and sodium benzoate, none of which were present in an amount more than about 1%.

The activity of the test CPC composition ($CPC_{sd}$) was evaluated by soaking stainless steel carriers with MRSA suspension ($1\times10^8$ cells) for 15 min at 37° C. Next, excess fluid was drained, the carriers sprayed with $CPC_{sd}$ (0.5 ml dosages) for 30 seconds, air dried, and incubated in Brain heart infusion medium (BHI) overnight. Aliquots of the medium were then quantitatively cultured.

To determine the effect on pre-coated carriers, discs were sprayed with $CPC_{sd}$, (0.50 ml dosages), air-dried for 2-4 minutes, and inoculated with MRSA for 15 minutes at 37° C. Excess fluid was drained and carriers incubated in BHI overnight followed by quantitative culture.

The results showed that $CPC_{sd}$ inhibited the growth of MRSA on contaminated carriers (CFU count=0). This was compared to control sample that still had a CFU count of $2.54\times10^8$. Moreover, pre-coating with $CPC_{sd}$ prevented bacterial contamination of carriers (CFU=0). This was compared to a control with a CFU count of $3.5\times10^8$.

A commercial disinfectant containing benzalkonium chloride and ethanol was used as a comparator (Bkc-EtOH), and was identically tested. The comparator also showed similar antibacterial activity.

The effect of a water rinse on sustained disinfectant activity was studied by washing precoated carriers with MILLI-Q (by transferring them into 2 ml Milli Q autoclaved water and removed in 2-3 seconds) followed by exposure to MRSA for 15 minutes and the number of colony forming units (CFUs) were determined after incubation for about 16-24 hours at 37° C. A commercial disinfectant containing benzalkonium chloride and ethanol was used as a compara- While the Example 255 composition is comparable in initial antimicrobial activity it is superior in all safety categories and activity after a water rinse.

Examples 257-261

Table XXIX shows a comparison is made by comparing the composition made in Example 255 (Formulation 2) having no gum and only a low humectant percentage with a composition containing the carbohydrate gum component, such as was described in Example 7 (Formulation 1).

TABLE XXIX

Figure 33:
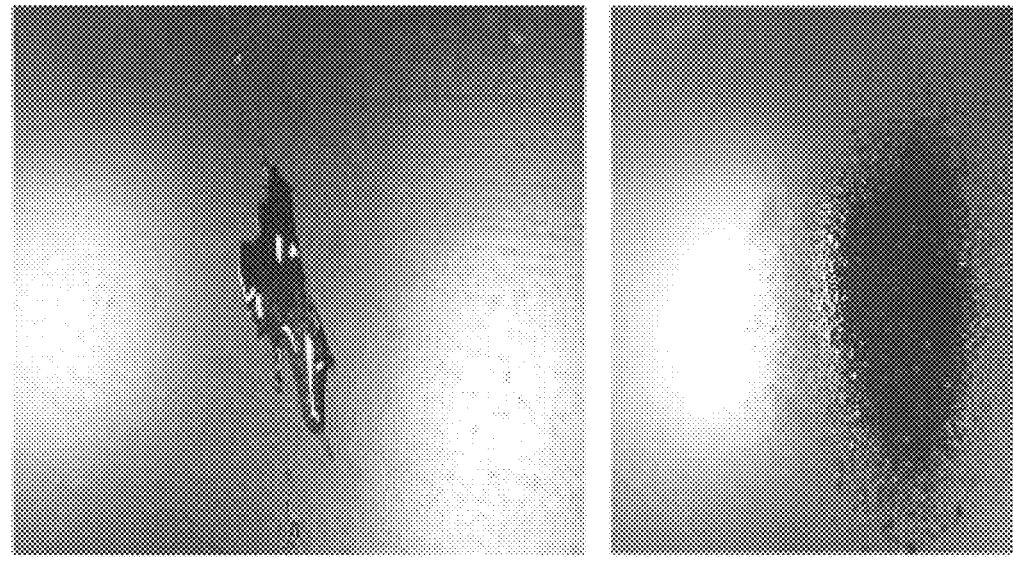
FIG. 33 shows photographs depicting a gum-containing embodiment in comparison to a no-gum embodiment demonstrating viscosity, thickness, and surface coverage differences.

|  | Example 257 Stickiness (Tack) | Example 258 Viscosity | Example 259 Thickness | Example 260 Surface Area covered per mL | Example 261 Filmy residue |
|---|---|---|---|---|---|
| Formulation 1 (Gum) | Higher | Higher | Higher | Lower | Yes |
| Formulation 2 (No gum, low humectant) | Lower | Lower | Lower | Higher | No |
| Evidence Reference | FIG. 32 | FIG. 33 and 32 | FIG. 2 and 33 | FIG. 33 | FIG. 34 |

In Examples 257-259, shown in FIG. 32, testing was conducted by spraying a 0.25 ml dose of formulation 1 on one paper-stock card. Then a second paper-stock card was applied for one second and pulled away. The cards were photographed to analyze whether any residue on the original card was continuously attached to both cards after the second card was applied and subsequently removed. As can be seen in FIG. 32, the Formulation 1 composition was still sticking to the test cards at a draw depth of about 0.5 inches. The same method was followed with Formula 2, and at the same draw there was no residue sticking to the second card. A difference in viscosity and coating thickness can also be seen between the two formulations tested.

In Examples 258-260, shown in FIG. 33, testing for viscosity, layer thickness, and surface area coverage was conducted by spraying a 0.25 ml doses of Formulation 1 and 2 on a lacquer covered fiber board and then photographed. A thicker coating and a smaller surface area was observed in the Formulation 1 test verses the Formulation 2 test. It was also apparent that the viscosity was higher in the Formulation 1 test compared to the Formulation 2 test.

In Example 261, shown in FIG. 34, a glass window pane was cleaned and polished so it was spotless. A 0.25 ml dose of Formulation 1 was centrally applied and then wiped concentrically in an area of approximately 12 inches in height and width. The window was then photographed to analyze whether the formulation left any visible residue (or "streaking") on the glass after being firmly wiped. This test method was repeated for Formulation 2. It was observed that the test Formulation 1 left a noticeable streak or visible residue, whereas the test Formulation 2 was free of any streaking or visible residue.

Each of Examples 257-261 were conducted at room temperature, approximately 21° C.

Examples 262-295

A test composition (Example 7 at 0.05% CPC antimicrobial, instead of 0.1% CPC antimicrobial) was tested against controls on catheters. Thirty-three urinary catheters (examples 262-295) were collected following removal from patients and documented indwelling time and gender were noted. Specimens were stored at 4° C. until the time of analysis (within 24 h of collection). Silver-coated catheters were excluded from collection.

Nonadherent bacteria and debris from catheters were removed through rinsing in two liters of water, and then 10 ml of water irrigated through the catheter lumen via a sterile syringe. Thus, remaining bacteria were adherent in the form of biofilms. Catheters were bisected translumenally and stained for adherent biofilms with 0.1% crystal violet solution for 15 minutes. Catheters were rinsed twice (1 liter each) using 1×PBS and dried by capillary action on absorbent paper, and further sectioned into 1 cm pieces. Each piece was placed in a 24-88 well plate and 1 ml 80% ethanol, 20% acetone solution was added to each well to solubilize the crystal violet. Adherent dye, which represented adherent biofilm, was dissolved in acetic acid, and biofilm concentration was quantitated relative to controls using spectrophotometry. Viability was confirmed in liquid culture.

Intraluminal catheter swabs were obtained, incubated overnight in liquid Luria-Bertani medium at 37 C and examined for turbidity to determine the presence of microbial growth. Samples were then mixed with glycerol and preserved in cryovials at −80 C. Aliquots (500 μl) were shipped to the MicroGen Diagnostics (Lubbock, TX) laboratory for speciation by next-generation sequencing analysis. Briefly, the MicroGenDX assay uses both qPCR and 16s ribosomal RNA to test against the database of 25,000 species of bacteria and fungi as well as relative proportion of species within the sample. The assay also detects resistance factors for antibiotics.

Five isolates were cultured overnight from glycerol stocks and normalized by $OD_{600}$. Each overnight culture was then diluted 1:10 and sub-cultured in the presence of the 1:10 or 1:100 antiseptic formulation (composition of Example 7, except the antiseptic content was 0.05% instead of 0.1%), or a normal saline control.

Results

Of the thirty-three urinary catheters that were collected, biofilm formation was detected as early as several hours indwelling time and increased as a function of time up to 5 weeks. Male and female biofilm growth trends did not differ overall. The luminal and balloon portions of the urinary catheters exhibited predominant biofilm formation. The distal end of the catheter exhibited higher biofilm formation relative to the proximal end (p=0.034).

Next-generation sequencing detected uropathogenic bacteria in 10 of 10 samples analyzed (See FIG. 37). To determine the bacterial species that composed the biofilms on the urinary catheters, swab samples were obtained during biofilm staining and 10 samples were sent for next-generation sequencing analysis using the MicroGenDX platform. Bacteria were detected on all analyzed samples (Table 1). The most commonly detected bacteria were *Enterococcus faecalis* and *Escherichia coli*. Other bacteria detected included *Klebsiella pneumoniae, Staphylococcus aureus,* and *Staphylococcus epidermidis*. Bacterial resistance genes were detected in 4 of the 10 samples. Detected genes conferred resistance to beta-lactam, quinolone, aminoglycoside, and tetracycline drugs. There were no fungi detected in the samples.

Figure 38:
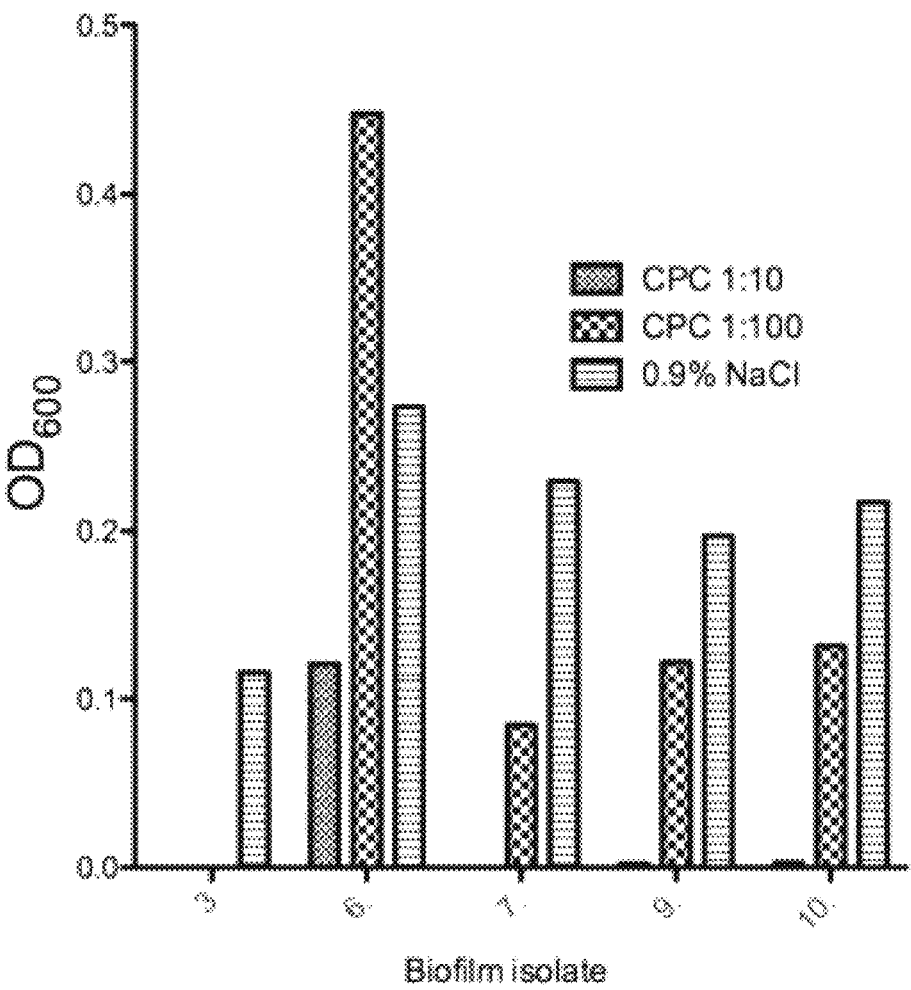
FIG. 38 is a graph showing optical density of certain biofilm isolates.

Bacterial isolates consistently exhibited growth inhibition in a dose-response manner by the test composition relative to the normal saline control (FIG. 38). Five isolates were cultured overnight from glycerol stocks and normalized by $OD_{600}$. Each overnight culture was then diluted 1:100 and sub-cultured in the presence of the 1:10 or 1:100 antiseptic test composition, or a normal saline control. Each subculture was grown at 37 degrees C. for 24 hours, and $OD_{600}$ was then quantitated spectrometrically. The $OD_{600}$ was then plotted for each strain in the context of normal saline, as well as 1:10 and 1:100 test composition (FIG. 38).

CONCLUSIONS

Biofilms were composed of uropathogenic bacteria, which were frequently resistant to commonly-used antibiotics. The balloon, luminal, and distal portions of catheters exhibited biofilm predominance. Growth of biofilm isolates was inhibited by the antimicrobial formulation of Example 7 in a dose-response manner. Biofilm reduction techniques such as routine irrigation with antiseptics are well-positioned to target the luminal-predominant biofilms and may reduce the risk of CAUTI.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

What is claimed is:

1. A method for preventing or treating a urinary system infection, comprising the steps of:
   instilling through a catheter an antimicrobial coating composition into a urinary system of a mammal;
   the antimicrobial coating composition comprising:
      about 0.07%≤H≤about 70%; and
      about 0.0005%<A
         wherein all percentages are by weight of the total composition;
         wherein H is a humectant; and A is an antimicrobial agent;
         the antimicrobial agent comprising a monoquaternary ammonium compound or pharmaceutically acceptable salt thereof;
         trapping, and neutralizing or killing harmful microorganisms in the urinary system or reducing or killing a biofilm in the urinary system;
         wherein the antimicrobial coating composition dwells in a bladder or urinary tract for 5 sec to 1 hour before removing the antimicrobial coating composition from the bladder or urinary tract.

2. The method of claim 1, further comprising coating an external surface of the catheter with the antimicrobial coating composition.

3. The method of claim 1, wherein the antimicrobial composition coats a surface of a bladder, ureter, urethra, prostate or kidney or any reconstructed organ of the urinary system.

4. The method of claim 1, wherein the antimicrobial coating composition coats a balloon portion of the catheter.

5. The method of claim 1, wherein the antimicrobial coating composition dwells in a bladder or urinary tract for 30 seconds to 5 minutes before removing the antimicrobial coating composition from the bladder or urinary tract.

6. The method of claim 1, wherein the composition meets the following compositional requirements:
   about 0.0001%≤C<about 0.4%;
   about 0.07%≤H≤about 65%; and
   about 0.001%≤A≤about 5%;
   wherein all percentages are by weight of the total composition;
   wherein C is a carbohydrate gum.

7. The method of claim 1, wherein the microorganisms are selected from the group consisting of: *Escherichia coli, Enterococcus* spp., *Klebsiella pneumoniae, Candida* spp., coagulase-negative *Staphylococci, S. aureus, Proteus mirabilis,* and *Pseudomonas aeruginosa, Pseudomonas fluorescens, Citrobacter* spp., *Acinetobacter* spp., or combinations thereof.

8. The method of claim 1, wherein the antimicrobial coating composition effectively reduces or eliminates the biofilm in the urinary system.

9. The method of claim 1, wherein the antimicrobial coating composition is a solution comprising about 75% to about 98% by weight water and a pH of the composition is 6 to about 8.

10. The method of claim 1, wherein the antimicrobial coating composition leaves a coating layer having antimicrobial cidal or static activity for at least about one hour.

11. The method of claim 1, wherein the antimicrobial agent is cetylpyridinium chloride.

12. A method for treating a urinary tract catheter or tubing system comprising:
   moving a bolus of a first antimicrobial coating composition through tubing and equipment coupled to a catheter;
   wherein an interior of the tubing is contacted with a flow or a static presence of the composition for 5 seconds to 60 minutes; wherein the first antimicrobial coating composition comprises:
      about 0.07%≤H≤about 70%; and
      about 0.0005%<A;
   wherein all percentages are by weight of the total composition;
   wherein H is a humectant; and A is an antimicrobial agent;
   wherein the antimicrobial agent comprises a monoquaternary ammonium compound or pharmaceutically acceptable salt thereof;
   wherein the antimicrobial coating composition dwells in a bladder or urinary tract for 5 sec to 1 hour before removing the antimicrobial coating composition from the bladder or urinary tract.

13. The method of claim 12, wherein the antimicrobial agent comprises cetyl pyridinium chloride.

14. The method of claim 12, further comprising:
   coating an external surface of the catheter with the first or a second antimicrobial coating composition.

15. The method of claim 14, further coating an external surface of the catheter with the second antimicrobial coating composition, wherein the second antimicrobial composition is 10 to 500% more viscous than the first antimicrobial composition.

16. The antimicrobial coating composition of claim 15, wherein the first antimicrobial coating composition has a viscosity of less than 500 cps.

17. A method for preventing, reducing or treating catheter-associated urinary tract infections in a urinary tract of a mammal, comprising:
   applying a first coating of a first antimicrobial composition on an interior of a catheter, an exterior of the catheter, or both the interior and exterior of the catheter;
   applying a second coating on a lining of a bladder of the mammal by instilling through the catheter a second antimicrobial composition into a bladder or kidney of a mammal;
   in the first coating and the second coating, killing or neutralizing microorganisms encountered on a surface of the catheter or a surface of the bladder or kidney or encountered from an environment after the applying steps are performed; and
   the composition comprising a monoquaternary ammonium compound or pharmaceutically acceptable salt thereof;
   wherein the first and second coating are different;
      wherein the first or second antimicrobial coating composition dwells in a bladder or urinary tract for 5 sec to 1 hour before removing the first or second antimicrobial coating composition from the bladder or urinary tract;
   wherein the first and second antimicrobial compositions are different and independently comprise:
      about 0.07%≤H≤about 70%; and
      about 0.001%≤A≤about 5%;
      wherein all percentages are by weight of the total composition;

wherein H is a humectant; and A is an antimicrobial agent.

18. The method of claim 17, wherein the first antimicrobial coating composition is 10 to 500% more viscous than the second antimicrobial composition.

19. The method of claim 17, wherein the first coating, second coating or first and second coatings have an antimicrobial cidal or static activity for at least about one hour.

20. The method of claim 17, wherein the second antimicrobial composition is 10 to 500% more viscous than the first antimicrobial composition.

* * * * *